United States Patent
Suzuki et al.

(10) Patent No.: US 8,822,165 B2
(45) Date of Patent: Sep. 2, 2014

(54) METHOD FOR PRODUCING CAMP USING CHIMERIC OLFACTORY RECEPTOR

(75) Inventors: Masato Suzuki, Kyoto (JP); Hiroaki Oka, Osaka (JP); Shigeki Kiyonaka, Kyoto (JP); Yasuo Mori, Kyoto (JP)

(73) Assignee: Panasonic Corporation, Osaka (JP)

( * ) Notice: Subject to any disclaimer, the term of this patent is extended or adjusted under 35 U.S.C. 154(b) by 21 days.

(21) Appl. No.: 13/598,294

(22) Filed: Aug. 29, 2012

(65) Prior Publication Data

US 2013/0065244 A1 Mar. 14, 2013

Related U.S. Application Data

(63) Continuation of application No. PCT/JP2011/005950, filed on Oct. 24, 2011.

(30) Foreign Application Priority Data

Oct. 25, 2010 (JP) .................................. 2010-238202
Apr. 27, 2011 (WO) .................. PCT/JP2011/002477

(51) Int. Cl.

| | | |
|---|---|---|
| C07K 14/705 | (2006.01) | |
| C07K 19/00 | (2006.01) | |
| G01N 33/566 | (2006.01) | |
| C12P 19/32 | (2006.01) | |
| C07K 14/47 | (2006.01) | |
| C07K 14/72 | (2006.01) | |
| G01N 33/68 | (2006.01) | |

(52) U.S. Cl.
CPC ............... *C07K 14/705* (2013.01); *C12P 19/32* (2013.01); *C07K 2319/41* (2013.01); *C07K 14/70571* (2013.01); *C07K 14/47* (2013.01); *C07K 2319/00* (2013.01); *C07K 14/723* (2013.01); *G01N 33/6872* (2013.01); *G01N 2500/04* (2013.01); *G01N 2333/726* (2013.01)
USPC ........... 435/7.2; 435/7.21; 435/69.7; 436/501

(58) Field of Classification Search
None
See application file for complete search history.

(56) References Cited

U.S. PATENT DOCUMENTS

| | | | |
|---|---|---|---|
| 8,450,066 B2* | 5/2013 | Kenten et al. ................. | 435/6.13 |
| 2002/0146843 A1* | 10/2002 | Kenten et al. .................. | 436/501 |

FOREIGN PATENT DOCUMENTS

| | | |
|---|---|---|
| JP | 2004-135656 A | 5/2004 |
| JP | 2008-503220 A | 2/2008 |
| WO | WO-2006/002161 A2 | 1/2006 |

OTHER PUBLICATIONS

Noel M.Delos Santos et al., Characterization of the Residues in Helix 8 of the Human beta 1-adrenergic receptor that are involved in coupling the receptor to G Proteins (2006) J. Biol. Chem. 281, 12896-12907.

Kato A. et al., Amino Acids involved in conformational dynamics and G protein coupling of an odorant receptor: targeting gain-of-function mutation (2008) J. Neurochem., 107, 1261-1270.

Katada S. et al., Structural determinants for membrane trafficking and G protein selectivity of a mouse olfactory receptor (2004) J. Neurochem., 90, 1453-1463.

Katada, Sayako et al., Structural basis for a broad but selective ligand spectrum of a mouse olfactory receptor: mapping the odorant-binding site., J. Neurosci., 2005, vol. 25, No. 7, p. 1806-1815, Introduction, Materials and Methods, Figure 2B.

McClintock, Timothy S. et al., Functional expression of olfactory-adrenergic receptor chimeras and intracellular rentention of heterologously expressed olfactory receptors., Mol. Brain Res., vol. 48, 1997, p. 270-278, Table 1.

Kim, Jong-Myoung et al., Light-driven activation of beta 2-adrenergic receptor signaling by a chimeric rhodopsin containing the beta 2-adrenergic receptor cytoplasmic loops., Biochemistry, vol. 44, 2005, p. 2284-2292, Figure 1.

Mangmool, Supachoke et al., beta-Arrestin-dependent activation of Ca2+/calmodulin kinase II after beta1-adrenergic receptor stimulation., J. Cell. Biol., Apr. 2010, vol. 189, No. 3, p. 573-587, Figure 6.

National Center for Biotechnology Information. Protein. Accession Q8VF05. [online]., 2006, [retrieved on Nov. 18, 2011]. Retrieved from the Internet: <URL:http://www.ncbi.nlm.nih.gov/protein/q8vf05>.

National Center for Biotechnology Information. Protein. Accession P23275. [online]., Oct. 5, 2010, [retrieved on Nov. 18, 2011]. Retrieved from the Internet: <URL:http://www.ncbi.nlm.nih.gov/protein/209572776?sat=13&satkey=1483545>.

National Center for Biotechnology Information. Protein. Accession NP_667293. [online]., 2009, [retrieved on Nov. 18, 2011]. Retrieved from the Internet: <URL:http://www.ncbi.nlm.nih.gov/protein/268607590?sat=14&satkey=4843137>.

National Center for Biotechnology Information. Protein. Accession Q920P2. [online]., 2006, [retrieved on Nov. 18, 2011]. Retrieved from the Internet: <URL:http://www.ncbi.nlm.nih.gov/protein/q920p2>.

(Continued)

*Primary Examiner* — John Ulm
(74) *Attorney, Agent, or Firm* — McDermott Will & Emery LLP

(57) ABSTRACT

A method for producing cAMP using a chimeric olfactory receptor. The method includes a step of preparing a reaction system comprising a first layer, a lipid bilayer membrane, and a second layer, and a step of supplying a chemical substance which stimulates the chimeric olfactory receptor to the first layer so as to produce the cAMP from ATP. The lipid bilayer membrane includes the chimeric olfactory receptor and adenylate cyclase. The chimeric olfactory receptor penetrates the lipid bilayer membrane. The second layer contains ATP and a G protein. The G protein is placed in the vicinity of one end of the chimeric olfactory receptor. The chimeric olfactory receptor is derived from a mouse olfactory receptor and the N-terminal of the chimeric olfactory receptor is modified with an amino acid sequence.

50 Claims, 17 Drawing Sheets

(56) References Cited

OTHER PUBLICATIONS

Katada, Sayako et al., Odorant response assays for a heterologously expressed olfactory receptor., Biochem. Biophys. Res. Commun., 2003, vol. 305, No. 4, p. 964-969.

Gehret, Austin U. and Hinkle, Patricia M., Importance of regions outside the cytoplasmic tail of G-protein-coupled receptors for phosphorylation and dephosphorylation., Biochem. J., May 2010, vol. 428, No. 2, p. 235-245.

Zhang, Xinmin and Firestein, Stuarr, The olfactory receptor gene superfamily of the mouse. Nat. Neurosci., 2002, vol. 5, No. 2, p. 124-133.

Akiyama, Chiyuki et al., Analysis of domain responsible for desensitization of beta1-adrenergic receptor., Jpn. J. Pharmacol., 1999, vol. 81, No. 1, p. 12-20.

Katada, S and K. Touhara, A molecular basis for odorant recognition: olfactory receptor pharmacology., Folia Pharmacologica Japonica, 2004, vol. 124, No. 4, p. 201-209.

International Search Report mailed Nov. 29, 2011 issued in corresponding International Application No. PCT/JP2011/005950.

Godfrey et al., The mouse olfactory receptor gene family, *Proc. Natl. Acad. Sci. USA*, vol. 101, No. 7, 2156-2161 (Feb. 17, 2004).

* cited by examiner

SEQUENCE LISTING

<160> NUMBER OF SEQ ID NOS: 71

<210> SEQ ID NO 1
<211> LENGTH: 20
<212> TYPE: PRT
<213> ORGANISM: Bos taurus

<400> SEQUENCE: 1

Met Asn Gly Thr Glu Gly Pro Asn Phe Tyr Val Pro Phe Ser Asn Lys
1               5                   10                  15

Thr Gly Val Val
            20

<210> SEQ ID NO 2
<211> LENGTH: 313
<212> TYPE: PRT
<213> ORGANISM: Mus musculus

<400> SEQUENCE: 2

Met Thr Leu Ser Asp Gly Asn His Ser Gly Ala Val Phe Thr Leu Leu
1               5                   10                  15

Gly Phe Ser Asp Tyr Pro Glu Leu Thr Ile Pro Leu Phe Leu Ile Phe
                20                  25                  30

Leu Thr Ile Tyr Ser Ile Thr Val Val Gly Asn Ile Gly Met Ile Val
            35                  40                  45

Ile Ile Arg Ile Asn Pro Lys Leu His Ile Pro Met Tyr Phe Phe Leu
        50                  55                  60

Ser His Leu Ser Phe Val Asp Phe Cys Tyr Ser Ser Ile Val Ala Pro
65                  70                  75                  80

Lys Met Leu Val Asn Leu Val Thr Met Asn Arg Gly Ile Ser Phe Val
                85                  90                  95

Gly Cys Leu Val Gln Phe Phe Phe Cys Thr Phe Val Val Thr Glu
                100                 105                 110

Ser Phe Leu Leu Gly Val Met Ala Tyr Asp Arg Phe Val Ala Ile Arg
            115                 120                 125

Asn Pro Leu Leu Tyr Thr Val Ala Met Ser Gln Arg Leu Cys Ala Met
        130                 135                 140

Leu Val Leu Gly Ser Tyr Ala Trp Gly Val Val Cys Ser Leu Ile Leu
145                 150                 155                 160

Thr Cys Ser Ala Leu Asn Leu Ser Phe Tyr Gly Phe Asn Met Ile Asn
                165                 170                 175

His Phe Phe Cys Glu Phe Ser Ser Leu Leu Ser Leu Ser Arg Ser Asp
            180                 185                 190

Thr Ser Val Ser Gln Leu Leu Leu Phe Val Phe Ala Thr Phe Asn Glu
        195                 200                 205

Ile Ser Thr Leu Leu Ile Ile Leu Leu Ser Tyr Val Leu Ile Val Val
    210                 215                 220

Thr Ile Leu Lys Met Lys Ser Ala Ser Gly Arg Arg Lys Ala Phe Ser
225                 230                 235                 240

Thr Cys Ala Ser His Leu Thr Ala Ile Thr Ile Phe His Gly Thr Ile
                245                 250                 255

Leu Phe Leu Tyr Cys Val Pro Asn Ser Lys Asn Ser Arg His Thr Val
            260                 265                 270

Lys Val Ala Ser Val Phe Tyr Thr Val Val Ile Pro Met Leu Asn Pro
        275                 280                 285

Leu Ile Tyr Ser Leu Arg Asn Lys Asp Val Lys Asp Thr Val Lys Lys

```
            290                 295                 300
Ile Ile Gly Thr Lys Val Tyr Ser Ser
305                 310

<210> SEQ ID NO 3
<211> LENGTH: 466
<212> TYPE: PRT
<213> ORGANISM: Rattus norvegicus

<400> SEQUENCE: 3

Met Gly Ala Gly Ala Leu Ala Leu Gly Ala Ser Glu Pro Cys Asn Leu
1               5                   10                  15

Ser Ser Ala Ala Pro Leu Pro Asp Gly Ala Ala Thr Ala Ala Arg Leu
            20                  25                  30

Leu Val Leu Ala Ser Pro Pro Ala Ser Leu Leu Pro Pro Ala Ser Glu
        35                  40                  45

Gly Ser Ala Pro Leu Ser Gln Gln Trp Thr Ala Gly Met Gly Leu Leu
    50                  55                  60

Leu Ala Leu Ile Val Leu Leu Ile Val Val Gly Asn Val Leu Val Ile
65                  70                  75                  80

Val Ala Ile Ala Lys Thr Pro Arg Leu Gln Thr Leu Thr Asn Leu Phe
                85                  90                  95

Ile Met Ser Leu Ala Ser Ala Asp Leu Val Met Gly Leu Leu Val Val
            100                 105                 110

Pro Phe Gly Ala Thr Ile Val Val Trp Gly Arg Trp Glu Tyr Gly Ser
        115                 120                 125

Phe Phe Cys Glu Leu Trp Thr Ser Val Asp Val Leu Cys Val Thr Ala
    130                 135                 140

Ser Ile Glu Thr Leu Cys Val Ile Ala Leu Asp Arg Tyr Leu Ala Ile
145                 150                 155                 160

Thr Leu Pro Phe Arg Tyr Gln Ser Leu Leu Thr Arg Ala Arg Ala Arg
                165                 170                 175

Ala Leu Val Cys Thr Val Trp Ala Ile Ser Ala Leu Val Ser Phe Leu
            180                 185                 190

Pro Ile Leu Met His Trp Trp Arg Ala Glu Ser Asp Glu Ala Arg Arg
        195                 200                 205

Cys Tyr Asn Asp Pro Lys Cys Cys Asp Phe Val Thr Asn Arg Ala Tyr
    210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
                245                 250                 255

Lys Ile Asp Ser Cys Glu Arg Arg Phe Leu Thr Gly Pro Pro Arg Pro
            260                 265                 270

Pro Ser Pro Ala Pro Ser Pro Gly Pro Pro Arg Pro Ala Asp
        275                 280                 285

Ser Leu Ala Asn Gly Arg Ser Ser Lys Arg Arg Pro Ser Arg Leu Val
    290                 295                 300

Ala Leu Arg Glu Gln Lys Ala Leu Lys Thr Leu Gly Ile Ile Met Gly
305                 310                 315                 320

Val Phe Thr Leu Cys Trp Leu Pro Phe Phe Leu Ala Asn Val Val Lys
                325                 330                 335

Ala Phe His Arg Asp Leu Val Pro Asp Arg Leu Phe Val Phe Phe Asn
            340                 345                 350
```

```
Trp Leu Gly Tyr Ala Asn Ser Ala Phe Asn Pro Ile Ile Tyr Cys Arg
            355                 360                 365

Ser Pro Asp Phe Arg Lys Ala Phe Gln Arg Leu Leu Cys Cys Ala Arg
    370                 375                 380

Arg Ala Ala Cys Arg Arg Arg Ala Ala His Gly Asp Arg Pro Arg Ala
385                 390                 395                 400

Ser Gly Cys Leu Ala Arg Ala Gly Pro Pro Pro Ser Pro Gly Ala Pro
                405                 410                 415

Ser Asp Asp Asp Asp Asp Ala Gly Ala Thr Pro Pro Ala Arg Leu
            420                 425                 430

Leu Glu Pro Trp Ala Gly Cys Asn Gly Gly Thr Thr Thr Val Asp Ser
            435                 440                 445

Asp Ser Ser Leu Asp Glu Pro Gly Arg Gln Gly Phe Ser Ser Glu Ser
    450                 455                 460

Lys Val
465
```

```
<210> SEQ ID NO 4
<211> LENGTH: 10
<212> TYPE: PRT
<213> ORGANISM: Artificial
<220> FEATURE:
<223> OTHER INFORMATION: Tag for labelling with antibody

<400> SEQUENCE: 4

Glu Gln Lys Leu Ile Ser Glu Glu Asp Leu
1               5                   10

<210> SEQ ID NO 5
<211> LENGTH: 19
<212> TYPE: DNA
<213> ORGANISM: Artificial
<220> FEATURE:
<223> OTHER INFORMATION: primer for preparing plasmid expressing beta
      one adrenergic receptor

<400> SEQUENCE: 5
atgggcgcgg gggcgctcg                                                  19

<210> SEQ ID NO 6
<211> LENGTH: 28
<212> TYPE: DNA
<213> ORGANISM: Artificial
<220> FEATURE:
<223> OTHER INFORMATION: primer for preparing plasmid expressing beta
      one adrenergic receptor

<400> SEQUENCE: 6
gaagacgaag aggcgatccg gcaccagg                                        28

<210> SEQ ID NO 7
<211> LENGTH: 28
<212> TYPE: DNA
<213> ORGANISM: Artificial
<220> FEATURE:
<223> OTHER INFORMATION: primer for preparing plasmid expressing beta
      one adrenergic receptor

<400> SEQUENCE: 7
cactgggcat catcatgggt gtgttcac                                        28

<210> SEQ ID NO 8
<211> LENGTH: 27
```

```
<212> TYPE: DNA
<213> ORGANISM: Artificial
<220> FEATURE:
<223> OTHER INFORMATION: primer for preparing plasmid expressing beta
      one adrenergic receptor

<400> SEQUENCE: 8
ctacaccttg gactcggagg agaagcc                                           27

<210> SEQ ID NO 9
<211> LENGTH: 32
<212> TYPE: DNA
<213> ORGANISM: Artificial
<220> FEATURE:
<223> OTHER INFORMATION: primer for preparing plasmid expressing beta
      one adrenergic receptor

<400> SEQUENCE: 9
ttcgaattcg ccaccatggg cgcgggggcg ct                                     32

<210> SEQ ID NO 10
<211> LENGTH: 29
<212> TYPE: DNA
<213> ORGANISM: Artificial
<220> FEATURE:
<223> OTHER INFORMATION: primer for preparing plasmid expressing beta
      one adrenergic receptor

<400> SEQUENCE: 10
gaagtcgacc tacaccttgg actcggagg                                         29

<210> SEQ ID NO 11
<211> LENGTH: 30
<212> TYPE: DNA
<213> ORGANISM: Artificial
<220> FEATURE:
<223> OTHER INFORMATION: primer for preparing plasmid expressing mouse
      Rho-mOREG

<400> SEQUENCE: 11
ctagactctg tcagatggaa atcacagtgg                                        30

<210> SEQ ID NO 12
<211> LENGTH: 30
<212> TYPE: DNA
<213> ORGANISM: Artificial
<220> FEATURE:
<223> OTHER INFORMATION: primer for preparing plasmid expressing mouse
      Rho-mOREG

<400> SEQUENCE: 12
ttaagaagaa tagactttag tacctattat                                        30

<210> SEQ ID NO 13
<211> LENGTH: 59
<212> TYPE: DNA
<213> ORGANISM: Artificial
<220> FEATURE:
<223> OTHER INFORMATION: primer for preparing plasmid expressing mouse
      Rho-mOREG

<400> SEQUENCE: 13
cgtgcctttc tccaacaaga cgggcgtcgt aatgactctg tcagatggaa atcacagtg        59

<210> SEQ ID NO 14
<211> LENGTH: 59
<212> TYPE: DNA
```

```
<213> ORGANISM: Artificial
<220> FEATURE:
<223> OTHER INFORMATION: primer for preparing plasmid expressing mouse
      Rho-mOREG

<400> SEQUENCE: 14
cgaattcatg aacgggaccg agggcccaaa cttctacgtg cctttctcca acaagacgg        59

<210> SEQ ID NO 15
<211> LENGTH: 26
<212> TYPE: DNA
<213> ORGANISM: Artificial
<220> FEATURE:
<223> OTHER INFORMATION: primer for preparing plasmid expressing mouse
      Rho-myc-mOREG

<400> SEQUENCE: 15
tcccagttca attacagctc ttaagg                                           26

<210> SEQ ID NO 16
<211> LENGTH: 67
<212> TYPE: DNA
<213> ORGANISM: Artificial
<220> FEATURE:
<223> OTHER INFORMATION: primer for preparing plasmid expressing mouse
      Rho-myc-mOREG

<400> SEQUENCE: 16
tgacagagtc atgaattcca gatcctcttc agagatgagt ttctgctcta cgacgcccgt      60
cttgttg                                                               67

<210> SEQ ID NO 17
<211> LENGTH: 35
<212> TYPE: DNA
<213> ORGANISM: Artificial
<220> FEATURE:
<223> OTHER INFORMATION: primer for preparing plasmid expressing mouse
      Rho-myc-mOREG

<400> SEQUENCE: 17
atctggaatt catgactctg tcagatggaa atcac                                 35

<210> SEQ ID NO 18
<211> LENGTH: 39
<212> TYPE: DNA
<213> ORGANISM: Artificial
<220> FEATURE:
<223> OTHER INFORMATION: primer for preparing plasmid expressing mouse
      Rho-myc-mOREG

<400> SEQUENCE: 18
aaagtcgacc cgggattaag aagaatagac tttagtacc                             39

<210> SEQ ID NO 19
<211> LENGTH: 33
<212> TYPE: DNA
<213> ORGANISM: Artificial
<220> FEATURE:
<223> OTHER INFORMATION: primer for preparing plasmid expressing mouse
      chimera 1

<400> SEQUENCE: 19
aagtcgggtc tcagactgta tattagggga ttc                                   33

<210> SEQ ID NO 20
<211> LENGTH: 28
```

```
<212> TYPE: DNA
<213> ORGANISM: Artificial
<220> FEATURE:
<223> OTHER INFORMATION: primer for preparing plasmid expressing mouse
      chimera 1

<400> SEQUENCE: 20
acagtctgag acccgacttc cgcaaggc                                        28

<210> SEQ ID NO 21
<211> LENGTH: 23
<212> TYPE: DNA
<213> ORGANISM: Artificial
<220> FEATURE:
<223> OTHER INFORMATION: primer for preparing plasmid expressing mouse
      chimera 1 and 2

<400> SEQUENCE: 21
atgtctgctc gaagcattaa ccc                                             23

<210> SEQ ID NO 22
<211> LENGTH: 32
<212> TYPE: DNA
<213> ORGANISM: Artificial
<220> FEATURE:
<223> OTHER INFORMATION: primer for preparing plasmid expressing mouse
      chimera 2

<400> SEQUENCE: 22
gagatatcac gcgtgaggtt ggtgagcgtc tg                                   32

<210> SEQ ID NO 23
<211> LENGTH: 34
<212> TYPE: DNA
<213> ORGANISM: Artificial
<220> FEATURE:
<223> OTHER INFORMATION: primer for preparing plasmid expressing mouse
      chimera 2

<400> SEQUENCE: 23
cgtgatatct ctagagactt ccgcaaggct ttcc                                 34

<210> SEQ ID NO 24
<211> LENGTH: 31
<212> TYPE: DNA
<213> ORGANISM: Artificial
<220> FEATURE:
<223> OTHER INFORMATION: primer for preparing plasmid expressing mouse
      chimera 2

<400> SEQUENCE: 24
aaaacgcgtc ccatgtactt ctttctcagc c                                    31

<210> SEQ ID NO 25
<211> LENGTH: 40
<212> TYPE: DNA
<213> ORGANISM: Artificial
<220> FEATURE:
<223> OTHER INFORMATION: primer for preparing plasmid expressing mouse
      chimera 2

<400> SEQUENCE: 25
aaatctagac ttatttctca gactgtatat tagggattc                            40

<210> SEQ ID NO 26
<211> LENGTH: 29
<212> TYPE: DNA
```

```
<213> ORGANISM: Artificial
<220> FEATURE:
<223> OTHER INFORMATION: primer for preparing plasmid expressing G alpha
      olf

<400> SEQUENCE: 26
atggggtgtt tgggcaacag cagcaagac                                    29

<210> SEQ ID NO 27
<211> LENGTH: 26
<212> TYPE: DNA
<213> ORGANISM: Artificial
<220> FEATURE:
<223> OTHER INFORMATION: primer for preparing plasmid expressing G alpha
      olf

<400> SEQUENCE: 27
ggaggaggag gagggtagg tttagg                                        26

<210> SEQ ID NO 28
<211> LENGTH: 35
<212> TYPE: DNA
<213> ORGANISM: Artificial
<220> FEATURE:
<223> OTHER INFORMATION: primer for preparing plasmid expressing G alpha
      olf

<400> SEQUENCE: 28
aatgaattcg ccaccatggg gtgtttgggc aacag                             35

<210> SEQ ID NO 29
<211> LENGTH: 33
<212> TYPE: DNA
<213> ORGANISM: Artificial
<220> FEATURE:
<223> OTHER INFORMATION: primer for preparing plasmid expressing G alpha
      olf

<400> SEQUENCE: 29
aatgtcgact cacaagagtt cgtactgctt gag                               33

<210> SEQ ID NO 30
<211> LENGTH: 26
<212> TYPE: DNA
<213> ORGANISM: Artificial
<220> FEATURE:
<223> OTHER INFORMATION: primer for preparing plasmid expressing RTP1S

<400> SEQUENCE: 30
tgggtcctgc ttcctcctga tcctgc                                       26

<210> SEQ ID NO 31
<211> LENGTH: 27
<212> TYPE: DNA
<213> ORGANISM: Artificial
<220> FEATURE:
<223> OTHER INFORMATION: primer for preparing plasmid expressing RTP1S

<400> SEQUENCE: 31
ccattcccaa gccaggtctc acctcac                                      27

<210> SEQ ID NO 32
<211> LENGTH: 35
<212> TYPE: DNA
<213> ORGANISM: Artificial
<220> FEATURE:
<223> OTHER INFORMATION: primer for preparing plasmid expressing RTP1S
```

-continued

<400> SEQUENCE: 32
cagaattcgc caccatgtgt aagagtgtga ccaca                      35

<210> SEQ ID NO 33
<211> LENGTH: 31
<212> TYPE: DNA
<213> ORGANISM: Artificial
<220> FEATURE:
<223> OTHER INFORMATION: primer for preparing plasmid expressing RTP1S

<400> SEQUENCE: 33
gaagtcgact tagacagaag tacggaagga g                          31

<210> SEQ ID NO 34
<211> LENGTH: 333
<212> TYPE: PRT
<213> ORGANISM: Artificial
<220> FEATURE:
<223> OTHER INFORMATION: Rho-mOREG

<400> SEQUENCE: 34

Met Asn Gly Thr Glu Gly Pro Asn Phe Tyr Val Pro Phe Ser Asn Lys
1               5                   10                  15

Thr Gly Val Val Met Thr Leu Ser Asp Gly Asn His Ser Gly Ala Val
            20                  25                  30

Phe Thr Leu Leu Gly Phe Ser Asp Tyr Pro Glu Leu Thr Ile Pro Leu
        35                  40                  45

Phe Leu Ile Phe Leu Thr Ile Tyr Ser Ile Thr Val Val Gly Asn Ile
    50                  55                  60

Gly Met Ile Val Ile Ile Arg Ile Asn Pro Lys Leu His Ile Pro Met
65                  70                  75                  80

Tyr Phe Phe Leu Ser His Leu Ser Phe Val Asp Phe Cys Tyr Ser Ser
                85                  90                  95

Ile Val Ala Pro Lys Met Leu Val Asn Leu Val Thr Met Asn Arg Gly
            100                 105                 110

Ile Ser Phe Val Gly Cys Leu Val Gln Phe Phe Phe Phe Cys Thr Phe
        115                 120                 125

Val Val Thr Glu Ser Phe Leu Leu Gly Val Met Ala Tyr Asp Arg Phe
    130                 135                 140

Val Ala Ile Arg Asn Pro Leu Leu Tyr Thr Val Ala Met Ser Gln Arg
145                 150                 155                 160

Leu Cys Ala Met Leu Val Leu Gly Ser Tyr Ala Trp Gly Val Val Cys
                165                 170                 175

Ser Leu Ile Leu Thr Cys Ser Ala Leu Asn Leu Ser Phe Tyr Gly Phe
            180                 185                 190

Asn Met Ile Asn His Phe Phe Cys Glu Phe Ser Ser Leu Leu Ser Leu
        195                 200                 205

Ser Arg Ser Asp Thr Ser Val Ser Gln Leu Leu Leu Phe Val Phe Ala
    210                 215                 220

Thr Phe Asn Glu Ile Ser Thr Leu Leu Ile Ile Leu Leu Ser Tyr Val
225                 230                 235                 240

Leu Ile Val Val Thr Ile Leu Lys Met Lys Ser Ala Ser Gly Arg Arg
                245                 250                 255

Lys Ala Phe Ser Thr Cys Ala Ser His Leu Thr Ala Ile Thr Ile Phe
            260                 265                 270

His Gly Thr Ile Leu Phe Leu Tyr Cys Val Pro Asn Ser Lys Asn Ser

```
                    275                 280                 285
Arg His Thr Val Lys Val Ala Ser Val Phe Tyr Thr Val Val Ile Pro
    290                 295                 300

Met Leu Asn Pro Leu Ile Tyr Ser Leu Arg Asn Lys Asp Val Lys Asp
305                 310                 315                 320

Thr Val Lys Lys Ile Ile Gly Thr Lys Val Tyr Ser Ser
                325                 330

<210> SEQ ID NO 35
<211> LENGTH: 345
<212> TYPE: PRT
<213> ORGANISM: Artificial
<220> FEATURE:
<223> OTHER INFORMATION: Rho-myc-mOREG

<400> SEQUENCE: 35

Met Asn Gly Thr Glu Gly Pro Asn Phe Tyr Val Pro Phe Ser Asn Lys
1               5                   10                  15

Thr Gly Val Val Glu Gln Lys Leu Ile Ser Glu Glu Asp Leu Glu Phe
            20                  25                  30

Met Thr Leu Ser Asp Gly Asn His Ser Gly Ala Val Phe Thr Leu Leu
        35                  40                  45

Gly Phe Ser Asp Tyr Pro Glu Leu Thr Ile Pro Leu Phe Leu Ile Phe
    50                  55                  60

Leu Thr Ile Tyr Ser Ile Thr Val Val Gly Asn Ile Gly Met Ile Val
65                  70                  75                  80

Ile Ile Arg Ile Asn Pro Lys Leu His Ile Pro Met Tyr Phe Phe Leu
                85                  90                  95

Ser His Leu Ser Phe Val Asp Phe Cys Tyr Ser Ser Ile Val Ala Pro
            100                 105                 110

Lys Met Leu Val Asn Leu Val Thr Met Asn Arg Gly Ile Ser Phe Val
        115                 120                 125

Gly Cys Leu Val Gln Phe Phe Phe Cys Thr Phe Val Val Thr Glu
    130                 135                 140

Ser Phe Leu Leu Gly Val Met Ala Tyr Asp Arg Phe Val Ala Ile Arg
145                 150                 155                 160

Asn Pro Leu Leu Tyr Thr Val Ala Met Ser Gln Arg Leu Cys Ala Met
                165                 170                 175

Leu Val Leu Gly Ser Tyr Ala Trp Gly Val Val Cys Ser Leu Ile Leu
            180                 185                 190

Thr Cys Ser Ala Leu Asn Leu Ser Phe Tyr Gly Phe Asn Met Ile Asn
        195                 200                 205

His Phe Phe Cys Glu Phe Ser Ser Leu Leu Ser Leu Ser Arg Ser Asp
    210                 215                 220

Thr Ser Val Ser Gln Leu Leu Phe Val Phe Ala Thr Phe Asn Glu
225                 230                 235                 240

Ile Ser Thr Leu Leu Ile Ile Leu Leu Ser Tyr Val Leu Ile Val Val
                245                 250                 255

Thr Ile Leu Lys Met Lys Ser Ala Ser Gly Arg Arg Lys Ala Phe Ser
            260                 265                 270

Thr Cys Ala Ser His Leu Thr Ala Ile Thr Ile Phe His Gly Thr Ile
        275                 280                 285

Leu Phe Leu Tyr Cys Val Pro Asn Ser Lys Asn Ser Arg His Thr Val
    290                 295                 300

Lys Val Ala Ser Val Phe Tyr Thr Val Val Ile Pro Met Leu Asn Pro
```

Leu Ile Tyr Ser Leu Arg Asn Lys Asp Val Lys Asp Thr Val Lys Lys
                325                 330                 335

Ile Ile Gly Thr Lys Val Tyr Ser Ser
            340                 345

<210> SEQ ID NO 36
<211> LENGTH: 424
<212> TYPE: PRT
<213> ORGANISM: Artificial
<220> FEATURE:
<223> OTHER INFORMATION: chimera 1

<400> SEQUENCE: 36

Met Asn Gly Thr Glu Gly Pro Asn Phe Tyr Val Pro Phe Ser Asn Lys
1               5                   10                  15

Thr Gly Val Val Glu Gln Lys Leu Ile Ser Glu Glu Asp Leu Glu Phe
            20                  25                  30

Met Thr Leu Ser Asp Gly Asn His Ser Gly Ala Val Phe Thr Leu Leu
        35                  40                  45

Gly Phe Ser Asp Tyr Pro Glu Leu Thr Ile Pro Leu Phe Leu Ile Phe
    50                  55                  60

Leu Thr Ile Tyr Ser Ile Thr Val Val Gly Asn Ile Gly Met Ile Val
65                  70                  75                  80

Ile Ile Arg Ile Asn Pro Lys Leu His Ile Pro Met Tyr Phe Phe Leu
                85                  90                  95

Ser His Leu Ser Phe Val Asp Phe Cys Tyr Ser Ser Ile Val Ala Pro
            100                 105                 110

Lys Met Leu Val Asn Leu Val Thr Met Asn Arg Gly Ile Ser Phe Val
        115                 120                 125

Gly Cys Leu Val Gln Phe Phe Phe Cys Thr Phe Val Val Thr Glu
    130                 135                 140

Ser Phe Leu Leu Gly Val Met Ala Tyr Asp Arg Phe Val Ala Ile Arg
145                 150                 155                 160

Asn Pro Leu Leu Tyr Thr Val Ala Met Ser Gln Arg Leu Cys Ala Met
                165                 170                 175

Leu Val Leu Gly Ser Tyr Ala Trp Gly Val Val Cys Ser Leu Ile Leu
            180                 185                 190

Thr Cys Ser Ala Leu Asn Leu Ser Phe Tyr Gly Phe Asn Met Ile Asn
        195                 200                 205

His Phe Phe Cys Glu Phe Ser Ser Leu Leu Ser Leu Ser Arg Ser Asp
    210                 215                 220

Thr Ser Val Ser Gln Leu Leu Leu Phe Val Phe Ala Thr Phe Asn Glu
225                 230                 235                 240

Ile Ser Thr Leu Leu Ile Ile Leu Leu Ser Tyr Val Leu Ile Val Val
                245                 250                 255

Thr Ile Leu Lys Met Lys Ser Ala Ser Gly Arg Arg Lys Ala Phe Ser
            260                 265                 270

Thr Cys Ala Ser His Leu Thr Ala Ile Thr Ile Phe His Gly Thr Ile
        275                 280                 285

Leu Phe Leu Tyr Cys Val Pro Asn Ser Lys Asn Ser Arg His Thr Val
    290                 295                 300

Lys Val Ala Ser Val Phe Tyr Thr Val Val Ile Pro Met Leu Asn Pro
305                 310                 315                 320

Leu Ile Tyr Ser Leu Arg Asn Lys Asp Phe Arg Lys Ala Phe Gln Arg

```
                    325                 330                 335
Leu Leu Cys Cys Ala Arg Arg Ala Ala Cys Arg Arg Ala Ala His
                340                 345                 350
Gly Asp Arg Pro Arg Ala Ser Gly Cys Leu Ala Arg Ala Gly Pro Pro
                355                 360                 365
Pro Ser Pro Gly Ala Pro Ser Asp Asp Asp Asp Asp Ala Gly Ala
370                 375                 380
Thr Pro Pro Ala Arg Leu Leu Glu Pro Trp Ala Gly Cys Asn Gly Gly
385                 390                 395                 400
Thr Thr Thr Val Asp Ser Asp Ser Ser Leu Asp Glu Pro Gly Arg Gln
                405                 410                 415
Gly Phe Ser Ser Glu Ser Lys Val
                420

<210> SEQ ID NO 37
<211> LENGTH: 433
<212> TYPE: PRT
<213> ORGANISM: Artificial
<220> FEATURE:
<223> OTHER INFORMATION: chimera 2

<400> SEQUENCE: 37

Met Gly Ala Gly Ala Leu Ala Leu Gly Ala Ser Glu Pro Cys Asn Leu
1               5                   10                  15
Ser Ser Ala Ala Pro Leu Pro Asp Gly Ala Ala Thr Ala Ala Arg Leu
                20                  25                  30
Leu Val Leu Ala Ser Pro Pro Ala Ser Leu Leu Pro Pro Ala Ser Glu
            35                  40                  45
Gly Ser Ala Pro Leu Ser Gln Gln Trp Thr Ala Gly Met Gly Leu Leu
        50                  55                  60
Leu Ala Leu Ile Val Leu Leu Ile Val Val Gly Asn Val Leu Val Ile
65                  70                  75                  80
Val Ala Ile Ala Lys Thr Pro Arg Leu Gln Thr Leu Thr Asn Leu Thr
                85                  90                  95
Arg Pro Met Tyr Phe Phe Leu Ser His Leu Ser Phe Val Asp Phe Cys
                100                 105                 110
Tyr Ser Ser Ile Val Ala Pro Lys Met Leu Val Asn Leu Val Thr Met
            115                 120                 125
Asn Arg Gly Ile Ser Phe Val Gly Cys Leu Val Gln Phe Phe Phe Phe
        130                 135                 140
Cys Thr Phe Val Val Thr Glu Ser Phe Leu Leu Gly Val Met Ala Tyr
145                 150                 155                 160
Asp Arg Phe Val Ala Ile Arg Asn Pro Leu Leu Tyr Thr Val Ala Met
                165                 170                 175
Ser Gln Arg Leu Cys Ala Met Leu Val Leu Gly Ser Tyr Ala Trp Gly
                180                 185                 190
Val Val Cys Ser Leu Ile Leu Thr Cys Ser Ala Leu Asn Leu Ser Phe
            195                 200                 205
Tyr Gly Phe Asn Met Ile Asn His Phe Phe Cys Glu Phe Ser Ser Leu
        210                 215                 220
Leu Ser Leu Ser Arg Ser Asp Thr Ser Val Ser Gln Leu Leu Leu Phe
225                 230                 235                 240
Val Phe Ala Thr Phe Asn Glu Ile Ser Thr Leu Leu Ile Ile Leu Leu
                245                 250                 255
Ser Tyr Val Leu Ile Val Val Thr Ile Leu Lys Met Lys Ser Ala Ser
```

```
                260                 265                 270
Gly Arg Arg Lys Ala Phe Ser Thr Cys Ala Ser His Leu Thr Ala Ile
            275                 280                 285

Thr Ile Phe His Gly Thr Ile Leu Phe Leu Tyr Cys Val Pro Asn Ser
        290                 295                 300

Lys Asn Ser Arg His Thr Val Lys Val Ala Ser Val Phe Tyr Thr Val
305                 310                 315                 320

Val Ile Pro Met Leu Asn Pro Leu Ile Tyr Ser Leu Arg Asn Lys Ser
                325                 330                 335

Arg Asp Phe Arg Lys Ala Phe Gln Arg Leu Leu Cys Cys Ala Arg Arg
            340                 345                 350

Ala Ala Cys Arg Arg Arg Ala Ala His Gly Asp Arg Pro Arg Ala Ser
            355                 360                 365

Gly Cys Leu Ala Arg Ala Gly Pro Pro Ser Pro Gly Ala Pro Ser
        370                 375                 380

Asp Asp Asp Asp Asp Ala Gly Ala Thr Pro Pro Ala Arg Leu Leu
385                 390                 395                 400

Glu Pro Trp Ala Gly Cys Asn Gly Gly Thr Thr Val Asp Ser Asp
                405                 410                 415

Ser Ser Leu Asp Glu Pro Gly Arg Gln Gly Phe Ser Ser Glu Ser Lys
            420                 425                 430

Val

<210> SEQ ID NO 38
<211> LENGTH: 465
<212> TYPE: PRT
<213> ORGANISM: Artificial
<220> FEATURE:
<223> OTHER INFORMATION: chimera 3

<400> SEQUENCE: 38

Met Asn Gly Thr Glu Gly Pro Asn Phe Tyr Val Pro Phe Ser Asn Lys
1               5                   10                  15

Thr Gly Val Val Glu Gln Lys Leu Ile Ser Glu Glu Asp Leu Glu Phe
            20                  25                  30

Met Gly Ala Gly Ala Leu Ala Leu Gly Ala Ser Glu Pro Cys Asn Leu
        35                  40                  45

Ser Ser Ala Ala Pro Leu Pro Asp Gly Ala Ala Thr Ala Ala Arg Leu
    50                  55                  60

Leu Val Leu Ala Ser Pro Pro Ala Ser Leu Leu Pro Pro Ala Ser Glu
65                  70                  75                  80

Gly Ser Ala Pro Leu Ser Gln Gln Trp Thr Ala Gly Met Gly Leu Leu
                85                  90                  95

Leu Ala Leu Ile Val Leu Leu Ile Val Val Gly Asn Val Leu Val Ile
            100                 105                 110

Val Ala Ile Ala Lys Thr Pro Arg Leu Gln Thr Leu Thr Asn Leu Thr
        115                 120                 125

Arg Pro Met Tyr Phe Phe Leu Ser His Leu Ser Phe Val Asp Phe Cys
    130                 135                 140

Tyr Ser Ser Ile Val Ala Pro Lys Met Leu Val Asn Leu Val Thr Met
145                 150                 155                 160

Asn Arg Gly Ile Ser Phe Val Gly Cys Leu Val Gln Phe Phe Phe Phe
                165                 170                 175

Cys Thr Phe Val Val Thr Glu Ser Phe Leu Leu Gly Val Met Ala Tyr
            180                 185                 190
```

```
Asp Arg Phe Val Ala Ile Arg Asn Pro Leu Leu Tyr Thr Val Ala Met
            195                 200                 205

Ser Gln Arg Leu Cys Ala Met Leu Val Leu Gly Ser Tyr Ala Trp Gly
210                 215                 220

Val Val Cys Ser Leu Ile Leu Thr Cys Ser Ala Leu Asn Leu Ser Phe
225                 230                 235                 240

Tyr Gly Phe Asn Met Ile Asn His Phe Phe Cys Glu Phe Ser Ser Leu
                245                 250                 255

Leu Ser Leu Ser Arg Ser Asp Thr Ser Val Ser Gln Leu Leu Leu Phe
                260                 265                 270

Val Phe Ala Thr Phe Asn Glu Ile Ser Thr Leu Leu Ile Ile Leu Leu
                275                 280                 285

Ser Tyr Val Leu Ile Val Val Thr Ile Leu Lys Met Lys Ser Ala Ser
            290                 295                 300

Gly Arg Arg Lys Ala Phe Ser Thr Cys Ala Ser His Leu Thr Ala Ile
305                 310                 315                 320

Thr Ile Phe His Gly Thr Ile Leu Phe Leu Tyr Cys Val Pro Asn Ser
                325                 330                 335

Lys Asn Ser Arg His Thr Val Lys Val Ala Ser Val Phe Tyr Thr Val
                340                 345                 350

Val Ile Pro Met Leu Asn Pro Leu Ile Tyr Ser Leu Arg Asn Lys Ser
            355                 360                 365

Arg Asp Phe Arg Lys Ala Phe Gln Arg Leu Cys Cys Ala Arg Arg
370                 375                 380

Ala Ala Cys Arg Arg Arg Ala Ala His Gly Asp Arg Pro Arg Ala Ser
385                 390                 395                 400

Gly Cys Leu Ala Arg Ala Gly Pro Pro Ser Pro Gly Ala Pro Ser
                405                 410                 415

Asp Asp Asp Asp Asp Ala Gly Ala Thr Pro Pro Ala Arg Leu Leu
                420                 425                 430

Glu Pro Trp Ala Gly Cys Asn Gly Gly Thr Thr Val Asp Ser Asp
            435                 440                 445

Ser Ser Leu Asp Glu Pro Gly Arg Gln Gly Phe Ser Ser Glu Ser Lys
            450                 455                 460

Val
465

<210> SEQ ID NO 39
<211> LENGTH: 426
<212> TYPE: PRT
<213> ORGANISM: Artificial
<220> FEATURE:
<223> OTHER INFORMATION: chimera TM7

<400> SEQUENCE: 39

Met Asn Gly Thr Glu Gly Pro Asn Phe Tyr Val Pro Phe Ser Asn Lys
1               5                   10                  15

Thr Gly Val Val Glu Gln Lys Leu Ile Ser Glu Glu Asp Leu Glu Phe
                20                  25                  30

Met Thr Leu Ser Asp Gly Asn His Ser Gly Ala Val Phe Thr Leu Leu
            35                  40                  45

Gly Phe Ser Asp Tyr Pro Glu Leu Thr Ile Pro Leu Phe Leu Ile Phe
        50                  55                  60

Leu Thr Ile Tyr Ser Ile Thr Val Val Gly Asn Ile Gly Met Ile Val
65                  70                  75                  80
```

```
Ile Ile Arg Ile Asn Pro Lys Leu His Ile Pro Met Tyr Phe Phe Leu
                85                  90                  95

Ser His Leu Ser Phe Val Asp Phe Cys Tyr Ser Ser Ile Val Ala Pro
            100                 105                 110

Lys Met Leu Val Asn Leu Val Thr Met Asn Arg Gly Ile Ser Phe Val
        115                 120                 125

Gly Cys Leu Val Gln Phe Phe Phe Cys Thr Phe Val Val Thr Glu
    130                 135                 140

Ser Phe Leu Leu Gly Val Met Ala Tyr Asp Arg Phe Val Ala Ile Arg
145                 150                 155                 160

Asn Pro Leu Leu Tyr Thr Val Ala Met Ser Gln Arg Leu Cys Ala Met
                165                 170                 175

Leu Val Leu Gly Ser Tyr Ala Trp Gly Val Val Cys Ser Leu Ile Leu
            180                 185                 190

Thr Cys Ser Ala Leu Asn Leu Ser Phe Tyr Gly Phe Asn Met Ile Asn
        195                 200                 205

His Phe Phe Cys Glu Phe Ser Ser Leu Leu Ser Leu Ser Arg Ser Asp
    210                 215                 220

Thr Ser Val Ser Gln Leu Leu Phe Val Phe Ala Thr Phe Asn Glu
225                 230                 235                 240

Ile Ser Thr Leu Leu Ile Ile Leu Leu Ser Tyr Val Leu Ile Val Val
                245                 250                 255

Thr Ile Leu Lys Met Lys Ser Ala Ser Gly Arg Arg Lys Ala Phe Ser
            260                 265                 270

Thr Cys Ala Ser His Leu Thr Ala Ile Thr Ile Phe His Gly Thr Ile
        275                 280                 285

Leu Phe Leu Tyr Cys Val Pro Asn Ser Lys Asn Ser Arg His Thr Pro
    290                 295                 300

Asp Arg Leu Phe Val Phe Asn Trp Leu Gly Tyr Ala Asn Ser Ala
305                 310                 315                 320

Phe Asn Pro Ile Ile Tyr Cys Arg Ser Pro Asp Phe Arg Lys Ala Phe
                325                 330                 335

Gln Arg Leu Leu Cys Cys Ala Arg Ala Ala Cys Arg Arg Ala
            340                 345                 350

Ala His Gly Asp Arg Pro Arg Ala Ser Gly Cys Leu Ala Arg Ala Gly
        355                 360                 365

Pro Pro Pro Ser Pro Gly Ala Pro Ser Asp Asp Asp Asp Asp Ala
    370                 375                 380

Gly Ala Thr Pro Pro Ala Arg Leu Leu Glu Pro Trp Ala Gly Cys Asn
385                 390                 395                 400

Gly Gly Thr Thr Thr Val Asp Ser Asp Ser Ser Leu Asp Glu Pro Gly
                405                 410                 415

Arg Gln Gly Phe Ser Ser Glu Ser Lys Val
            420                 425

<210> SEQ ID NO 40
<211> LENGTH: 391
<212> TYPE: PRT
<213> ORGANISM: Artificial
<220> FEATURE:
<223> OTHER INFORMATION: chimera IC3

<400> SEQUENCE: 40

Met Asn Gly Thr Glu Gly Pro Asn Phe Tyr Val Pro Phe Ser Asn Lys
1               5                   10                  15
```

```
Thr Gly Val Val Glu Gln Lys Leu Ile Ser Glu Glu Asp Leu Glu Phe
            20                  25                  30

Met Thr Leu Ser Asp Gly Asn His Ser Gly Ala Val Phe Thr Leu Leu
        35                  40                  45

Gly Phe Ser Asp Tyr Pro Glu Leu Thr Ile Pro Leu Phe Leu Ile Phe
    50                  55                  60

Leu Thr Ile Tyr Ser Ile Thr Val Val Gly Asn Ile Gly Met Ile Val
65                  70                  75                  80

Ile Ile Arg Ile Asn Pro Lys Leu His Ile Pro Met Tyr Phe Phe Leu
                85                  90                  95

Ser His Leu Ser Phe Val Asp Phe Cys Tyr Ser Ser Ile Val Ala Pro
            100                 105                 110

Lys Met Leu Val Asn Leu Val Thr Met Asn Arg Gly Ile Ser Phe Val
        115                 120                 125

Gly Cys Leu Val Gln Phe Phe Phe Cys Thr Phe Val Val Thr Glu
    130                 135                 140

Ser Phe Leu Leu Gly Val Met Ala Tyr Asp Arg Phe Val Ala Ile Arg
145                 150                 155                 160

Asn Pro Leu Leu Tyr Thr Val Ala Met Ser Gln Arg Leu Cys Ala Met
                165                 170                 175

Leu Val Leu Gly Ser Tyr Ala Trp Gly Val Val Cys Ser Leu Ile Leu
            180                 185                 190

Thr Cys Ser Ala Leu Asn Leu Ser Phe Tyr Gly Phe Asn Met Ile Asn
        195                 200                 205

His Phe Phe Cys Glu Phe Ser Ser Leu Leu Ser Leu Ser Arg Ser Asp
    210                 215                 220

Thr Ser Val Ser Gln Leu Leu Leu Phe Val Phe Ala Thr Phe Asn Glu
225                 230                 235                 240

Ile Ser Thr Leu Leu Ile Ile Leu Leu Ser Tyr Val Phe Arg Glu Ala
                245                 250                 255

Gln Lys Gln Val Lys Lys Ile Asp Ser Cys Glu Arg Arg Phe Leu Ser
            260                 265                 270

Gly Pro Pro Arg Pro Pro Ser Pro Ala Pro Ser Pro Ser Pro Gly Pro
        275                 280                 285

Pro Arg Pro Ala Asp Ser Leu Ala Asn Gly Arg Ser Ser Lys Arg Arg
290                 295                 300

Pro Ser Arg Leu Val Ala Leu Arg Glu Gln Lys Ala Phe Ser Thr Cys
305                 310                 315                 320

Ala Ser His Leu Thr Ala Ile Thr Ile Phe His Gly Thr Ile Leu Phe
                325                 330                 335

Leu Tyr Cys Val Pro Asn Ser Lys Asn Ser Arg His Thr Val Lys Val
            340                 345                 350

Ala Ser Val Phe Tyr Thr Val Val Ile Pro Met Leu Asn Pro Leu Ile
        355                 360                 365

Tyr Ser Leu Arg Asn Lys Asp Val Lys Asp Thr Val Lys Lys Ile Ile
            370                 375                 380

Gly Thr Lys Val Tyr Ser Ser
385                 390

<210> SEQ ID NO 41
<211> LENGTH: 470
<212> TYPE: PRT
<213> ORGANISM: Artificial
<220> FEATURE:
```

<223> OTHER INFORMATION: chimera IC3-IC4

<400> SEQUENCE: 41

```
Met Asn Gly Thr Glu Gly Pro Asn Phe Tyr Val Pro Phe Ser Asn Lys
1               5                   10                  15

Thr Gly Val Val Glu Gln Lys Leu Ile Ser Glu Glu Asp Leu Glu Phe
            20                  25                  30

Met Thr Leu Ser Asp Gly Asn His Ser Gly Ala Val Phe Thr Leu Leu
        35                  40                  45

Gly Phe Ser Asp Tyr Pro Glu Leu Thr Ile Pro Leu Phe Leu Ile Phe
    50                  55                  60

Leu Thr Ile Tyr Ser Ile Thr Val Val Gly Asn Ile Gly Met Ile Val
65                  70                  75                  80

Ile Ile Arg Ile Asn Pro Lys Leu His Ile Pro Met Tyr Phe Phe Leu
                85                  90                  95

Ser His Leu Ser Phe Val Asp Phe Cys Tyr Ser Ser Ile Val Ala Pro
            100                 105                 110

Lys Met Leu Val Asn Leu Val Thr Met Asn Arg Gly Ile Ser Phe Val
        115                 120                 125

Gly Cys Leu Val Gln Phe Phe Phe Cys Thr Phe Val Val Thr Glu
    130                 135                 140

Ser Phe Leu Leu Gly Val Met Ala Tyr Asp Arg Phe Val Ala Ile Arg
145                 150                 155                 160

Asn Pro Leu Leu Tyr Thr Val Ala Met Ser Gln Arg Leu Cys Ala Met
                165                 170                 175

Leu Val Leu Gly Ser Tyr Ala Trp Gly Val Val Cys Ser Leu Ile Leu
            180                 185                 190

Thr Cys Ser Ala Leu Asn Leu Ser Phe Tyr Gly Phe Asn Met Ile Asn
        195                 200                 205

His Phe Phe Cys Glu Phe Ser Ser Leu Leu Ser Leu Ser Arg Ser Asp
    210                 215                 220

Thr Ser Val Ser Gln Leu Leu Leu Phe Val Phe Ala Thr Phe Asn Glu
225                 230                 235                 240

Ile Ser Thr Leu Leu Ile Ile Leu Leu Ser Tyr Val Phe Arg Glu Ala
                245                 250                 255

Gln Lys Gln Val Lys Lys Ile Asp Ser Cys Glu Arg Arg Phe Leu Ser
            260                 265                 270

Gly Pro Pro Arg Pro Pro Ser Pro Ala Pro Ser Pro Ser Pro Gly Pro
        275                 280                 285

Pro Arg Pro Ala Asp Ser Leu Ala Asn Gly Arg Ser Ser Lys Arg Arg
    290                 295                 300

Pro Ser Arg Leu Val Ala Leu Arg Glu Gln Lys Ala Phe Ser Thr Cys
305                 310                 315                 320

Ala Ser His Leu Thr Ala Ile Thr Ile Phe His Gly Thr Ile Leu Phe
                325                 330                 335

Leu Tyr Cys Val Pro Asn Ser Lys Asn Ser Arg His Thr Val Lys Val
            340                 345                 350

Ala Ser Val Phe Tyr Thr Val Val Ile Pro Met Leu Asn Pro Leu Ile
        355                 360                 365

Tyr Ser Leu Arg Asn Lys Asp Phe Arg Lys Ala Phe Gln Arg Leu Leu
    370                 375                 380

Cys Cys Ala Arg Arg Ala Ala Cys Arg Arg Ala Ala His Gly Asp
385                 390                 395                 400
```

```
Arg Pro Arg Ala Ser Gly Cys Leu Ala Arg Ala Gly Pro Pro Ser
            405                 410                 415

Pro Gly Ala Pro Ser Asp Asp Asp Asp Ala Gly Ala Thr Pro
        420                 425                 430

Pro Ala Arg Leu Leu Glu Pro Trp Ala Gly Cys Asn Gly Thr Thr
            435                 440                 445

Thr Val Asp Ser Asp Ser Ser Leu Asp Glu Pro Gly Arg Gln Gly Phe
    450                 455                 460

Ser Ser Glu Ser Lys Val
465                 470

<210> SEQ ID NO 42
<211> LENGTH: 227
<212> TYPE: PRT
<213> ORGANISM: Mus musculus

<400> SEQUENCE: 42

Met Cys Lys Ser Val Thr Thr Gly Glu Trp Lys Lys Val Phe Tyr Glu
1               5                   10                  15

Lys Met Glu Glu Val Lys Pro Ala Asp Ser Trp Asp Phe Ile Ile Asp
            20                  25                  30

Pro Asn Leu Lys His Asn Val Leu Ala Pro Gly Trp Lys Gln Tyr Leu
        35                  40                  45

Glu Leu His Ala Ser Gly Arg Phe His Cys Ser Trp Cys Trp His Thr
    50                  55                  60

Trp Gln Ser Pro His Val Val Ile Leu Phe His Met Tyr Leu Asp Lys
65                  70                  75                  80

Ala Gln Arg Ala Gly Ser Val Arg Met Arg Val Phe Lys Gln Leu Cys
                85                  90                  95

Tyr Glu Cys Gly Thr Ala Arg Leu Asp Glu Ser Ser Met Leu Glu Glu
            100                 105                 110

Asn Ile Glu Ser Leu Val Asp Asn Leu Ile Thr Ser Leu Arg Glu Gln
        115                 120                 125

Cys Tyr Gly Glu Arg Gly Gly His Tyr Arg Ile His Val Ala Ser Arg
    130                 135                 140

Gln Asp Asn Arg Arg His Arg Gly Glu Phe Cys Glu Ala Cys Gln Glu
145                 150                 155                 160

Gly Ile Val His Trp Lys Pro Ser Glu Lys Leu Leu Glu Glu Ala
                165                 170                 175

Thr Thr Tyr Thr Phe Ser Arg Ala Pro Ser Pro Thr Lys Pro Gln Ala
            180                 185                 190

Glu Thr Gly Ser Gly Cys Asn Phe Cys Ser Ile Pro Trp Cys Leu Phe
        195                 200                 205

Trp Ala Thr Val Leu Met Leu Ile Ile Tyr Leu Gln Phe Ser Phe Arg
    210                 215                 220

Thr Ser Val
225

<210> SEQ ID NO 43
<211> LENGTH: 312
<212> TYPE: PRT
<213> ORGANISM: Mus musculus

<400> SEQUENCE: 43

Met Glu Lys Trp Asn Gln Ser Ser Ser Asp Phe Ile Leu Leu Gly Leu
1               5                   10                  15
```

Leu Pro Gln Asn Gln Thr Gly Leu Leu Leu Met Met Leu Ile Ile Leu
            20                  25                  30

Val Phe Phe Leu Ala Leu Phe Gly Asn Ser Ala Met Ile His Leu Ile
        35                  40                  45

Arg Val Asp Pro Arg Leu His Thr Pro Met Tyr Phe Leu Leu Ser Gln
50                  55                  60

Leu Ser Leu Met Asp Leu Met Tyr Ile Ser Thr Val Pro Lys Met
65                  70                  75                  80

Ala Phe Asn Phe Leu Ser Gly Gln Lys Asn Ile Ser Phe Leu Gly Cys
                85                  90                  95

Gly Val Gln Ser Phe Phe Phe Leu Thr Met Ala Gly Ser Glu Gly Leu
            100                 105                 110

Leu Leu Ala Ser Met Ala Tyr Asp Arg Phe Val Ala Ile Cys His Pro
        115                 120                 125

Leu His Tyr Pro Ile Arg Met Ser Lys Ile Met Cys Leu Lys Met Ile
    130                 135                 140

Ile Gly Ser Trp Ile Leu Gly Ser Ile Asn Ser Leu Ala His Ser Ile
145                 150                 155                 160

Tyr Ala Leu His Ile Pro Tyr Cys His Ser Arg Ser Ile Asn His Phe
                165                 170                 175

Phe Cys Asp Val Pro Ala Met Leu Pro Leu Ala Cys Met Asp Thr Trp
            180                 185                 190

Val Tyr Glu Tyr Met Val Phe Val Ser Thr Ser Leu Phe Leu Leu Leu
        195                 200                 205

Pro Phe Leu Gly Ile Thr Ala Ser Tyr Gly Arg Val Leu Phe Ala Val
    210                 215                 220

Phe His Met Arg Ser Lys Glu Gly Lys Lys Ala Phe Thr Thr Cys
225                 230                 235                 240

Ser Thr His Leu Thr Val Val Thr Phe Tyr Tyr Ala Pro Phe Val Tyr
                245                 250                 255

Thr Tyr Leu Arg Pro Arg Ser Leu Arg Ser Pro Thr Glu Asp Lys Ile
            260                 265                 270

Leu Thr Val Phe Tyr Thr Ile Leu Thr Pro Met Leu Asn Pro Ile Ile
        275                 280                 285

Tyr Ser Leu Arg Asn Lys Glu Val Leu Gly Ala Met Thr Arg Val Leu
    290                 295                 300

Gly Thr Phe Ser Ser Met Lys Pro
305                 310

<210> SEQ ID NO 44
<211> LENGTH: 312
<212> TYPE: PRT
<213> ORGANISM: Mus musculus

<400> SEQUENCE: 44

Met Glu Val Asp Ser Asn Ser Ser Gly Ser Phe Ile Leu Met Gly
1               5                   10                  15

Val Ser Asp His Pro His Leu Glu Ile Ile Phe Phe Ala Val Ile Leu
            20                  25                  30

Ala Ser Tyr Leu Leu Thr Leu Val Gly Asn Leu Thr Ile Ile Leu Leu
        35                  40                  45

Ser Arg Leu Asp Ala Arg Leu His Thr Pro Met Tyr Phe Phe Leu Ser
    50                  55                  60

Asn Leu Ser Ser Leu Asp Leu Ala Phe Thr Thr Ser Ser Val Pro Gln
65                  70                  75                  80

Met Leu Lys Asn Leu Trp Gly Pro Asp Lys Thr Ile Ser Tyr Gly Gly
                85                  90                  95
Cys Val Thr Gln Leu Tyr Val Phe Leu Trp Leu Gly Ala Thr Glu Cys
            100                 105                 110
Ile Leu Leu Val Val Met Ala Phe Asp Arg Tyr Val Ala Val Cys Arg
        115                 120                 125
Pro Leu His Tyr Met Thr Val Met Asn Pro Arg Leu Cys Trp Gly Leu
    130                 135                 140
Ala Ala Ile Ser Trp Leu Gly Gly Leu Gly Asn Ser Val Ile Gln Ser
145                 150                 155                 160
Thr Phe Thr Leu Gln Leu Pro Phe Cys Gly His Arg Lys Val Asp Asn
                165                 170                 175
Phe Leu Cys Glu Val Pro Ala Met Ile Lys Leu Ala Cys Gly Asp Thr
            180                 185                 190
Ser Leu Asn Glu Ala Val Leu Asn Gly Val Cys Thr Phe Phe Thr Val
        195                 200                 205
Val Pro Val Ser Val Ile Leu Val Ser Tyr Cys Phe Ile Ala Gln Ala
    210                 215                 220
Val Met Lys Ile Arg Ser Val Glu Gly Arg Arg Lys Ala Phe Asn Thr
225                 230                 235                 240
Cys Val Ser His Leu Val Val Val Phe Leu Phe Tyr Gly Ser Ala Ile
                245                 250                 255
Tyr Gly Tyr Leu Leu Pro Ala Lys Ser Ser Asn Gln Ser Gln Gly Lys
            260                 265                 270
Phe Ile Ser Leu Phe Tyr Ser Val Thr Pro Met Val Asn Pro Leu
        275                 280                 285
Ile Tyr Thr Leu Arg Asn Lys Glu Val Lys Gly Ala Leu Gly Arg Leu
    290                 295                 300
Leu Gly Lys Gly Arg Gly Ala Ser
305                 310

<210> SEQ ID NO 45
<211> LENGTH: 319
<212> TYPE: PRT
<213> ORGANISM: Mus musculus

<400> SEQUENCE: 45

Met Ser Tyr Ser Asn His Ser Ser Thr Ser Phe Phe Leu Thr Gly Leu
1               5                   10                  15
Pro Gly Leu Glu Thr Val Tyr Leu Trp Leu Ser Ile Pro Leu Cys Thr
            20                  25                  30
Met Tyr Ile Ala Ser Leu Ala Gly Asn Gly Leu Ile Leu Trp Val Val
        35                  40                  45
Lys Ser Glu Pro Ser Leu His Gln Pro Met Tyr Tyr Phe Leu Ser Met
    50                  55                  60
Leu Ala Val Thr Asp Leu Gly Leu Ser Val Ser Thr Leu Pro Thr Met
65                  70                  75                  80
Leu Thr Ile Tyr Met Met Gly Val Ser Glu Val Ala Leu Asp Met Cys
                85                  90                  95
Leu Ala Gln Leu Phe Phe Ile His Thr Phe Ser Ile Met Glu Ser Ser
            100                 105                 110
Val Leu Leu Thr Met Ala Phe Asp Arg Val Val Ala Ile Ser Ser Pro
        115                 120                 125
Leu His Tyr Ala Thr Ile Leu Thr Asn Pro Arg Val Ala Ser Leu Gly

```
                130             135             140
Met Val Ile Leu Val Arg Ser Ile Gly Leu His Ile Pro Ala Pro Ile
145                 150                 155                 160

Met Leu Lys Lys Leu Pro Tyr Cys Gln Lys Arg His Leu Ser His Ser
                165                 170                 175

Tyr Cys Leu His Pro Asp Val Met Lys Leu Ala Cys Thr Asp Thr Arg
                180                 185                 190

Ile Asn Ser Ala Tyr Gly Leu Phe Val Val Leu Ser Thr Leu Gly Val
                195                 200                 205

Asp Ser Val Leu Ile Val Leu Ser Tyr Gly Leu Ile Leu Tyr Thr Val
210                 215                 220

Leu Ser Ile Ala Ser Lys Thr Glu Arg Leu Lys Ala Leu Asn Thr Cys
225                 230                 235                 240

Val Ser His Ile Cys Ser Val Leu Leu Phe Tyr Thr Pro Met Ile Gly
                245                 250                 255

Leu Ser Met Ile His Arg Phe Gly Lys Trp Ala Ser Pro Cys Ser Arg
                260                 265                 270

Val Leu Leu Ser Tyr Leu His Phe Leu Thr Pro Pro Val Leu Asn Pro
                275                 280                 285

Val Val Tyr Thr Ile Lys Thr Lys Gln Ile Arg Gln Arg Ile Trp Arg
290                 295                 300

Ile Phe Arg Cys Gly Gly Arg Ser Ile Gly His Ile Gln Gly His
305                 310                 315

<210> SEQ ID NO 46
<211> LENGTH: 44
<212> TYPE: DNA
<213> ORGANISM: Artificial Sequence
<220> FEATURE:
<223> OTHER INFORMATION: primer for preparing a plasmid expressing
      Rho-myc-Olfr168

<400> SEQUENCE: 46
agaggatctg gaattcatgg agaaatggaa tcagagttca agtg                  44

<210> SEQ ID NO 47
<211> LENGTH: 39
<212> TYPE: DNA
<213> ORGANISM: Artificial Sequence
<220> FEATURE:
<223> OTHER INFORMATION: primer for preparing a plasmid expressing
      Rho-myc-Olfr168

<400> SEQUENCE: 47
ggccgcccgg gtcgactcat ggtttcatgg aagagaatg                        39

<210> SEQ ID NO 48
<211> LENGTH: 939
<212> TYPE: DNA
<213> ORGANISM: Mus musculus

<400> SEQUENCE: 48
atggagaaat ggaatcagag ttcaagtgat tcattctct tagggttgct tccacaaaac    60
caaactggcc tactactat gatgctcatc atacttgtct ctttctggc cttgtttgga   120 aactcagcaa tgatccacct cattcgtgtg atccaaggc tccacacccc catgtacttt   180
ctcctcagtc agctctctct catggacctg atgtacattt ctaccactgt tcccaagatg   240
gcatttaact tcctttctgg ccagaaaaac atctctttc tgggctgtgg tgtgcagtct   300
```

-continued

```
tttttcttttt tgaccatggc aggttctgag ggcttgctct tggcttccat ggcttatgat    360
cgttttgtgg ctatctgcca tccccttcac tatcccattc gcatgagcaa gataatgtgt    420
ctgaagatga tcataggatc ctggatattg ggctcaatca actctttagc acattccatc    480
tatgcccttc atattcctta ctgccattct aggtccatta accatttctt ctgtgatgtt    540
ccagccatgt tgcccctggc ctgtatggac acttgggttt atgagtacat ggtgtttgtg    600
agcacaagcc tgtttctcct actgcctttc cttggtatca cagcttccta tggtagggtc    660 cttttttgctg tcttccacat gcgctcaaaa gagggaaaga agaaggcctt caccacatgc    720
tcaactcact taactgtggt gacattttac tatgcacctt ttgtctatac ctatcttcga    780
cctaggagtc ttcgctcccc aacagaagat aagattctga ctgttttcta cactatcctt    840
acccccatgc tcaaccccat catctatagt ctgaggaata aggaggtcct gggggccatg    900
acaagagtcc ttgggacatt ctcttccatg aaaccatga                          939
```

<210> SEQ ID NO 49
<211> LENGTH: 344
<212> TYPE: PRT
<213> ORGANISM: Artificial Sequence
<220> FEATURE:
<223> OTHER INFORMATION: Rho-myc-olfr168

<400> SEQUENCE: 49

```
Met Asn Gly Thr Glu Gly Pro Asn Phe Tyr Val Pro Phe Ser Asn Lys
1               5                   10                  15

Thr Gly Val Val Glu Gln Lys Leu Ile Ser Glu Glu Asp Leu Glu Phe
            20                  25                  30

Met Glu Lys Trp Asn Gln Ser Ser Asp Phe Ile Leu Leu Gly Leu
        35                  40                  45

Leu Pro Gln Asn Gln Thr Gly Leu Leu Leu Met Met Leu Ile Ile Leu
    50                  55                  60

Val Phe Phe Leu Ala Leu Phe Gly Asn Ser Ala Met Ile His Leu Ile
65                  70                  75                  80

Arg Val Asp Pro Arg Leu His Thr Pro Met Tyr Phe Leu Leu Ser Gln
                85                  90                  95

Leu Ser Leu Met Asp Leu Met Tyr Ile Ser Thr Thr Val Pro Lys Met
            100                 105                 110

Ala Phe Asn Phe Leu Ser Gly Gln Lys Asn Ile Ser Phe Leu Gly Cys
        115                 120                 125

Gly Val Gln Ser Phe Phe Phe Leu Thr Met Ala Gly Ser Glu Gly Leu
    130                 135                 140

Leu Leu Ala Ser Met Ala Tyr Asp Arg Phe Val Ala Ile Cys His Pro
145                 150                 155                 160

Leu His Tyr Pro Ile Arg Met Ser Lys Ile Met Cys Leu Lys Met Ile
                165                 170                 175

Ile Gly Ser Trp Ile Leu Gly Ser Ile Asn Ser Leu Ala His Ser Ile
            180                 185                 190

Tyr Ala Leu His Ile Pro Tyr Cys His Ser Arg Ser Ile Asn His Phe
        195                 200                 205

Phe Cys Asp Val Pro Ala Met Leu Pro Leu Ala Cys Met Asp Thr Trp
    210                 215                 220

Val Tyr Glu Tyr Met Val Phe Val Ser Thr Ser Leu Phe Leu Leu Leu
225                 230                 235                 240

Pro Phe Leu Gly Ile Thr Ala Ser Tyr Gly Arg Val Leu Phe Ala Val
                245                 250                 255
```

Phe His Met Arg Ser Lys Glu Gly Lys Lys Ala Phe Thr Thr Cys
        260                 265                 270

Ser Thr His Leu Thr Val Val Thr Phe Tyr Tyr Ala Pro Phe Val Tyr
            275                 280                 285

Thr Tyr Leu Arg Pro Arg Ser Leu Arg Ser Pro Thr Glu Asp Lys Ile
        290                 295                 300

Leu Thr Val Phe Tyr Thr Ile Leu Thr Pro Met Leu Asn Pro Ile Ile
305                 310                 315                 320

Tyr Ser Leu Arg Asn Lys Glu Val Leu Gly Ala Met Thr Arg Val Leu
                325                 330                 335

Gly Thr Phe Ser Ser Met Lys Pro
            340

<210> SEQ ID NO 50
<211> LENGTH: 1173
<212> TYPE: DNA
<213> ORGANISM: Artificial Sequence
<220> FEATURE:
<223> OTHER INFORMATION: Fragment for preparing ChimeraOlfr168

<400> SEQUENCE: 50

| | | | | | |
|---|---|---|---|---|---|
| atggagaaat | ggaatcagag | ttcaagtgat | tcattctct | tagggttgct | tccacaaaac | 60 |
| caaactggcc | tactacttat | gatgctcatc | atacttgtct | tctttctggc | cttgtttgga | 120 |
| aactcagcaa | tgatccacct | cattcgtgtg | gatccaaggc | tccacacccc | catgtacttt | 180 |
| ctcctcagtc | agctctctct | catggacctg | atgtacattt | ctaccactgt | tcccaagatg | 240 |
| gcatttaact | tcctttctgg | ccagaaaaac | atctctttc | tgggctgtgg | tgtgcagtct | 300 |
| tttttctttt | tgaccatggc | aggttctgag | ggcttgctct | tggcttccat | ggcttatgat | 360 |
| cgttttgtgg | ctatctgcca | tccccttcac | tatcccattc | gcatgagcaa | gataatgtgt | 420 |
| ctgaagatga | tcataggatc | ctggatattg | ggctcaatca | actctttagc | acattccatc | 480 |
| tatgcccttc | atattcctta | ctgccattct | aggtccatta | accatttctt | ctgtgatgtt | 540 |
| ccagccatgt | tgcccctggc | ctgtatggac | acttgggttt | atgagtacat | ggtgtttgtg | 600 |
| agcacaagcc | tgtttctcct | actgcctttc | cttggtatca | cagcttccta | tggtagggtc | 660 |
| cttttttgctg | tcttccacat | gcgctcaaaa | gagggaaaga | agaaggcctt | caccacatgc | 720 |
| tcaactcact | taactgtggt | gacatttttac | tatgcacctt | ttgtctatac | ctatcttcga | 780 |
| cctaggagtc | ttcgctcccc | aacagaagat | aagattctga | ctgttttcta | cactatcctt | 840 |
| accccccatgc | tcaaccccat | catctatagt | ctgaggaata | aggacttccg | caaggctttc | 900 |
| cagcgcctgc | tttgctgcgc | gcgccgggcc | gcctgcagac | gccgcgcagc | ccacggggac | 960 |
| cggccgcgcg | cctcgggctg | cctggcgaga | gctgggccgc | cgccgtcccc | cggggctcct | 1020 |
| tcggacgacg | acgacgatga | cgccggggcc | accccacccg | cgcgcctgtt | ggagccctgg | 1080 |
| gccggctgca | acggcgggac | gaccactgtg | gacagcgatt | cgagcctgga | cgagccggga | 1140 |
| cgccagggct | tctcctccga | gtccaaggtg | tag | | | 1173 |

<210> SEQ ID NO 51
<211> LENGTH: 422
<212> TYPE: PRT
<213> ORGANISM: Artificial Sequence
<220> FEATURE:
<223> OTHER INFORMATION: ChimeraOlfr168

<400> SEQUENCE: 51

```
Met Asn Gly Thr Glu Gly Pro Asn Phe Tyr Val Pro Phe Ser Asn Lys
1               5                   10                  15

Thr Gly Val Val Glu Gln Lys Leu Ile Ser Glu Glu Asp Leu Glu Phe
            20                  25                  30

Met Glu Lys Trp Asn Gln Ser Ser Asp Phe Ile Leu Leu Gly Leu
        35                  40                  45

Leu Pro Gln Asn Gln Thr Gly Leu Leu Leu Met Met Leu Ile Ile Leu
50                      55                  60

Val Phe Phe Leu Ala Leu Phe Gly Asn Ser Ala Met Ile His Leu Ile
65                  70                  75                  80

Arg Val Asp Pro Arg Leu His Thr Pro Met Tyr Phe Leu Leu Ser Gln
                85                  90                  95

Leu Ser Leu Met Asp Leu Met Tyr Ile Ser Thr Val Pro Lys Met
                100                 105                 110

Ala Phe Asn Phe Leu Ser Gly Gln Lys Asn Ile Ser Phe Leu Gly Cys
            115                 120                 125

Gly Val Gln Ser Phe Phe Leu Thr Met Ala Gly Ser Glu Gly Leu
        130                 135                 140

Leu Leu Ala Ser Met Ala Tyr Asp Arg Phe Val Ala Ile Cys His Pro
145                 150                 155                 160

Leu His Tyr Pro Ile Arg Met Ser Lys Ile Met Cys Leu Lys Met Ile
                165                 170                 175

Ile Gly Ser Trp Ile Leu Gly Ser Ile Asn Ser Leu Ala His Ser Ile
            180                 185                 190

Tyr Ala Leu His Ile Pro Tyr Cys His Ser Arg Ser Ile Asn His Phe
        195                 200                 205

Phe Cys Asp Val Pro Ala Met Leu Pro Leu Ala Cys Met Asp Thr Trp
210                 215                 220

Val Tyr Glu Tyr Met Val Phe Val Ser Thr Ser Leu Phe Leu Leu Leu
225                 230                 235                 240

Pro Phe Leu Gly Ile Thr Ala Ser Tyr Gly Arg Val Leu Phe Ala Val
                245                 250                 255

Phe His Met Arg Ser Lys Glu Gly Lys Lys Lys Ala Phe Thr Thr Cys
            260                 265                 270

Ser Thr His Leu Thr Val Val Thr Phe Tyr Tyr Ala Pro Phe Val Tyr
        275                 280                 285

Thr Tyr Leu Arg Pro Arg Ser Leu Arg Ser Pro Thr Glu Asp Lys Ile
        290                 295                 300

Leu Thr Val Phe Tyr Thr Ile Leu Thr Pro Met Leu Asn Pro Ile Ile
305                 310                 315                 320

Tyr Ser Leu Arg Asn Lys Asp Phe Arg Lys Ala Phe Gln Arg Leu Leu
                325                 330                 335

Cys Cys Ala Arg Arg Ala Ala Cys Arg Arg Ala Ala His Gly Asp
            340                 345                 350

Arg Pro Arg Ala Ser Gly Cys Leu Ala Arg Ala Gly Pro Pro Ser
        355                 360                 365

Pro Gly Ala Pro Ser Asp Asp Asp Asp Asp Ala Gly Ala Thr Pro
370                 375                 380

Pro Ala Arg Leu Leu Glu Pro Trp Ala Gly Cys Asn Gly Gly Thr Thr
385                 390                 395                 400

Thr Val Asp Ser Asp Ser Ser Leu Asp Glu Pro Gly Arg Gln Gly Phe
                405                 410                 415

Ser Ser Glu Ser Lys Val
```

```
<210> SEQ ID NO 52
<211> LENGTH: 18
<212> TYPE: DNA
<213> ORGANISM: Artificial Sequence
<220> FEATURE:
<223> OTHER INFORMATION: primer for preparing a plasmid expressing
      Rho-myc-Olfr15

<400> SEQUENCE: 52
atggaggtgg acagcaac                                                         18

<210> SEQ ID NO 53
<211> LENGTH: 18
<212> TYPE: DNA
<213> ORGANISM: Artificial Sequence
<220> FEATURE:
<223> OTHER INFORMATION: primer for preparing a plasmid expressing
      Rho-myc-Olfr15

<400> SEQUENCE: 53
tcagctggct cctcttcc                                                         18

<210> SEQ ID NO 54
<211> LENGTH: 34
<212> TYPE: DNA
<213> ORGANISM: Artificial Sequence
<220> FEATURE:
<223> OTHER INFORMATION: primer for preparing a plasmid expressing
      Rho-myc-Olfr15

<400> SEQUENCE: 54
agaggatctg gaattcatgg aggtggacag caac                                       34

<210> SEQ ID NO 55
<211> LENGTH: 34
<212> TYPE: DNA
<213> ORGANISM: Artificial Sequence
<220> FEATURE:
<223> OTHER INFORMATION: primer for preparing a plasmid expressing
      Rho-myc-Olfr15

<400> SEQUENCE: 55
ggccgcccgg gtcgactcag ctggctcctc ttcc                                       34

<210> SEQ ID NO 56
<211> LENGTH: 939
<212> TYPE: DNA
<213> ORGANISM: Mus musculus

<400> SEQUENCE: 56
atggaggtgg acagcaacag ctcctctggg agcttcattc tgatgggtgt ctctgaccat           60
ccccatctgg agatcatctt ttttgctgtc atcctggcct cttacttgtt gacgctggtt          120
gggaacttga ccatcatcct gctttcgcgc cttgatgctc ggctccacac acccatgtac          180
ttcttcctca gcaacctctc ctctctagac cttgccttta ctaccagttc agtccctcag          240
atgctgaaaa attatggggg ccagacaag acaatcagct atggtgggtg tgtaactcaa           300
ctctatgttt tcctttggct gggggctact gagtgcatac tgctcgtggt gatggcattt          360
gatcggtatg tggcagtttg tcggcccctg cactacatga ccgtcatgaa tcctcgcctc          420
tgctgggggc tggctgctat tagctggttg ggtggcttag caactccgt gattcagtca           480 acattcactc tccagctccc attttgcgga caccgaaaag tggacaactt cctgtgtgag          540
```

```
gtacccgcca tgattaaatt ggcctgtgga cacacaagtc tcaatgaggc ggtgctcaat      600
ggtgtttgta ccttcttcac tgtggtccca gtaagcgtca tcctggtctc ttactgcttc      660
attgctcagg cagtgatgaa gatccgctct gtggagggac gtcgaaaggc tttcaatacg      720
tgtgtctccc acttggtggt agtgtttctc ttctatggct ctgcgatcta tgggtatctg      780
cttccagcta agagcagtaa tcaaagccaa ggaaaattca tttctctctt ctactctgtg      840
gtcacaccca tggtgaatcc gctcatctat actctaagaa acaaagaagt gaagggggcc      900
ctgggaagat tgctggggaa aggaagagga gccagctga                              939
```

<210> SEQ ID NO 57
<211> LENGTH: 1035
<212> TYPE: DNA
<213> ORGANISM: Artificial Sequence
<220> FEATURE:
<223> OTHER INFORMATION: Fragment encoding Rho-myc-Olfr168

<400> SEQUENCE: 57

```
atgaacggga ccgagggccc aaacttctac gtgccttttct ccaacaagac gggcgtcgta      60
gagcagaaac tcatctctga gaggatctg gaattcatgg agaaatggaa tcagagttca      120
agtgatttca ttctcttagg gttgcttcca caaaaccaaa ctggcctact acttatgatg      180
ctcatcatac ttgtcttctt ctggccttg tttggaaact cagcaatgat ccacctcatt      240
cgtgtggatc caaggctcca caccccatg tactttctcc tcagtcagct ctctctcatg      300
gacctgatgt acatttctac cactgttccc aagatggcat ttaacttcct ttctggccag      360
aaaaacatct ctttctgggg ctgtggtgtg cagtcttttt tcttttttgac catggcaggt      420 tctgagggct tgctcttggc ttccatggct tatgatcgtt ttgtggctat ctgccatccc      480
cttcactatc ccattcgcat gagcaagata atgtgtctga gatgatcat aggatcctgg      540 atattgggct caatcaactc tttagcacat tccatctatg ccttcatat tccttactgc      600 cattctaggt ccattaacca tttcttctgt gatgttccag ccatgttgcc cctggcctgt      660
atggacactt gggtttatga gtacatggtg tttgtgagca caagcctgtt tctcctactg      720
cctttccttg gtatcacagc ttcctatggt agggtccttt ttgctgtctt ccacatgcgc      780
tcaaaagagg gaagaagaa ggccttcacc acatgctcaa ctcacttaac tgtggtgaca      840
ttttactatg caccttttgt ctatacctat cttcgaccta ggagtcttcg ctccccaaca      900
gaagataaga ttctgactgt tttctacact atccttaccc ccatgctcaa ccccatcatc      960
tatagtctga ggaataagga ggtcctgggg gccatgacaa gagtccttgg acattctct    1020 tccatgaaac catga                                                    1035
```

<210> SEQ ID NO 58
<211> LENGTH: 344
<212> TYPE: PRT
<213> ORGANISM: Artificial Sequence
<220> FEATURE:
<223> OTHER INFORMATION: Rho-myc-Olfr15

<400> SEQUENCE: 58

Met Asn Gly Thr Glu Gly Pro Asn Phe Tyr Val Pro Phe Ser Asn Lys
1               5                   10                  15

Thr Gly Val Val Glu Gln Lys Leu Ile Ser Glu Glu Asp Leu Glu Phe
            20                  25                  30

Met Glu Val Asp Ser Asn Ser Ser Gly Ser Phe Ile Leu Met Gly
        35                  40                  45

Val Ser Asp His Pro His Leu Glu Ile Ile Phe Phe Ala Val Ile Leu
 50                  55                  60

Ala Ser Tyr Leu Leu Thr Leu Val Gly Asn Leu Thr Ile Ile Leu Leu
 65                  70                  75                  80

Ser Arg Leu Asp Ala Arg Leu His Thr Pro Met Tyr Phe Phe Leu Ser
                 85                  90                  95

Asn Leu Ser Ser Leu Asp Leu Ala Phe Thr Thr Ser Ser Val Pro Gln
            100                 105                 110

Met Leu Lys Asn Leu Trp Gly Pro Asp Lys Thr Ile Ser Tyr Gly Gly
            115                 120                 125

Cys Val Thr Gln Leu Tyr Val Phe Leu Trp Leu Gly Ala Thr Glu Cys
            130                 135                 140

Ile Leu Leu Val Val Met Ala Phe Asp Arg Tyr Val Ala Val Cys Arg
145                 150                 155                 160

Pro Leu His Tyr Met Thr Val Met Asn Pro Arg Leu Cys Trp Gly Leu
                165                 170                 175

Ala Ala Ile Ser Trp Leu Gly Gly Leu Gly Asn Ser Val Ile Gln Ser
            180                 185                 190

Thr Phe Thr Leu Gln Leu Pro Phe Cys Gly His Arg Lys Val Asp Asn
            195                 200                 205

Phe Leu Cys Glu Val Pro Ala Met Ile Lys Leu Ala Cys Gly Asp Thr
210                 215                 220

Ser Leu Asn Glu Ala Val Leu Asn Gly Val Cys Thr Phe Phe Thr Val
225                 230                 235                 240

Val Pro Val Ser Val Ile Leu Val Ser Tyr Cys Phe Ile Ala Gln Ala
                245                 250                 255

Val Met Lys Ile Arg Ser Val Glu Gly Arg Arg Lys Ala Phe Asn Thr
            260                 265                 270

Cys Val Ser His Leu Val Val Val Phe Leu Phe Tyr Gly Ser Ala Ile
            275                 280                 285

Tyr Gly Tyr Leu Leu Pro Ala Lys Ser Ser Asn Gln Ser Gln Gly Lys
            290                 295                 300

Phe Ile Ser Leu Phe Tyr Ser Val Val Thr Pro Met Val Asn Pro Leu
305                 310                 315                 320

Ile Tyr Thr Leu Arg Asn Lys Glu Val Lys Gly Ala Leu Gly Arg Leu
                325                 330                 335

Leu Gly Lys Gly Arg Gly Ala Ser
            340

<210> SEQ ID NO 59
<211> LENGTH: 1176
<212> TYPE: DNA
<213> ORGANISM: Artificial Sequence
<220> FEATURE:
<223> OTHER INFORMATION: Fragment for preparing ChimeraOlfr15

<400> SEQUENCE: 59
atggaggtgg acagcaacag ctcctctggg agcttcattc tgatgggtgt ctctgaccat      60
ccccatctgg agatcatctt ttttgctgtc atcctggcct cttacttgtt gacgctggtt     120
gggaacttga ccatcatcct gctttcgcgc cttgatgctc ggctccacac acccatgtac     180
ttcttcctca gcaacctctc ctctctagac cttgccttta ctaccagttc agtccctcag     240
atgctgaaaa atttatgggg gccagacaag acaatcagct atggtgggtg tgtaactcaa     300
ctctatgttt tcctttggct gggggctact gagtgcatac tgctcgtggt gatggcattt     360

```
gatcggtatg tggcagtttg tcggcccctg cactacatga ccgtcatgaa tcctcgcctc    420 tgctggggc tggctgctat tagctggttg ggtggcttag caactccgt gattcagtca      480 acattcactc tccagctccc attttgcgga caccgaaaag tggacaactt cctgtgtgag    540
gtacccgcca tgattaaatt ggcctgtgga cacacaagtc tcaatgaggc ggtgctcaat    600
ggtgtttgta ccttcttcac tgtggtccca gtaagcgtca tcctggtctc ttactgcttc    660
attgctcagg cagtgatgaa gatccgctct gtggagggac gtcgaaaggc tttcaatacg    720
tgtgtctccc acttggtggt agtgtttctc ttctatggct ctgcgatcta tgggtatctg    780
cttccagcta agagcagtaa tcaaagccaa ggaaaattca tttctctctt ctactctgtg    840
gtcacaccca tggtgaatcc gctcatctat actctaagaa acaaagactt ccgcaaggct    900
ttccagcgcc tgctttgctg cgcgcgccgg gccgcctgca gacgccgcgc agcccacggg    960
gaccggccgc gcgcctcggg ctgcctggcg agagctgggc cgccgccgtc ccccggggct   1020
ccttcggacg acgacgacga tgacgccggg gccaccccac ccgcgcgcct gttggagccc   1080
tgggccggct gcaacggcgg gacgaccact gtggacagcg attcgagcct ggacgagccg   1140
ggacgccagg gcttctcctc cgagtccaag gtgtag                              1176
```

<210> SEQ ID NO 60
<211> LENGTH: 423
<212> TYPE: PRT
<213> ORGANISM: Artificial Sequence
<220> FEATURE:
<223> OTHER INFORMATION: ChimeraOlfr15

<400> SEQUENCE: 60

```
Met Asn Gly Thr Glu Gly Pro Asn Phe Tyr Val Pro Phe Ser Asn Lys
1               5                   10                  15

Thr Gly Val Val Glu Gln Lys Leu Ile Ser Glu Glu Asp Leu Glu Phe
            20                  25                  30

Met Glu Val Asp Ser Asn Ser Ser Gly Ser Phe Ile Leu Met Gly
        35                  40                  45

Val Ser Asp His Pro His Leu Glu Ile Ile Phe Phe Ala Val Ile Leu
    50                  55                  60

Ala Ser Tyr Leu Leu Thr Leu Val Gly Asn Leu Thr Ile Ile Leu Leu
65                  70                  75                  80

Ser Arg Leu Asp Ala Arg Leu His Thr Pro Met Tyr Phe Phe Leu Ser
                85                  90                  95

Asn Leu Ser Ser Leu Asp Leu Ala Phe Thr Thr Ser Ser Val Pro Gln
            100                 105                 110

Met Leu Lys Asn Leu Trp Gly Pro Asp Lys Thr Ile Ser Tyr Gly Gly
        115                 120                 125

Cys Val Thr Gln Leu Tyr Val Phe Leu Trp Leu Gly Ala Thr Glu Cys
    130                 135                 140

Ile Leu Leu Val Val Met Ala Phe Asp Arg Tyr Val Ala Val Cys Arg
145                 150                 155                 160

Pro Leu His Tyr Met Thr Val Met Asn Pro Arg Leu Cys Trp Gly Leu
                165                 170                 175

Ala Ala Ile Ser Trp Leu Gly Gly Leu Gly Asn Ser Val Ile Gln Ser
            180                 185                 190

Thr Phe Thr Leu Gln Leu Pro Phe Cys Gly His Arg Lys Val Asp Asn
        195                 200                 205

Phe Leu Cys Glu Val Pro Ala Met Ile Lys Leu Ala Cys Gly Asp Thr
```

```
                 210                 215                 220

Ser Leu Asn Glu Ala Val Leu Asn Gly Val Cys Thr Phe Phe Thr Val
225                 230                 235                 240

Val Pro Val Ser Val Ile Leu Val Ser Tyr Cys Phe Ile Ala Gln Ala
                245                 250                 255

Val Met Lys Ile Arg Ser Val Glu Gly Arg Arg Lys Ala Phe Asn Thr
                260                 265                 270

Cys Val Ser His Leu Val Val Val Phe Leu Phe Tyr Gly Ser Ala Ile
                275                 280                 285

Tyr Gly Tyr Leu Leu Pro Ala Lys Ser Ser Asn Gln Ser Gln Gly Lys
            290                 295                 300

Phe Ile Ser Leu Phe Tyr Ser Val Val Thr Pro Met Val Asn Pro Leu
305                 310                 315                 320

Ile Tyr Thr Leu Arg Asn Lys Asp Phe Arg Lys Ala Phe Gln Arg Leu
                325                 330                 335

Leu Cys Cys Ala Arg Arg Ala Ala Cys Arg Arg Ala Ala His Gly
            340                 345                 350

Asp Arg Pro Arg Ala Ser Gly Cys Leu Ala Arg Ala Gly Pro Pro Pro
                355                 360                 365

Ser Pro Gly Ala Pro Ser Asp Asp Asp Asp Asp Ala Gly Ala Thr
370                 375                 380

Pro Pro Ala Arg Leu Leu Glu Pro Trp Ala Gly Cys Asn Gly Gly Thr
385                 390                 395                 400

Thr Thr Val Asp Ser Asp Ser Ser Leu Asp Glu Pro Gly Arg Gln Gly
                405                 410                 415

Phe Ser Ser Glu Ser Lys Val
            420

<210> SEQ ID NO 61
<211> LENGTH: 40
<212> TYPE: DNA
<213> ORGANISM: Artificial Sequence
<220> FEATURE:
<223> OTHER INFORMATION: primer for preparing a plasmid expressing
      Rho-myc-Olfr 609

<400> SEQUENCE: 61
agaggatctg gaattcatgt cctactccaa tcattccagc                            40

<210> SEQ ID NO 62
<211> LENGTH: 37
<212> TYPE: DNA
<213> ORGANISM: Artificial Sequence
<220> FEATURE:
<223> OTHER INFORMATION: primer for preparing a plasmid expressing
      Rho-myc-Olfr 609

<400> SEQUENCE: 62
ggccgcccgg gtcgacttag tgaccctgga tatgccc                               37

<210> SEQ ID NO 63
<211> LENGTH: 960
<212> TYPE: DNA
<213> ORGANISM: Mus musculus

<400> SEQUENCE: 63
atgtcctact ccaatcattc cagcacttca ttctttctta ctggcctccc tggccttgag      60
acagtgtatc tctggctctc cattcctttg tgcaccatgt acattgcctc tctggcaggg     120
```

```
aatggcttga ttctgtgggt tgtaaagtca gagccctccc tgcaccagcc tatgtactac    180
tttctatcca tgcttgcagt tactgacctt ggcctgtctg tctccacact gcctaccatg    240
ctgacgatct atatgatggg tgtcagcgaa gtggcattag acatgtgcct tgcacagctc    300
ttcttcatcc atactttctc catcatggag tcatctgtgc tgctgactat ggcctttgac    360
cgtgttgtgg ccatcagcag tcccctacac tatgccacca tcctcaccaa ccctcgggtt    420
gccagtttgg gcatggtcat tttggtgcga agcattggtc tccacatccc tgcccccatc    480
atgctgaaga agctacctta ctgccagaag cgtcatcttt cccactctta ctgcctgcac    540
ccagatgtta tgaagctggc ctgtactgac actcgcatca acagtgccta tggcctcttt    600
gtggttctct ccactctggg tgtggactct gtgctcattg ttctatccta tgggctgatc    660
ctctacacag tgctgtcaat cgcttctaag actgaacgcc tcaaagccct caacacctgt    720
gtctcccaca tctgttctgt gctgctcttc tacacaccta tgattggcct ttctatgatc    780
caccgatttg gcaagtgggc ttccccctgc agccgtgtgt tgctctctta tcttcacttt    840
ctcacacctc cagtgctcaa tccagttgtt tataccaata agaccaagca gatccgacag    900
aggatttggc gtatcttccg gtgtggtgga agaagcattg gcatatcca gggtcactaa    960
```

```
<210> SEQ ID NO 64
<211> LENGTH: 351
<212> TYPE: PRT
<213> ORGANISM: Artificial Sequence
<220> FEATURE:
<223> OTHER INFORMATION: Rho-myc-olfr609

<400> SEQUENCE: 64

Met Asn Gly Thr Glu Gly Pro Asn Phe Tyr Val Pro Phe Ser Asn Lys
1               5                   10                  15

Thr Gly Val Val Glu Gln Lys Leu Ile Ser Glu Glu Asp Leu Glu Phe
            20                  25                  30

Met Ser Tyr Ser Asn His Ser Ser Thr Ser Phe Phe Leu Thr Gly Leu
        35                  40                  45

Pro Gly Leu Glu Thr Val Tyr Leu Trp Leu Ser Ile Pro Leu Cys Thr
    50                  55                  60

Met Tyr Ile Ala Ser Leu Ala Gly Asn Gly Leu Ile Leu Trp Val Val
65                  70                  75                  80

Lys Ser Glu Pro Ser Leu His Gln Pro Met Tyr Tyr Phe Leu Ser Met
                85                  90                  95

Leu Ala Val Thr Asp Leu Gly Leu Ser Val Ser Thr Leu Pro Thr Met
            100                 105                 110

Leu Thr Ile Tyr Met Met Gly Val Ser Glu Val Ala Leu Asp Met Cys
        115                 120                 125

Leu Ala Gln Leu Phe Phe Ile His Thr Phe Ser Ile Met Glu Ser Ser
    130                 135                 140

Val Leu Leu Thr Met Ala Phe Asp Arg Val Val Ala Ile Ser Ser Pro
145                 150                 155                 160

Leu His Tyr Ala Thr Ile Leu Thr Asn Pro Arg Val Ala Ser Leu Gly
                165                 170                 175

Met Val Ile Leu Val Arg Ser Ile Gly Leu His Ile Pro Ala Pro Ile
            180                 185                 190

Met Leu Lys Lys Leu Pro Tyr Cys Gln Lys Arg His Leu Ser His Ser
        195                 200                 205

Tyr Cys Leu His Pro Asp Val Met Lys Leu Ala Cys Thr Asp Thr Arg
    210                 215                 220
```

```
Ile Asn Ser Ala Tyr Gly Leu Phe Val Val Leu Ser Thr Leu Gly Val
225                 230                 235                 240

Asp Ser Val Leu Ile Val Leu Ser Tyr Gly Leu Ile Leu Tyr Thr Val
            245                 250                 255

Leu Ser Ile Ala Ser Lys Thr Glu Arg Leu Lys Ala Leu Asn Thr Cys
        260                 265                 270

Val Ser His Ile Cys Ser Val Leu Leu Phe Tyr Thr Pro Met Ile Gly
    275                 280                 285

Leu Ser Met Ile His Arg Phe Gly Lys Trp Ala Ser Pro Cys Ser Arg
290                 295                 300

Val Leu Leu Ser Tyr Leu His Phe Leu Thr Pro Pro Val Leu Asn Pro
305                 310                 315                 320

Val Val Tyr Thr Ile Lys Thr Lys Gln Ile Arg Gln Arg Ile Trp Arg
                325                 330                 335

Ile Phe Arg Cys Gly Gly Arg Ser Ile Gly His Ile Gln Gly His
            340                 345                 350

<210> SEQ ID NO 65
<211> LENGTH: 1179
<212> TYPE: DNA
<213> ORGANISM: Artificial Sequence
<220> FEATURE:
<223> OTHER INFORMATION: Fragment for preparing ChimeraOlfr609

<400> SEQUENCE: 65
atgtcctact ccaatcattc cagcacttca ttctttctta ctggcctccc tggccttgag      60
acagtgtatc tctggctctc cattcctttg tgcaccatgt acattgcctc tctggcaggg    120
aatggcttga ttctgtgggt tgtaaagtca gagccctccc tgcaccagcc tatgtactac    180
tttctatcca tgcttgcagt tactgacctt ggcctgtctg tctccacact gcctaccatg    240
ctgacgatct atatgatggg tgtcagcgaa gtggcattag acatgtgcct tgcacagctc    300
ttcttcatcc atactttctc catcatggag tcatctgtgc tgctgactat ggcctttgac    360
cgtgttgtgg ccatcagcag tcccctacac tatgccacca tcctcaccaa ccctcgggtt    420
gccagtttgg gcatggtcat tttggtgcga agcattggtc tccacatccc tgcccccatc    480
atgctgaaga agctacccta ctgccagaag cgtcatcttt cccactctta ctgcctgcac    540
ccagatgtta tgaagctggc ctgtactgac actcgcatca acagtgccta tggcctcttt    600
gtggttctct ccactctggg tgtggactct gtgctcattg ttctatccta tgggctgatc    660
ctctacacag tgctgtcaat cgcttctaag actgaacgcc tcaaagccct caacacctgt    720
gtctcccaca tctgttctgt gctgctcttc tacacaccta tgattggcct ttctatgatc    780
caccgatttg gcaagtgggc ttccccctgc agccgtgtgt tgctctctta tcttcacttt    840
ctcacacctc cagtgctcaa tccagttgtt tataccataa agaccaagga cttccgcaag    900
gctttccagc gcctgctttg ctgcgcgcgc gggccgcct gcagacgccg cgcagcccac    960
ggggaccggc cgcgcgcctc gggctgcctg gcgagagctg ggccgccgcc gtcccccggg   1020
gctccttcgg acgacgacga cgatgacgcc ggggccaccc cacccgcgcg cctgttggag   1080
ccctgggccg gctgcaacgg cgggacgacc actgtggaca gcgattcgag cctggacgag   1140
ccgggacgcc agggcttctc ctccgagtcc aaggtgtag                          1179

<210> SEQ ID NO 66
<211> LENGTH: 1275
<212> TYPE: DNA
```

<213> ORGANISM: Artificial Sequence
<220> FEATURE:
<223> OTHER INFORMATION: Fragment encoding ChimeraOlfr 609

<400> SEQUENCE: 66

```
atgaacggga ccgagggccc aaacttctac gtgcctttct ccaacaagac gggcgtcgta    60
gagcagaaac tcatctctga agaggatctg gaattcatgt cctactccaa tcattccagc   120
acttcattct ttcttactgg cctccctggc cttgagacag tgtatctctg gctctccatt   180
cctttgtgca ccatgtacat tgcctctctg gcagggaatg gcttgattct gtgggttgta   240
aagtcagagc cctccctgca ccagcctatg tactactttc tatccatgct tgcagttact   300
gaccttggcc tgtctgtctc cacactgcct accatgctga cgatctatat gatgggtgtc   360
agcgaagtgg cattagacat gtgccttgca cagctcttct tcatccatac tttctccatc   420
atggagtcat ctgtgctgct gactatggcc tttgaccgtg ttgtggccat cagcagtccc   480
ctacactatg ccaccatcct caccaaccct cgggttgcca gtttgggcat ggtcattttg   540
gtgcgaagca ttggtctcca catccctgcc cccatcatgc tgaagaagct accttactgc   600
cagaagcgtc atcttttccca ctcttactgc ctgcacccag atgttatgaa gctggcctgt   660
actgacactc gcatcaacag tgcctatggc ctctttgtgg ttctctccac tctgggtgtg   720
gactctgtgc tcattgttct atcctatggg ctgatcctct acacagtgct gtcaatcgct   780
tctaagactg aacgcctcaa agccctcaac acctgtgtct cccacatctg ttctgtgctg   840
ctcttctaca cacctatgat tggccttttct atgatccacc gatttggcaa gtgggcttcc   900
ccctgcagcc gtgtgttgct ctcttatctt cactttctca cacctccagt gctcaatcca   960
gttgttttata ccataaagac caaggacttc cgcaaggctt ccagcgccct gctttgctgc  1020
gcgcgccggg ccgcctgcag acgccgcgca gcccacgggg accggccgcg cgcctcgggc  1080
tgcctggcga gagctgggcc gccgccgtcc ccgggggctc cttcggacga cgacgacgat  1140
gacgccgggg ccaccccacc cgcgcgcctg ttggagcect gggccggctg caacggcggg  1200
acgaccactg tggacagcga ttcgagcctg gacgagccgg gacgccaggg cttctcctcc  1260
gagtccaagg tgtag                                                   1275
```

<210> SEQ ID NO 67
<211> LENGTH: 1269
<212> TYPE: DNA
<213> ORGANISM: Artificial Sequence
<220> FEATURE:
<223> OTHER INFORMATION: Fragment encoding ChimeraOlfr 168

<400> SEQUENCE: 67

```
atgaacggga ccgagggccc aaacttctac gtgcctttct ccaacaagac gggcgtcgta    60
gagcagaaac tcatctctga agaggatctg gaattcatgg agaaatggaa tcagagttca   120
agtgatttca ttctcttagg gttgcttcca caaaaccaaa ctggcctact acttatgatg   180
ctcatcatac ttgtcttctt tctggccttg tttggaaact cagcaatgat ccacctcatt   240
cgtgtggatc caaggctcca cacccccatg tactttctcc tcagtcagct ctctctcatg   300
gacctgatgt acatttctac cactgttccc aagatggcat taacttcct ttctggccag   360
aaaaacatct cttttctggg ctgtggtgtg cagtcttttt tcttttttgac catggcaggt   420
tctgagggct tgctcttggc ttccatggct tatgatcgtt ttgtggctat ctgccatccc   480
cttcactatc ccattcgcat gagcaagata atgtgtctga agatgatcat aggatcctgg  540
atattgggct caatcaactc tttagcacat tccatctatg cccttcatat tccttactgc  600
```

```
cattctaggt ccattaacca tttcttctgt gatgttccag ccatgttgcc cctggcctgt      660
atggacactt gggtttatga gtacatggtg tttgtgagca caagcctgtt tctcctactg      720
cctttccttg gtatcacagc ttcctatggt agggtccttt ttgctgtctt ccacatgcgc      780
tcaaaagagg gaaagaagaa ggccttcacc acatgctcaa ctcacttaac tgtggtgaca      840
ttttactatg cacctttttgt ctatacctat cttcgaccta ggagtcttcg ctccccaaca     900
gaagataaga ttctgactgt tttctacact atccttaccc ccatgctcaa ccccatcatc      960
tatagtctga ggaataagga cttccgcaag ctttccagc gcctgctttg ctgcgcgcgc      1020
cgggccgcct gcagacgccg cgcagcccac ggggaccggc cgcgcgcctc gggctgcctg     1080
gcgagagctg ggccgccgcc gtccccgggg gctccttcgg acgacgacga cgatgacgcc     1140
ggggccaccc cacccgcgcg cctgttggag ccctgggccg gctgcaacgg cgggacgacc     1200
actgtggaca gcgattcgag cctggacgag ccgggacgcc agggcttctc ctccgagtcc     1260
aaggtgtag                                                             1269

<210> SEQ ID NO 68
<211> LENGTH: 1272
<212> TYPE: DNA
<213> ORGANISM: Artificial Sequence
<220> FEATURE:
<223> OTHER INFORMATION: Fragment encoding ChimeraOlfr 15

<400> SEQUENCE: 68
atgaacggga ccgagggccc aaacttctac gtgcctttct ccaacaagac gggcgtcgta       60
gagcagaaac tcatctctga agaggatctg gaattcatgg aggtggacag caacagctcc      120
tctgggagct tcattctgat gggtgtctct gaccatcccc atctggagat catcttttt      180 gctgtcatcc tggcctctta cttgttgacg ctggttggga cttgaccat catcctgctt      240 tcgcgccttg atgctcggct ccacacaccc atgtacttct tcctcagcaa cctctcctct      300
ctagaccttg cctttactac cagttcagtc cctcagatgc tgaaaaattt atgggggcca      360
gacaagacaa tcagctatgg tgggtgtgta actcaactct atgttttcct ttggctgggg      420
gctactgagt gcatactgct cgtggtgatg gcatttgatc ggtatgtggc agtttgtcgg      480
cccctgcact acatgaccgt catgaatcct cgcctctgct gggggctggc tgctattagc      540
tggttgggtg gcttaggcaa ctccgtgatt cagtcaacat tcactctcca gctcccattt      600
tgcggacacc gaaaagtgga caacttcctg tgtgaggtac ccgccatgat taaattggcc      660 tgtgagaca caagtctcaa tgaggcggtg ctcaatggtg tttgtacctt cttcactgtg      720
gtcccagtaa gcgtcatcct ggtctcttac tgcttcattg ctcaggcagt gatgaagatc      780
cgctctgtgg agggacgtcg aaaggctttc aatacgtgtg tctcccactt ggtggtagtg      840
tttctcttct atggctctgc gatctatggg tatctgcttc cagctaagag cagtaatcaa      900
agccaaggaa aattcatttc tctcttctac tctgtggtca cacccatggt gaatccgctc      960
atctatactc taagaaacaa agacttccgc aaggctttcc agcgcctgct tgctgcgcg     1020 cgccgggccg cctgcagacg ccgcgcagcc cacggggacc ggccgcgcgc tcgggctgc     1080 ctggcgagag ctgggccgcc gccgtccccg gggctccttt cggacgacga cgacgatgac    1140
gccggggcca ccccacccgc gcgcctgttg agccctgggc cggctgcaa cggcgggacg     1200 accactgtgg acagcgattc gagcctggac gagccgggac gccagggctt ctcctccgag    1260
tccaaggtgt ag                                                        1272
```

```
<210> SEQ ID NO 69
<211> LENGTH: 424
<212> TYPE: PRT
<213> ORGANISM: Artificial Sequence
<220> FEATURE:
<223> OTHER INFORMATION: ChimeraOlfr 609

<400> SEQUENCE: 69

Met Asn Gly Thr Glu Gly Pro Asn Phe Tyr Val Pro Phe Ser Asn Lys
1               5                   10                  15

Thr Gly Val Val Glu Gln Lys Leu Ile Ser Glu Glu Asp Leu Glu Phe
            20                  25                  30

Met Ser Tyr Ser Asn His Ser Ser Thr Ser Phe Phe Leu Thr Gly Leu
        35                  40                  45

Pro Gly Leu Glu Thr Val Tyr Leu Trp Leu Ser Ile Pro Leu Cys Thr
    50                  55                  60

Met Tyr Ile Ala Ser Leu Ala Gly Asn Gly Leu Ile Leu Trp Val Val
65                  70                  75                  80

Lys Ser Glu Pro Ser Leu His Gln Pro Met Tyr Tyr Phe Leu Ser Met
                85                  90                  95

Leu Ala Val Thr Asp Leu Gly Leu Ser Val Ser Thr Leu Pro Thr Met
            100                 105                 110

Leu Thr Ile Tyr Met Met Gly Val Ser Glu Val Ala Leu Asp Met Cys
        115                 120                 125

Leu Ala Gln Leu Phe Phe Ile His Thr Phe Ser Ile Met Glu Ser Ser
    130                 135                 140

Val Leu Leu Thr Met Ala Phe Asp Arg Val Val Ala Ile Ser Ser Pro
145                 150                 155                 160

Leu His Tyr Ala Thr Ile Leu Thr Asn Pro Arg Val Ala Ser Leu Gly
                165                 170                 175

Met Val Ile Leu Val Arg Ser Ile Gly Leu His Ile Pro Ala Pro Ile
            180                 185                 190

Met Leu Lys Lys Leu Pro Tyr Cys Gln Lys Arg His Leu Ser His Ser
        195                 200                 205

Tyr Cys Leu His Pro Asp Val Met Lys Leu Ala Cys Thr Asp Thr Arg
    210                 215                 220

Ile Asn Ser Ala Tyr Gly Leu Phe Val Val Leu Ser Thr Leu Gly Val
225                 230                 235                 240

Asp Ser Val Leu Ile Val Leu Ser Tyr Gly Leu Ile Leu Tyr Thr Val
                245                 250                 255

Leu Ser Ile Ala Ser Lys Thr Glu Arg Leu Lys Ala Leu Asn Thr Cys
            260                 265                 270

Val Ser His Ile Cys Ser Val Leu Leu Phe Tyr Thr Pro Met Ile Gly
        275                 280                 285

Leu Ser Met Ile His Arg Phe Gly Lys Trp Ala Ser Pro Cys Ser Arg
    290                 295                 300

Val Leu Leu Ser Tyr Leu His Phe Leu Thr Pro Val Leu Asn Pro
305                 310                 315                 320

Val Val Tyr Thr Ile Lys Thr Lys Asp Phe Arg Lys Ala Phe Gln Arg
                325                 330                 335

Leu Leu Cys Cys Ala Arg Arg Ala Cys Arg Arg Ala Ala His
            340                 345                 350

Gly Asp Arg Pro Arg Ala Ser Gly Cys Leu Ala Arg Ala Gly Pro Pro
        355                 360                 365
```

```
Pro Ser Pro Gly Ala Pro Ser Asp Asp Asp Asp Asp Ala Gly Ala
    370             375                 380

Thr Pro Pro Ala Arg Leu Leu Glu Pro Trp Ala Gly Cys Asn Gly Gly
385             390                 395                 400

Thr Thr Thr Val Asp Ser Asp Ser Ser Leu Asp Glu Pro Gly Arg Gln
                405                 410                 415

Gly Phe Ser Ser Glu Ser Lys Val
                420

<210> SEQ ID NO 70
<211> LENGTH: 1035
<212> TYPE: DNA
<213> ORGANISM: Artificial Sequence
<220> FEATURE:
<223> OTHER INFORMATION: Fragment encoding Rho-myc-Olfr 15

<400> SEQUENCE: 70
atgaacggga ccgagggccc aaacttctac gtgcctttct ccaacaagac gggcgtcgta      60
gagcagaaac tcatctctga agaggatctg gaattcatgg aggtggacag caacagctcc     120
tctgggagct tcattctgat gggtgtctct gaccatcccc atctggagat catcttttt     180 gctgtcatcc tggcctctta cttgttgacg ctggttggga acttgaccat catcctgctt     240
tcgcgccttg atgctcggct ccacacaccc atgtacttct cctcagcaa cctctcctct     300 ctagaccttg cctttactac cagttcagtc cctcagatgt gaaaaattt atgggggcca     360 gacaagacaa tcagctatgg tgggtgtgta actcaactct atgttttcct ttggctgggg     420
gctactgagt gcatactgct cgtggtgatg catttgatc ggtatgtggc agtttgtcgg     480
cccctgcact acatgaccgt catgaatcct cgcctctgct ggggggctggc tgctattagc     540 tggttgggtg gcttaggcaa ctccgtgatt cagtcaacat tcactctcca gctcccattt     600
tgcggacacc gaaaagtgga caacttcctg tgtgaggtac ccgccatgat taaattggcc     660
tgtggagaca caagtctcaa tgaggcggtg ctcaatggtg tttgtacctt cttcactgtg     720
gtcccagtaa gcgtcatcct ggtctcttac tgcttcattg ctcaggcagt gatgaagatc     780
cgctctgtgg agggacgtcg aaaggctttc aatacgtgtg tctcccactt ggtggtagtg     840
tttctcttct atggctctgc gatctatggg tatctgcttc cagctaagag cagtaatcaa     900
agccaaggaa aattcatttc tctcttctac tctgtggtca cacccatggt gaatccgctc     960
atctatactc taagaaacaa agaagtgaag ggggccctgg gaagattgct ggggaaagga    1020
agaggagcca gctga                                                    1035

<210> SEQ ID NO 71
<211> LENGTH: 1056
<212> TYPE: DNA
<213> ORGANISM: Artificial Sequence
<220> FEATURE:
<223> OTHER INFORMATION: Fragment encoding Rho-myc-Olfr 609

<400> SEQUENCE: 71
atgaacggga ccgagggccc aaacttctac gtgcctttct ccaacaagac gggcgtcgta      60
gagcagaaac tcatctctga agaggatctg gaattcatgt cctactccaa tcattccagc     120
acttcattct ttcttactgg cctccctggc cttgagacag tgtatctctg ctctccatt     180 cctttgtgca ccatgtacat tgcctctctg gcagggaatg gcttgattct gtgggttgta     240
aagtcagagc cctcccctgca ccagcctatg tactactttc tatccatgct tgcagttact     300
gaccttggcc tgtctgtctc cacactgcct accatgctga cgatctatat gatgggtgtc     360
```

```
agcgaagtgg cattagacat gtgccttgca cagctcttct tcatccatac tttctccatc    420
atggagtcat ctgtgctgct gactatggcc tttgaccgtg ttgtggccat cagcagtccc    480
ctacactatg ccaccatcct caccaaccct cgggttgcca gtttgggcat ggtcattttg    540
gtgcgaagca ttggtctcca catccctgcc cccatcatgc tgaagaagct accttactgc    600
cagaagcgtc atctttccca ctcttactgc ctgcacccag atgttatgaa gctggcctgt    660
actgacactc gcatcaacag tgcctatggc ctctttgtgg ttctctccac tctgggtgtg    720
gactctgtgc tcattgttct atcctatggg ctgatcctct acacagtgct gtcaatcgct    780
tctaagactg aacgcctcaa agccctcaac acctgtgtct cccacatctg ttctgtgctg    840
ctcttctaca cacctatgat tggcctttct atgatccacc gatttggcaa gtgggcttcc    900
ccctgcagcc gtgtgttgct ctcttatctt cactttctca cacctccagt gctcaatcca    960
gttgtttata ccataaagac caagcagatc cgacagagga tttggcgtat cttccggtgt   1020
ggtggaagaa gcattgggca tatccagggt cactaa                             1056
```

METHOD FOR PRODUCING CAMP USING CHIMERIC OLFACTORY RECEPTOR

CROSS-REFERENCE TO RELATED APPLICATIONS

This application is a continuation of International Application No. PCT/JP2011/005950, filed on Oct. 24, 2011, which claims priority of Japanese Patent Application No. 2010-238202, filed on Oct. 25, 2010 and International Application No. PCT/JP2011/002477, filed on Apr. 27, 2011, the disclosure of these applications are incorporated by reference herein.

TECHNICAL FIELD

The present invention relates to a method for producing cAMP using a chimeric olfactory receptor.

BACKGROUND

An olfactory receptor is a trimeric G protein-coupled receptor (hereinafter, referred to as "GPCR"). More particularly, the olfactory receptor is one kind of trimeric G protein-coupled seven-transmembrane receptor.

FIG. 1 shows a mechanism by which a stimulus of an odor molecule to a cell membrane is converted into an electric signal.

The olfactory receptor is a membrane protein which is expressed on the cell membrane. The cell membrane is mainly composed of a lipid bilayer membrane. The lipid bilayer membrane has a structure of two layers each consisting of phospholipid molecules arranged in a high density. This lipid bilayer membrane is shown in the center of FIG. 1 schematically. In FIG. 1, the outside of the cell is above the upper part of the lipid bilayer membrane. On the other hand, the inside of the cell is below the lower part of the lipid bilayer membrane. The trimeric G protein is placed in the vicinity of the olfactory receptor.

The trimeric G protein is a heterotrimer comprised of an alpha subunit (Gαolf), a beta-subunit (Gβ), and a gamma subunit (Gγ). The cell contains adenylate cyclase. In FIG. 1, the adenylate cyclase is referred to as "AC". To be more exact, the adenylate cyclase is a transmembrane-type protein. A protein RTP1S (SEQ ID NO: 42) has a function to assist the olfactory receptors to be expressed in the cell membrane. It is noted that the protein RTP1S is not directly associated with the mechanism.

Next, the mechanism is described. The odor molecule binds to the olfactory receptor. The binding separates the trimeric G protein into the alpha subunit (Gαolf) and a beta-gamma complex. The beta-gamma complex consists of the subunit Gβ and the subunit Gγ. The separated Gαolf activates the adenylate cyclase (AC). The activated adenylate cyclase (AC) converts adenosine triphosphate (ATP) into cyclic adenosine monophosphate (cAMP).

The cyclic adenosine monophosphate (cAMP) activates an ion channel, more particularly, for example, a cyclic nucleotide gated ion channel (CNG). The activation allows an ion to be transported from the inside of the cell to the outside of the cell, or from the outside of the cell to the inside of the cell. The degree of the transport of the ion can be measured as an electric signal.

Needless to say, when the production amount of the cyclic adenosine monophosphate (cAMP) is greater, an amount of the obtained electric signal is greater. The greater amount of the electric signal improves the measurement accuracy.

Further, it is known that a stimulus to a beta-1 adrenergic receptor increases the production amount of the cAMP in the cell. When many olfactory receptors in which a part of the beta-1 adrenergic receptor is incorporated are expected to increase the product amount of the cAMP and to improve the measurement accuracy thereby. Such an olfactory receptor, namely, the olfactory receptor in which a part of a different receptor (in this case, beta-1 adrenergic receptor) is incorporated, is referred to as a "chimeric olfactory receptor".

DISCLOSURE OF PRIOR ART

Non Patent Literature 1 discloses that intracellular domains IC3 and IC4 of the adrenergic receptor are important for the interaction with the trimeric G protein.

Non Patent Literature 2 discloses that the production amount of the cAMP is significantly decreased by a point mutation into the IC3 domain, a point mutation into the IC4 domain, deletion of the IC4 domain, or a substitution of the IC4 domain with the IC4 domain of rhodopsin.

Non Patent Literature 3 discloses that a Flag-Rho mOREG where a Flag-tag is added to the N'-end of the Rho-mOREG is transported more quickly than the Rho-mOREG to the cell membrane surface, and thereby the response of the olfactory receptor is increased.

CITATION LIST

Non Patent Literature

[Non Patent Literature 1] Noel M. Delos Santos, Lidia A. Gardner, Stephen W. White, Suleiman W. Bahouth (2006) J. Biol. Chem., 281, 12,896-12,907

[Non Patent Literature 2] Kato A., Katada S., Touhara K. (2008) J. Neurochem., 107, 1261-1270

[Non Patent Literature 3] Katada S., Tanaka M., Touhara K. (2004) J. Neurochem., 90, 1453-1463

SUMMARY OF INVENTION

Technical Problem

However, unlike the above-mentioned expectation, the present inventors discovered that most of chimeric olfactory receptors decrease a product amount of the cAMP.

The purpose of the present invention is to provide a chimera olfactory receptor capable of increasing the product amount of the cAMP.

Solution to Problem

In order to solve the above-mentioned problem(s), provided are the methods A1 to C6, the chimeric olfactory receptors D1 to D4, the lipid bilayer membranes E1 to E5, and the reaction systems F1 to F5:

A1. A method for producing cAMP using a chimeric olfactory receptor, the method comprising steps of:

(a) preparing a reaction system comprising a first layer, a lipid bilayer membrane, and a second layer; wherein the lipid bilayer membrane is interposed between the first layer and the second layer, the lipid bilayer membrane comprises the chimeric olfactory receptor and adenylate cyclase;

the chimeric olfactory receptor penetrates the lipid bilayer membrane;

the adenylate cyclase penetrates the lipid bilayer membrane;

the second layer contains ATP and a G protein;

the G protein is placed in the vicinity of one end of the chimeric olfactory receptor;

the chimeric olfactory receptor is derived from a mouse olfactory receptor consisting of an amino acid sequence of (N-terminal)-an EC1 domain-a TM1 domain-an IC1 domain-a TM2 domain-an EC2 domain-a TM3 domain-an IC2 domain-a TM4 domain-an EC3 domain-a TM5 domain-an IC3 domain-a TM6 domain-an EC4 domain-a TM7 domain-an IC4 domain-(C-terminal);

the N-terminal of the chimeric olfactory receptor is modified with an amino acid sequence of Rho tag (SEQ ID NO:01)-myc epitope tag (SEQ ID NO:04); and the IC4 is substituted with an IC4 domain of a beta-1 adrenergic receptor; and (b) supplying a chemical substance which stimulates the chimeric olfactory receptor to the first layer so as to produce the cAMP from the ATP.

A2. The method according to item A1, wherein
the mouse olfactory receptor is a mouse olfactory receptor for eugenol;
the chemical substance is eugenol.

A2-1. The method according to item A1, wherein
the mouse olfactory receptor is a mouse olfactory receptor Olfr168;
the chemical substance is 2-pentanone.

A2-2. The method according to item A1, wherein
the mouse olfactory receptor is a mouse olfactory receptor Olfr15;
the chemical substance is cyclohexanone.

A2-3. The method according to item A1, wherein
the mouse olfactory receptor is a mouse olfactory receptor Olfr609;
the chemical substance is vanillic acid.

A3. The method according to item A2, wherein
the chimeric olfactory receptor consists of an amino acid sequence represented by SEQ ID NO: 36.

A3-1. The method according to item A2-1, wherein
the chimeric olfactory receptor consists of an amino acid sequence represented by SEQ ID NO: 51.

A3-2. The method according to item A2-2, wherein
the chimeric olfactory receptor consists of an amino acid sequence represented by SEQ ID NO: 60.

A3-3. The method according to item A2-3, wherein
the chimeric olfactory receptor consists of an amino acid sequence represented by SEQ ID NO: 69.

A4. The method according to item A1, wherein
the G protein comprises Gαolf, Gβ and, Gγ;
in the step (b), the G protein is divided into the Gαolf and a complex;
the complex consists of the Gβ and the Gγ; and
the Gαolf activates the adenylate cyclase.

A5. The method according to item A1, wherein
the lipid bilayer membrane further comprises an ion channel;
the ion channel penetrates the lipid bilayer membrane; and
the cAMP produced in the step (b) activates the ion channel.

A6. The method according to item A5, wherein
the ion channel is a calcium ion channel.

B1. A method for determining whether or not a sample solution contains a molecule which stimulates a chimeric olfactory receptor; the method comprising:

(a) preparing a reaction system comprising a first layer, a lipid bilayer membrane, and a second layer; wherein
the lipid bilayer membrane is interposed between the first layer and the second layer, at least one layer of the first layer and the second layer contains ions;

the lipid bilayer membrane comprises the chimeric olfactory receptor, an ion channel, and adenylate cyclase;

the chimeric olfactory receptor penetrates the lipid bilayer membrane;

the adenylate cyclase penetrates the lipid bilayer membrane;

the ion channel penetrates the lipid bilayer membrane;

the second layer contains ATP and a G protein;

the G protein is placed in the vicinity of one end of the chimeric olfactory receptor;

the chimeric olfactory receptor is derived from a mouse olfactory receptor consisting of an amino acid sequence of (N-terminal)-an EC1 domain-a TM1 domain-an IC1 domain-a TM2 domain-an EC2 domain-a TM3 domain-an IC2 domain-a TM4 domain-an EC3 domain-a TM5 domain-an IC3 domain-a TM6 domain-an EC4 domain-a TM7 domain-an IC4 domain-(C-terminal);

the N-terminal of the chimeric olfactory receptor is modified with an amino acid sequence of Rho tag (SEQ ID NO:01)-myc epitope tag (SEQ ID NO:04); and the IC4 is substituted with an IC4 domain of a beta-1 adrenergic receptor; and (b) supplying the sample solution to the first layer and measuring the concentration of the ions contained in the at least one layer of the first layer and the second layer; and (c) determining, if the measured concentration of the ions is varied, that the sample solution contains the molecule which stimulates the chimeric olfactory receptor.

B2. The method according to item B1, wherein
the mouse olfactory receptor is a mouse olfactory receptor for eugenol;
the molecule which stimulates a chimeric olfactory receptor is eugenol.

B2-1. The method according to item B1, wherein
the mouse olfactory receptor is a mouse olfactory receptor Olfr168;
the molecule which stimulates a chimeric olfactory receptor is 2-pentanone.

B2-2. The method according to item B1, wherein
the mouse olfactory receptor is a mouse olfactory receptor Olfr15;
the molecule which stimulates a chimeric olfactory receptor is cyclohexanone.

B2-3. The method according to item B1, wherein
the mouse olfactory receptor is a mouse olfactory receptor Olfr609;
the molecule which stimulates a chimeric olfactory receptor is vanillic acid.

B3. The method according to item B2, wherein
the chimeric olfactory receptor consists of an amino acid sequence represented by SEQ ID NO: 36.

B3-1. The method according to item B2-1, wherein
the chimeric olfactory receptor consists of an amino acid sequence represented by SEQ ID NO: 51.

B3-2. The method according to item B2-2, wherein
the chimeric olfactory receptor consists of an amino acid sequence represented by SEQ ID NO: 60.

B3-3. The method according to item B2-3, wherein
the chimeric olfactory receptor consists of an amino acid sequence represented by SEQ ID NO: 69.

B4. The method according to item B1, wherein
the G protein comprises Gαolf, Gβ and, Gγ;
in the step (b), the G protein is divided into the Gαolf and a complex;
the complex consists of the Gβ and the Gγ; and
the Gαolf activates the adenylate cyclase.

B5. The method according to item B1, wherein
the lipid bilayer membrane further comprises an ion channel;
the ion channel penetrates the lipid bilayer membrane; and
the cAMP produced in the step (b) activates the ion channel.

B6. The method according to item B5, wherein
the ion channel is a calcium ion channel.

C1. A method for quantifying a chemical substance which is contained in a sample solution and which stimulates a chimeric olfactory receptor; the method comprising:
(a) preparing a reaction system comprising a first layer, a lipid bilayer membrane, and a second layer; wherein
the lipid bilayer membrane is interposed between the first layer and the second layer,
at least one layer of the first layer and the second layer contains ions;
the lipid bilayer membrane comprises the chimeric olfactory receptor, an ion channel, and adenylate cyclase;
the chimeric olfactory receptor penetrates the lipid bilayer membrane;
the adenylate cyclase penetrates the lipid bilayer membrane;
the ion channel penetrates the lipid bilayer membrane;
the second layer contains ATP and a G protein;
the G protein is placed in the vicinity of one end of the chimeric olfactory receptor;
the chimeric olfactory receptor is derived from a mouse olfactory receptor consisting of an amino acid sequence of (N-terminal)-an EC1 domain-a TM1 domain-an IC1 domain-a TM2 domain-an EC2 domain-a TM3 domain-an IC2 domain-a TM4 domain-an EC3 domain-a TM5 domain-an IC3 domain-a TM6 domain-an EC4 domain-a TM7 domain-an IC4 domain-(C-terminal);
the N-terminal of the chimeric olfactory receptor is modified with an amino acid sequence of Rho tag (SEQ ID NO:01)-myc epitope tag (SEQ ID NO:04); and
the IC4 is substituted with an IC4 domain of a beta-1 adrenergic receptor; and
(b) supplying the sample solution to the first layer and measuring the concentration of the ions contained in the at least one layer of the first layer and the second layer; and
(c) quantifying the chemical substance which is contained in the sample solution on the basis of the amount of the change of the measured concentration of the ion.

C2. The method according to item C1, wherein
the mouse olfactory receptor is a mouse olfactory receptor for eugenol;
the chemical substance is eugenol.

C2-1. The method according to item C1, wherein
the mouse olfactory receptor is a mouse olfactory receptor Olfr168;
the chemical substance is 2-pentanone.

C2-2. The method according to item C1, wherein the mouse olfactory receptor is a mouse olfactory receptor Olfr15;
the chemical substance is cyclohexanone.

C2-3. The method according to item C1, wherein
the mouse olfactory receptor is a mouse olfactory receptor Olfr609;
the chemical substance is vanillic acid.

C3. The method according to item C2, wherein
the chimeric olfactory receptor consists of an amino acid sequence represented by SEQ ID NO: 36.

C3-1. The method according to item C2-1, wherein
the chimeric olfactory receptor consists of an amino acid sequence represented by SEQ ID NO: 51.

C3-2. The method according to item C2-2, wherein
the chimeric olfactory receptor consists of an amino acid sequence represented by SEQ ID NO: 60.

C3-3. The method according to item C2-3, wherein
the chimeric olfactory receptor consists of an amino acid sequence represented by SEQ ID NO: 69.

C4. The method according to item C1, wherein
the G protein comprises Gαolf, Gβ and, Gγ;
in the step (b), the G protein is divided into the Gαolf and a complex;
the complex consists of the Gβ and the Gγ; and
the Gαolf activates the adenylate cyclase.

C5. The method according to item C1, wherein
the lipid bilayer membrane further comprises an ion channel;
the ion channel penetrates the lipid bilayer membrane; and
the cAMP produced in the step (b) activates the ion channel.

C6. The method according to item C5, wherein
the ion channel is a calcium ion channel.

D1. A chimeric olfactory receptor represented by SEQ ID NO: 36

D2. A chimeric olfactory receptor represented by SEQ ID NO: 51

D3. A chimeric olfactory receptor represented by SEQ ID NO: 60

D4. A chimeric olfactory receptor represented by SEQ ID NO: 69

E1. A lipid bilayer membrane which is comprised as part of a reaction system used for detecting or quantifying a chemical substance contained in a sample solution, comprising:
a chimeric olfactory receptor;
an ion channel;
and adenylate cyclase; wherein
the chimeric olfactory receptor penetrates the lipid bilayer membrane;
the adenylate cyclase penetrates the lipid bilayer membrane;
the ion channel penetrates the lipid bilayer membrane;
the G protein is placed in the vicinity of one end of the chimeric olfactory receptor;
the chimeric olfactory receptor is derived from a mouse olfactory receptor consisting of an amino acid sequence of (N-terminal)-an EC1 domain-a TM1 domain-an IC1 domain-a TM2 domain-an EC2 domain-a TM3 domain-an IC2 domain-a TM4 domain-an EC3 domain-a TM5 domain-an IC3 domain-a TM6 domain-an EC4 domain-a TM7 domain-an IC4 domain-(C-terminal);
the N-terminal of the chimeric olfactory receptor is modified with an amino acid sequence of Rho tag (SEQ ID NO:01)-myc epitope tag (SEQ ID NO:04); and
the IC4 is substituted with an IC4 domain of a beta-I adrenergic receptor.

E2. The lipid bilayer membrane according to item E2, wherein
The chimeric olfactory receptor consists of an amino acid sequence represented by SEQ ID NO: 36.

E3. The lipid bilayer membrane according to item E2, wherein
The chimeric olfactory receptor consists of an amino acid sequence represented by SEQ ID NO: 51.

E4. The lipid bilayer membrane according to item E2, wherein
The chimeric olfactory receptor consists of an amino acid sequence represented by SEQ ID NO: 60.

E5. The lipid bilayer membrane according to item E2, wherein

The chimeric olfactory receptor consists of an amino acid sequence represented by SEQ ID NO: 69.

F1. A reaction system used for detecting or quantifying a chemical substance contained in a sample solution, comprising:
a first layer;
a lipid bilayer membrane;
and a second layer; wherein
the lipid bilayer membrane is interposed between the first layer and the second layer,
at least one layer of the first layer and the second layer contains ions;
the lipid bilayer membrane comprises the chimeric olfactory receptor, an ion channel, and adenylate cyclase;
the chimeric olfactory receptor penetrates the lipid bilayer membrane;
the adenylate cyclase penetrates the lipid bilayer membrane;
the ion channel penetrates the lipid bilayer membrane;
the second layer contains ATP and a G protein;
the G protein is placed in the vicinity of one end of the chimeric olfactory receptor;
the chimeric olfactory receptor is derived from a mouse olfactory receptor consisting of an amino acid sequence of (N-terminal)-an EC1 domain-a TM1 domain-an IC1 domain-a TM2 domain-an EC2 domain-a TM3 domain-an IC2 domain-a TM4 domain-an EC3 domain-a TM5 domain-an IC3 domain-a TM6 domain-an EC4 domain-a TM7 domain-an IC4 domain-(C-terminal);
the N-terminal of the chimeric olfactory receptor is modified with an amino acid sequence of Rho tag (SEQ ID NO:01)-myc epitope tag (SEQ ID NO:04); and
the IC4 is substituted with an IC4 domain of a beta-1 adrenergic receptor.

F2. The reaction system according to item F1, wherein
The chimeric olfactory receptor consists of an amino acid sequence represented by SEQ ID NO: 36.

F3. The reaction system according to item F1, wherein
The chimeric olfactory receptor consists of an amino acid sequence represented by SEQ ID NO: 51.

F4. The reaction system according to item F1, wherein
The chimeric olfactory receptor consists of an amino acid sequence represented by SEQ ID NO: 60.

F5. The reaction system according to item F1, wherein
The chimeric olfactory receptor consists of an amino acid sequence represented by SEQ ID NO: 69.

Advantageous Effects of Invention

The present invention provides a chimeric olfactory receptor capable of increasing the production amount of the cAMP.

BRIEF DESCRIPTION OF DRAWINGS

FIG. 1 shows a mechanism that a stimulus of an odor molecule to a cell membrane is converted into an electric signal.

FIG. 2 shows an olfactory receptor having an N-terminal modified with a Rho tag (Rho-tag).

FIG. 3 shows an olfactory receptor having an N-terminal modified with the Rho tag and a myc epitope tag.

FIG. 4 shows the chimera olfactory receptor where the IC4 domain is substituted with the IC4 domain of a beta-1 adrenergic receptor and where the N-terminal is modified with the Rho tag and the myc epitope tag.

FIG. 5 shows the chimeric olfactory receptor where the EC1-IC1 domains and the IC4 domain are substituted with those of the beta-1 adrenergic receptor.

FIG. 6 shows the chimeric olfactory receptor where the EC1-IC1 domains and the IC4 domain are substituted with those of the beta-1 adrenergic receptor and where the N-terminal is modified with the Rho tag and the myc epitope tag.

FIG. 7 shows the chimeric olfactory receptor where the TM7 domain and the IC4 domain are substituted with those of the beta-1 adrenergic receptor and where the N-terminal is modified with the Rho tag and the myc epitope tag.

FIG. 8 shows the chimeric olfactory receptor where the IC3 domain is substituted with that of the beta-1 adrenergic receptor and where the N-terminal is modified with the Rho tag and the myc epitope tag.

FIG. 9 shows the chimeric olfactory receptor where the IC3 domain and the IC4 domain are substituted with those of the beta-1 adrenergic receptor and where the N-terminal is modified with the Rho tag and the myc epitope tag.

FIG. 10 shows a procedure for preparing a plasmid (beta-1 adrenergic receptor).

FIG. 11 shows a procedure for preparing a plasmid (Rho-mOREG).

[FIG 1]

FIG. 13 shows a procedure for preparing a plasmid (chimera1)

[FIG 1]

FIG. 15 shows a product amount of cAMP-when when a beta-1 adrenergic receptor was introduced and a product amount of cAMP-when when a beta-1 adrenergic receptor was not introduced.

FIG. 16 is a graph indicating the increase amounts of the concentration of the intracellular cAMP according to the example 1-1 and the comparative examples 1-1-1-7.

FIG. 17 is a graph indicating the concentration-response curves of the Rho-mOREG, the Rho-myc-mOREG, and the chimera 1 for the eugenol.

FIG. 18 shows a procedure for preparing a plasmid (Rho-mycOlfr168).

FIG. 19 shows a procedure for preparing a plasmid (Rho-mycOlfr15).

FIG. 20 shows a procedure for preparing a plasmid (Rho-mycOlfr609).

FIG. 21 shows a procedure for preparing a plasmid (chimera3).

DESCRIPTION OF EMBODIMENTS (Definition of Term)

Figure 1:
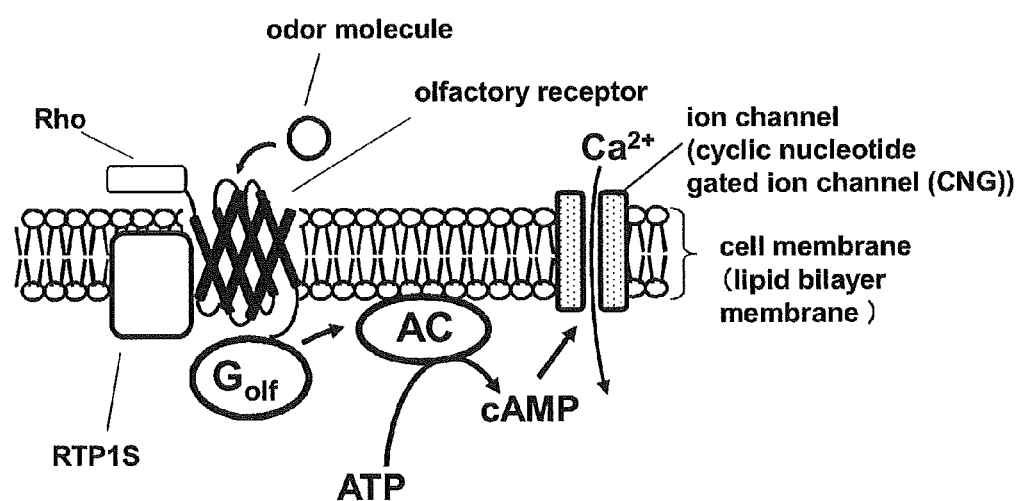
[FIG 1]

The terms used in the present specification is defined as below.

GPCR: G protein-binding acceptor
IC domain: intracellular domain
EC domain: extracellular domain
TM domain: cellular transmembrane domain
Gαolf: G protein alpha subunit which is specifically expressed on an olfactory epithelium
Gβ: G protein beta-subunit
Gγ: G protein gamma subunit
AC: adenylate cyclase
ATP: adenosine triphosphate
cAMP: cyclic adenosine monophosphate
Rho tag: N-terminal 20 amino acids of bovine rhodopsin. For more detail, see SEQ ID NO: 01 (the rhodopsin is derived from bovine optical nerve).
β1AR: beta-1 adrenergic receptor
RTP1S: a shorter receptor transporting protein lacking the N-terminal 36 amino acids of RTP1 (receptor transporting protein 1). For more detail, see SEQ ID NO: 42 and Matsunami et al., J. Biol. Chem., 2007, 282, 15284.
CNG: cyclic nucleotide gated ion channel
Plasmid (xx): plasmid containing a gene coding for a protein xx.
Gene flagment (xx): gene fragment containing a gene coding for a protein xx
mOREG: mouse olfactory receptor for eugenol (GenBank Accession Number: AB061228.1)
Olfr73: mouse olfactory receptor for eugenol, idendical to the mOREG.
Olfr168: mouse olfactory receptor for 2-pentanone (see SEQ ID NO: 43)
Olfr15: mouse olfactory receptor for cyclohexanone (SEQ ID NO: 44)
Olfr609: mouse olfactory receptor for vanillic acid (SEQ ID NO: 45)

An example of the mouse olfactory receptor is a mouse olfactory receptor mOREG, a mouse olfactory receptor Olfr168, a mouse olfactory receptor Olfr15, or a mouse olfactory receptor Olfr609.

The mouse olfactory receptor mOREG recognizes eugenol. In other words, the mouse olfactory receptor mOREG is stimulated by eugenol. Eugenol serves as an odor molecule with regard to the mouse olfactory receptor mOREG. The mouse olfactory receptor mOREG is referred to as a mouse olfactory receptor Olfr73.

The mouse olfactory receptor Olfr168 recognizes 2-pentanone. In other words, the mouse olfactory receptor Olfr168 is stimulated by 2-pentanone. 2-pentanone serves as an odor molecule with regard to the mouse olfactory receptor Olfr168.

The mouse olfactory receptor Olfr15 recognizes cyclohexanone. In other words, the mouse olfactory receptor Olfr15 is stimulated by cyclohexanone. Cyclohexanone serves as an odor molecule with regard to the mouse olfactory receptor Olfr15.

The mouse olfactory receptor Olfr609 recognizes vanillic acid. In other words, the mouse olfactory receptor Olfr609 is stimulated by vanillic acid. The vanillic acid serves as an odor molecule with regard to the mouse olfactory receptor Olfr609.

A mouse olfactory receptor is composed of seven cellular transmembrane domains (TM1-TM7), four extracellular domains (EC1-EC4), and four intracellular domains (IC1-IC4). In other words, the amino acid sequence of the mouse olfactory receptor consists of an amino acid sequence of (N-terminal)-an EC1 domain-a TM1 domain-an IC1 domain-a TM2 domain-an EC2 domain-a TM3 domain-an IC2 domain-a TM4 domain-an EC3 domain-a TM5 domain-an IC3 domain-a TM6 domain-an EC4 domain-a TM7 domain-an IC4 domain-(C-terminal).

Figure 2:
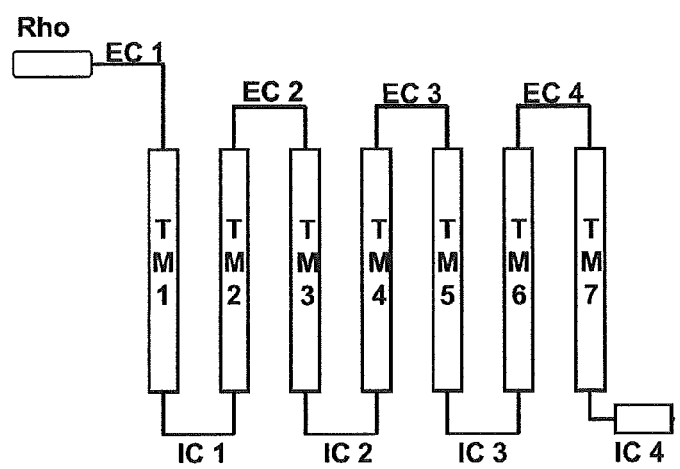
[FIG 2]

As shown in FIG. 2, the N terminal of the extracellular domain EC1 is modified with a Rho tag. This Rho tag consists of the amino acid sequence represented by MNGTEGPN-FYVPFSNKTGVV (SEQ ID NO:01). The Rho tag is known to promote the expression of the mouse olfactory receptor on the cell membrane (Krautwust D., Yau K. W., Reed R. (1999), Cell, 95, 917-925).

The mouse olfactory receptor for eugenol (mOREG) consists of the amino acid sequence represented by SEQ ID NO: 02.

The amino acid sequences of each domain of the mouse olfactory receptor for eugenol (mOREG) are as follows. The amino acid sequences are described in a direction from the N-terminal to the C-terminal.

```
EC1: MTLSDGNHSGAVFTLLGFSDY

TM1: PELTIPLFLIFLTIYSITVVGNIGMIVIIRI

IC1: NPKLHI

TM2: PMYFFLSHLSFVDFCYSSIVAPKMLVNLVT

EC2: MNRG

TM3: ISFVGCLVQFFFFCTFVVTESFLLGVMAYDRFVAI

IC2: RNPLLYTVAMS

TM4: QRLCAMLVLGSYAWGVVCSLILTC

EC3: SALNLSFYGFNMINHFFCEFSSLLLSLSRSDTS

TM5: VSQLLLFVFATFNEISTLLIILLSYVLI

IC3: VVTILKMKSASGR

TM6: RKAFSTCASHLTAITIFHGTILFLYCVPNSKN

EC4: SRHT

TM7: VKVASVFYTVVIPMLNPLIYSLRNKD

IC4: VKDTVKKIIGTKVYSS
```

The mouse olfactory receptor Olfr168 consists of the amino acid sequence represented by SEQ ID NO: 43.

The amino acid sequences of each domain of the mouse olfactory receptor Olfr168 are as follows. The amino acid sequences are described in a direction from the N-terminal to the C-terminal.

```
EC1: MEKWNQSSSDFILLGLLPQ

TM1: NQTGLLLMMLIILVFFLALFGNSAMIHLIRV

IC1: DPRLHT
```

```
TM2:  PMYFLLSQLSLMDLMYISTTVPKMAFNFLS
EC2:  GQKN
TM3:  ISFLGCGVQSFFFLTMAGSEGLLLASMAYDRF
IC2:  VAICHPLHYPIRMS
TM4:  KIMCLKMIIGSWILGSINSLAHSI
EC3:  YALHIPYCHSRSINHFFCDVPAMLPLACMDTW
TM5:  VYEYMVFVSTSLFLLLPFLGITASYGRV
IC3:  LFAVFHMRSKEGK
TM6:  KKAFTTCSTHLTVVTFYYAPFVYTYLRPRSLR
EC4:  SPT
TM7:  EDKILTVFYTILTPMLNPIIYSLRNK
IC4:  EVLGAMTRVLGTFSSMKP
```

The mouse olfactory receptor Olfr15 consists of the amino acid sequence represented by SEQ ID NO: 44.

The amino acid sequences of each domain of the mouse olfactory receptor Olfr15 are as follows. The amino acid sequences are described in a direction from the N-terminal to the C-terminal.

```
EC1:  MEVDSNSSSGSFILMGVSDH
TM1:  PHLEIIFFAVILASYLLTLVGNLTIILLSRL
IC1:  DARLHT
TM2:  PMYFFLSNLSSLDLAFTTSSVPQMLKNLWG
EC2:  PDKT
TM3:  ISYGGCVTQLYVFLWLGATECILLVVMAFDRY
IC2:  VAVCRPLHYMTVMN
TM4:  PRLCWGLAAISWLGGLGNSVIQST
EC3:  FTLQLPFCGHRKVDNFLCEVPAMIKLACGDTS
TM5:  LNEAVLNGVCTFFTVVPVSVILVSYCFI
IC3:  AQAVMKIRSVEGR
TM6:  RKAFNTCVSHLVVVFLFYGSAIYGYLLPAKSS
EC4:  NQS
TM7:  QGKFISLFYSVVTPMVNPLIYTLRNK
IC4:  EVKGALGRLLGKGRGAS
```

The mouse olfactory receptor Olfr609 consists of the amino acid sequence represented by SEQ ID NO: 45.

The amino acid sequences of each domain of the mouse olfactory receptor Olfr609 are as follows. The amino acid sequences are described in a direction from the N-terminal to the C-terminal.

```
EC1:  MSYSNHSSTSFFLTGLPGL
TM1:  ETVYLWLSIPLCTMYIASLAGNGLILWVVKS
IC1:  EPSLHQ
TM2:  PMYYFLSMLAVTDLGLSVSTLPTMLTIYMMG
EC2:  VSE
TM3:  VALDMCLAQLFFIHTFSIMESSVLLTMAFDRVVAI
IC2:  SSPLHYATILT
TM4:  NPRVASLGMVILVRSIGLHIPAPI
EC3:  MLKKLPYCQKRHLSHSYCLHPDVMKLACTDTR
TM5:  INSAYGLFVVLSTLGVDSVLIVLSYGLI
IC3:  LYTVLSIASKTER
TM6:  LKALNTCVSHICSVLLFYTPMIGLSMIHRFG
EC4:  KWASPC
TM7:  SRVLLSYLHFLTPPVLNPVVYTIKTK
IC4:  QIRQRIWRIFRCGGRSIGHIQGH
```

The beta-1 adrenergic receptor (β1AR) is the amino acid sequence represented by SEQ ID NO: 03.

Similarly to the mouse olfactory receptor, the beta-1 adrenergic receptor (β1AR) is also comprised of seven cellular transmembrane domains (TM1-TM7), four extracellular domains (EC1-EC4), and four intracellular domains (IC1-IC4).

The amino acid sequences of each domain of the beta-1 adrenergic receptor (β1AR) are as follows.

```
EC1:  MGAGALALGASEPCNLSSAAPLPDGAATAARLLVLASPPASLLPPASEGSAPLS
TM1:  QQWTAGMGLLLALIVLLIVVGNVLVIVAIAK
IC1:  TPRLQTL
TM2:  TNLFIMSLASADLVMGLLVVPFGATIVVW
EC2:  GRWEYG
TM3:  SFFCELWTSVDVLCVTASIETLCVIALDRYLAIT
IC2:  LPFRYQSLL
TM4:  TRARARALVCTVWAISALVSFLPILM
EC3:  HWWRAESDEARRCYNDPKCCDFVTN
TM5:  RAYAIASSVVSFYVPLCIMAFVYLRVFREAQ
IC3:  KQVKKIDSCERRFLTGPPRPPSPAPSPSPGPPRPADSLANGRSSKRRPSRLVALRE
```

-continued

```
TM6:    QKALKTLGIIMGVFTLCWLPFFLANVVKAF

EC4:    HRDLV

TM7:    PDRLFVFFNWLGYANSAFNPIIYCRSPD

IC4:    FRKAFQRLLCCARRAACRRRAAHGDRPRASGCLARAGPPPSPGAPSDDDDDAGATPP

ARLLEPWAGCNGGTTTVDSDSSLDEPGRQGFSSESKV
```

Similarly to the mouse olfactory receptor and β1AR, the chimeric olfactory receptor also consists of fifteen domains of EC1-IC4 domains.

Each domain of the chimeric olfactory receptor is selected from either of a corresponding domain included in the mouse olfactory receptor or a corresponding domain included in the β1AR. For example, the EC1 domain of the chimeric olfactory receptor is selected from either the EC1 domain included in the mouse olfactory receptor or the EC1 domain included in the β1AR. Similarly, the TM1, IC1, TM2, EC2, TM3, IC2, TM4, EC3, TM5, IC3, TM6, EC4, TM7, and IC4 domains are selected from either the TM1, IC1, TM2, EC2, TM3, IC2, TM4, EC3, TM5, IC3, TM6, EC4, TM7, and IC4 domains included in the mouse olfactory receptor or the TM1, IC1, TM2, EC2, TM3, IC2, TM4, EC3, TM5, IC3, TM6, EC4, TM7, and IC4 domains included in the β1AR, respectively.

Therefore, the theoretical number of the chimeric olfactory receptor is 2^15 (two to the fifteenth power, 32768).

The beta-1 adrenergic receptor (β1AR) is known to increase the product amount of the cyclic adenosine monophosphate (cAMP). Accordingly, the chimeric olfactory receptors obtained as above were expected to increase the product amount of the cAMP. However, unlike the expectation, the present inventors have revealed that almost all of the chimeric olfactory receptors decrease the product amount of the cAMP.

The present inventors have discovered that a chimeric olfactory receptor do increase the product amount of the cyclic adenosine monophosphate (cAMP) only under the condition that the chimeric olfactory receptor has the following properties (1) and (2): (1) the amino acid sequence of EQKLISEEDL (SEQ ID NO:04, hereinafter, referred to as "myc epitope tag") is inserted between the Rho tag and the EC1 domain; and (2) the IC4 domain of the mouse olfactory receptor is substituted with the IC4 domain of the beta-1 adrenergic receptor (β1AR).

Figure 4:
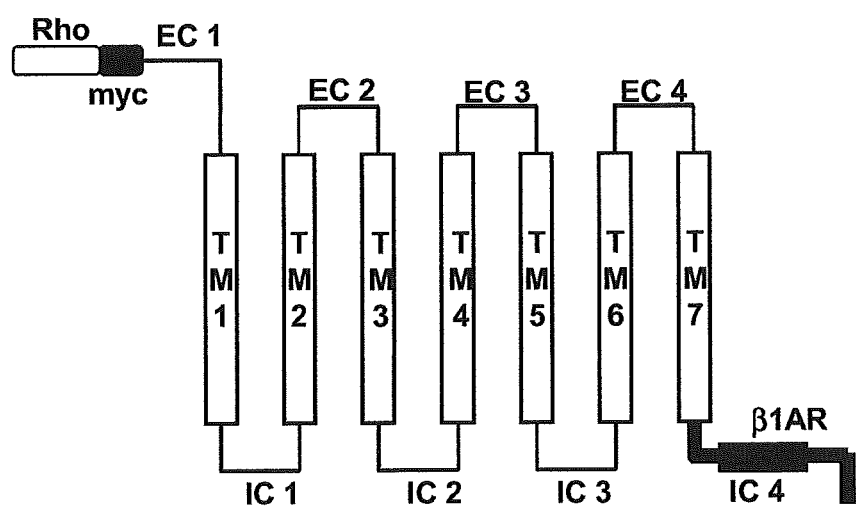
[FIG 4]

See FIG. 4.

As is clear from FIG. 4, the IC4 domain of the chimeric olfactory receptor includes the C terminal of the amino acid sequence of the chimeric olfactory receptor.

EXPERIMENT

Experiments supporting the above matters are described below.

Table 1 and Table 2 show the primers used in the experiment.

TABLE 1

| | |
|---|---|
| Primer 1 (SEQ ID NO: 5) | ATGGGCGCGGGGGCGCTCG |
| Primer 2 (SEQ ID NO: 6) | GAAGACGAAGAGGCGATCCGGCACCAGG |
| Primer 3 (SEQ ID NO: 7) | CACTGGGCATCATCATGGGTGTGTTCAC |
| Primer 4 (SEQ ID NO: 8) | CTACACCTTGGACTCGGAGGAGAAGCC |
| Primer 5 (SEQ ID NO: 9) | TTCGAATTCGCCACCATGGGCGCGGGGGCGCT |
| Primer 6 (SEQ ID NO: 10) | GAAGTCGACCTACACCTTGGACTCGGAGG |
| Primer 7 (SEQ ID NO: 11) | ctagactctgtcagatggaaatcacagtgg |
| Primer 8 (SEQ ID NO: 12) | ttaagaagaatagactttagtacctattat |
| Primer 9 (SEQ ID NO: 13) | cgtgcctttctccaacaagacgggcgtcgtaatgactctgtca gatggaaatcacagtg |
| Primer 10 (SEQ ID NO: 14) | cgaattcatgaacgggaccgagggcccaaacttctacgtgcct ttctccaacaagacgg |
| Primer 11 (SEQ ID NO: 15) | TCCCAGTTCAATTACAGCTCTTAAGG |
| Primer 12 (SEQ ID NO: 16) | tgacagagtcatgaattcCAGATCcTCTTCagagATgAGTTTC TGcTCtacgacgcccgtcttgttg |

TABLE 1-continued

| Primer 13 (SEQ ID NO: 17) | atctggaattcatgactctgtcagatggaaatcac |
| --- | --- |
| Primer 14 (SEQ ID NO: 18) | AAAgtcgacccGGGAttaagaagaatagactttagtacc |
| Primer 15 (SEQ ID NO: 19) | aagtcgggtctcagactgtatattaggggattc |
| Primer 16 (SEQ ID NO: 20) | acagtctgagacccgacttccgcaaggc |
| Primer 17 (SEQ ID NO: 21) | ATGTCTGCTCGAAGCATTAACCC |
| Primer 18 (SEQ ID NO: 22) | gagatatcACGCGTgaggttggtgagcgtctg |
| Primer 19 (SEQ ID NO: 23) | cgtgatatctctagagacttccgcaaggctttcc |

TABLE 2

| Primer 20 (SEQ ID NO: 24) | aaaACGCGTcccatgtacttctttctcagcc |
| --- | --- |
| Primer 21 (SEQ ID NO: 25) | aaatctagacttatttctcagactgtatattaggggattc |
| Primer 22 (SEQ ID NO: 26) | atggggtgtttgggcaacagcagcaagac |
| Primer 23 (SEQ ID NO: 27) | ggaggaggaggaggggtaggtttagg |
| Primer 24 (SEQ ID NO: 28) | aatgaattcgccaccatggggtgtttgggcaacag |
| Primer 25 (SEQ ID NO: 29) | aatgtcgactcacaagagttcgtactgcttgag |
| Primer 26 (SEQ ID NO: 30) | tgggtcctgcttcctcctgatcctgc |
| Primer 27 (SEQ ID NO: 31) | ccattcccaagccaggtctcacctcac |
| Primer 28 (SEQ ID NO: 32) | cagaattcgccaccatgtgtaagagtgtgaccaca |
| Primer 29 (SEQ ID NO: 33) | gaagtcgacttagacagaagtacggaaggag |
| Primer 30 (SEQ ID NO: 46) | AGAGGATCTGGAATTCATGGAGAAATGGAATCAGAGTTCAAGTG |
| Primer 31 (SEQ ID NO: 47) | GGCCGCCCGGGTCGACTCATGGTTTCATGGAAGAGAATG |
| Primer 32 (SEQ ID NO: 52) | atggaggtggacagcaac |
| Primer 33 (SEQ ID NO: 53) | tcagctggctcctcttcc |
| Primer 34 (SEQ ID NO: 54) | AGAGGATCTGGAATTCATGGAGGTGGACAGCAAC |
| Primer 35 (SEQ ID NO: 55) | GGCCGCCCGGGTCGACTCAGCTGGCTCCTCTTCC |
| Primer 36 (SEQ ID NO: 61) | AGAGGATCTGGAATTCATGTCCTACTCCAATCATTCCAGC |
| Primer 37 (SEQ ID NO: 62) | GGCCGCCCGGGTCGACTTAGTGACCCTGGATATGCCC |

(Preparation of Plasmid (Gαolf) and Plasmid (RTP1S))

First, a plasmid (Gαolf) and a plasmid (RTP1S) were prepared.

(Preparation of Plasmid (Gαolf))

The Gαolf (GenBank Accession Number: AY179169.1) is known to be localized at an olfactory bulb. For this reason, the gene coding for the Gαolf was prepared from the olfactory bulb. The olfactory bulb was isolated from a mouse. A cDNA was prepared from this isolated olfactory bulb. The Gαolf gene was amplified by a PCR method using this cDNA, the primer 22, and the primer 23.

The amplified Gαolf gene was ligated into a plasmid for cloning. A PCR method using this plasmid for cloning, the primer 24, and the primer 25 was performed. The primer 24 had a restriction enzyme site EcoRI. The primer 25 had a restriction enzyme site SalI.

In this way, obtained is the Gαolf gene having restriction enzyme sites EcoRI and SalI in the 5'-end thereof and the 3'-end thereof, respectively.

The obtained Gαolf gene was treated with restriction enzymes EcoRI and SalI. After treatment, the Gαolf gene was ligated into a plasmid for expressing a mammal which had been treated with the restriction enzymes EcoRI and SalI in advance. In this way, the plasmid (Gαolf) was obtained.

(Preparation of Plasmid (RTP1S))

Similarly to the Gαolf, the mouse RTP1S (GenBank Accession Number: EU070411) is known to be also localized at the olfactory bulb. For this reason, the gene coding for the RTP1S was also prepared from the olfactory bulb similarly to the case of the Gαolf. The plasmid (RTP1S) was prepared similarly to the preparation of the plasmid (Gαolf) except for the followings.

Instead of the set of primers consisting of the primer 22 and the primer 23, the set of primers consisting of the primer 26 and the primer 27 was used.

Instead of the set of primers consisting of the primer 24 and the primer 25, the set of primers consisting of the primer 28 and the primer 29 was used.

Reference Example 1

β1AR

In the reference example 1, the concentration of the cAMP provided by the β1AR was measured. The reference example 1 is roughly divided into three steps of Step 1: Preparation of Plasmid (β1AR), Step 2: Expression of β1AR in a cell membrane, and Step 3: Measurement of the change amount of the cAMP using an agonist.

(Step 1: Preparation of Plasmid (Beta-1 Adrenergic Receptor))

Figure 10:
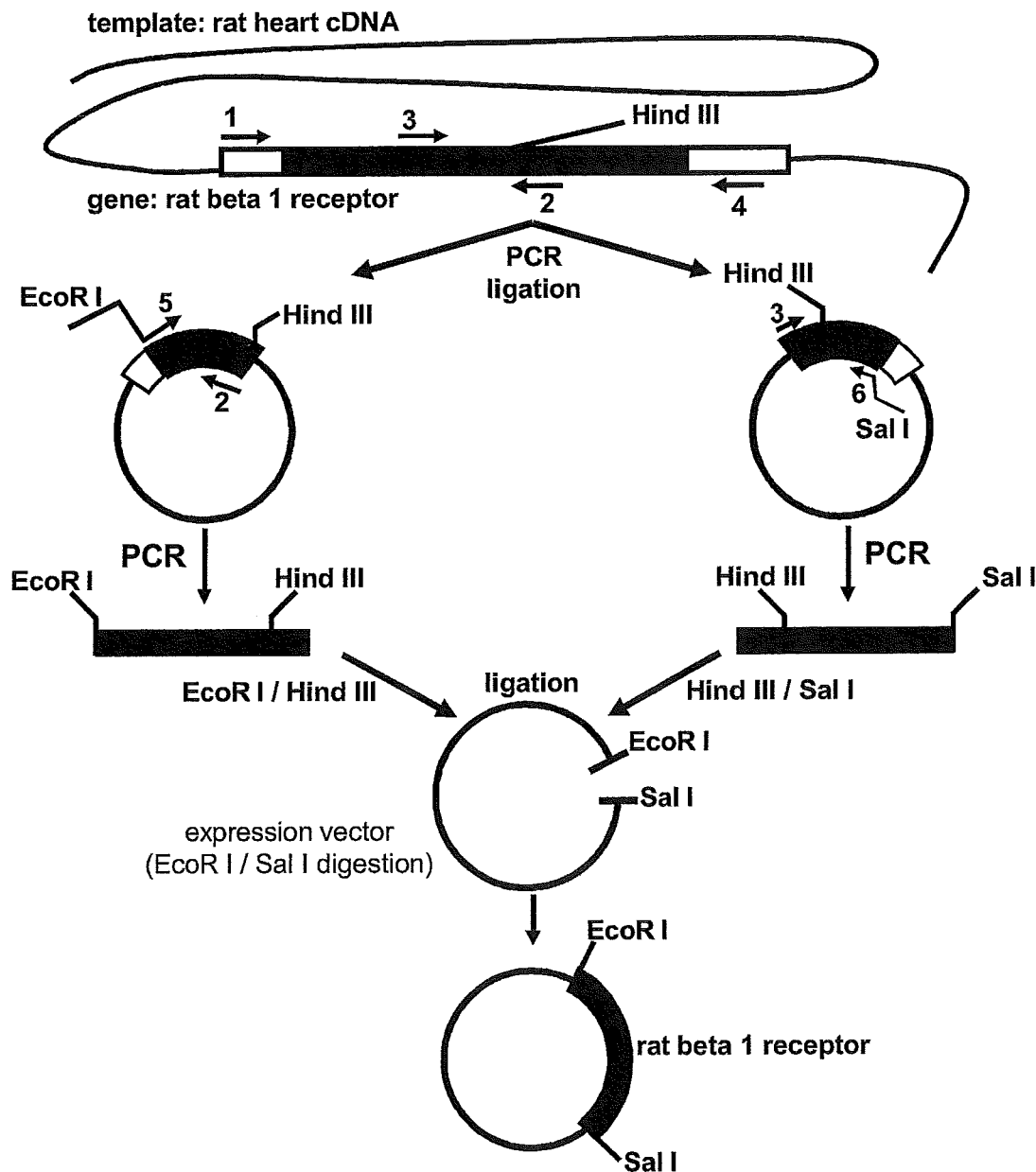
[FIG 10]

The gene of the beta-1 adrenergic receptor was amplified by a PCR method using a cDNA which was obtained by reverse-transcribing a RNA derived from a rat heart. The preparation procedure is described with reference to FIG. 10. FIG. 10 shows a procedure for preparing a plasmid for expressing the beta-1 adrenergic receptor, namely, a plasmid (beta-1 adrenergic receptor). As shown in FIG. 10, in the above-mentioned PCR method, the target gene (the gene coding for the beta-1 adrenergic receptor) was divided into two gene fragments.

As the primers for obtaining the two gene fragments, the primers 1-4 were used. One of these gene fragments, which is shown in the left side of FIG. 10, was obtained by a PCR method using the cDNA, the primer 1, and the primer 2. The other of the gene fragments, which is shown in the right side of FIG. 10, was obtained by a PCR method using the cDNA, the primer 3, and the primer 4. As shown in FIG. 10, the cDNA had a restriction enzyme site HindIII.

Each of the obtained two gene fragments was ligated into a plasmid. PCR reactions were conducted using these two plasmids. In the PCR reaction for the one of these gene fragments, the primer 5 and the primer 2 were used. The primer 5 had a restriction enzyme site EcoRI. In the PCR reaction for the other of gene fragments, the primer 3 and the primer 6 were used. The primer 6 had a restriction enzyme site SalI.

The 5'-end and the 3'-end of the amplified one gene fragment were treated with restriction enzymes EcoRI and HindIII, respectively. The 5'-end and the 3'-end of the amplified other gene fragment were treated with restriction enzymes HindIII and SalI, respectively. These two gene fragments were ligated into an expression vector which had been treated with restriction enzymes EcoRI and SalI in advance. In this way, the plasmid (beta-1 adrenergic receptor) was obtained.

(Step 2: Expression of the β1AR in a Cell Membrane)

HEK293T cells were transfected with the plasmid (Gαolf), the plasmid (RTP1S), and the plasmid (β1AR).

In particularly, the HEK293T cells were added in each of three petri dishes each containing a DMEM culture medium (Sigma-Aldrich). The DMEM culture medium contained 10% FBS (life technologies invitrogen), 30 units/mL of penicillin (Meiji Seika), and 30 mg/mL of streptomycin sulfate (Meiji Seika).

After the addition, the HEK293T cells were adhered spontaneously on the inner wall of the petri dish. The HEK293T cells were incubated overnight.

Subsequently, the HEK293T cells were transfected with the above-mentioned three plasmids by a lipofection method. The HEK293T cells were incubated for 48 hours, and the β1AR consisting of the protein represented by SEQ ID NO: 03 was expressed on the cell membrane of the HEK293T cell.

(Step 3: Measurement of the Change Amount of cAMP with an Agonist)

The DMEM culture mediums each containing the expressed β1AR were replaced with DMEM culture mediums containing 1 mM IBMX (Calbiochem). Subsequently, the HEK293T cells were incubated for 30 minutes under a temperature of 37 degrees Celsius. The abbreviation "IBMX" means 3-isobutyl-1-methylxanthine. The IBMX is one of the phosphodiesterase inhibitors. The IBMX stabilizes cAMP, which is unstable.

Subsequently, the DMEM culture mediums each containing 1 mM IBMX were replaced with Opti-MEM culture mediums (life technologies invitrogen) each containing 1 mM IBMX.

Isoproterenol aqueous solutions having concentrations shown in Table 3 were added as an agonist into the Opti-MEM culture mediums. The Opti-MEM culture mediums each containing the HEK293T cells capable of expressing the β1AR were left for 15 minutes under a temperature of 37 degrees Celsius.

Opti-MEM culture mediums were removed so as to leave HEK293T cells on the inner wall of the petri dish. 0.1M HCl was added to the Petri dish and left under room temperature for ten minutes. In this way, the HEK293T cells were eluted to obtain an eluate. The eluate was subjected to centrifugation at 600 g for ten minutes to obtain the supernatant as a sample solution.

The amount of the cAMP contained in the sample solution was measured by an EIA (enzyme immuno assay) method.

In order to standardize the difference of the number of the cells contained in the three petri dishes, the amount of the protein contained in the obtained supernatant was measured by a BCA (bicinchoninic acid) method.

The concentration of cAMP was calculated on the basis of the following formula:

The concentration of cAMP=the measured amount of the cAMP/the measured amount of the protein contained in the supernatant Reference Example 2

An experiment similar to the reference example 1 was conducted except that the plasmid (β1AR) was not used.

Figure 15:
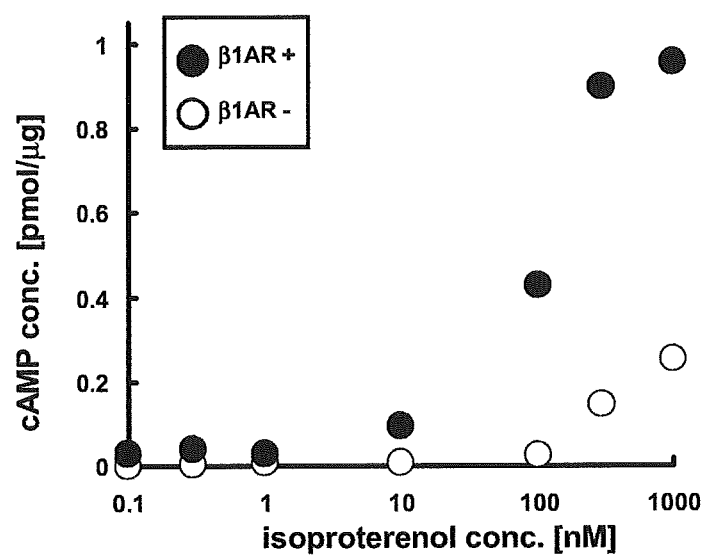
[FIG 15]

Table 3 shows the cAMP concentrations calculated in the reference example 1 and the reference example 2. FIG. 15 shows a graph made on the basis of Table 2.

TABLE 3

| ISO concentration [Unit: nM] | Presence of β1AR [Unit: pmol/μg] | Absence of β1AR [Unit: pmol/μg] |
|---|---|---|
| 0 | 0.0915 | 0.00475 |
| 0.01 | 0.0283 | 0.000631 |
| 0.03 | 0.0171 | 0.000298 |
| 0.1 | 0.0287 | 0.000274 |
| 0.3 | 0.0407 | 0.00224 |
| 1 | 0.0307 | 0.00612 |
| 10 | 0.0952 | 0.00570 |
| 100 | 0.427 | 0.0239 |
| 300 | 0.897 | 0.146 |
| 1000 | 0.956 | 0.255 |

As is clear from Table 2 and FIG. 15, when the β1AR was not introduced, the intracellular cAMP concentration did not increase very much. On the contrary, β1AR was stimulated by isoproterenol to increase the intracellular cAMP concentration significantly.

Experiment 1

In the experiment 1, transgenic proteins of mouse olfactory receptors for eugenol (mOREG) were produced.

The experiment 1 includes one example (Example 1-1) and seven comparative examples (Comparative examples 1-1 to 1-7).

Comparative Example 1-1

Rho-mOREG)

Figure 11:
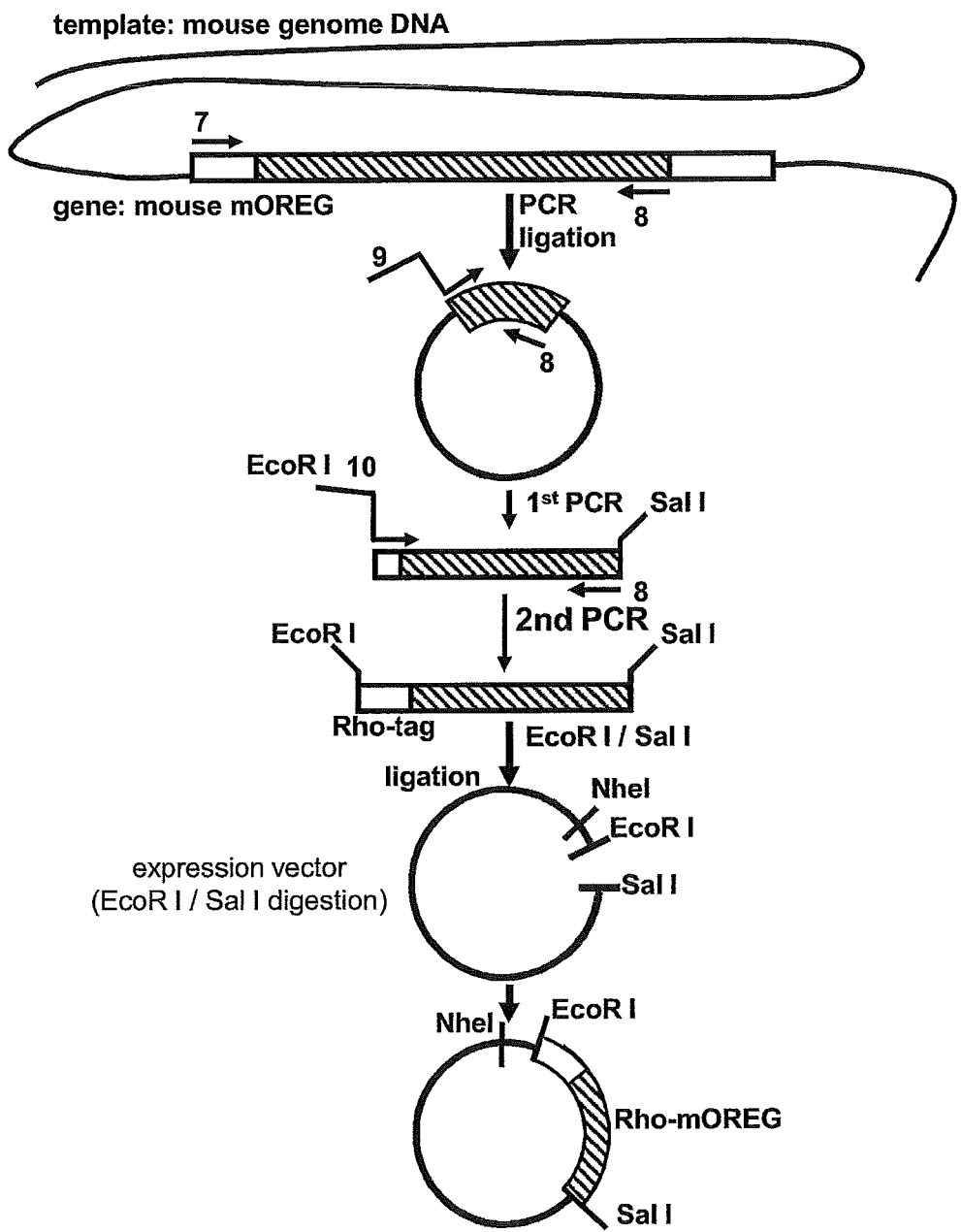
[FIG 11]

FIG. 11 shows a procedure for preparing a plasmid for expressing the mouse olfactory receptor for eugenol, Rho-mOREG, namely, a plasmid (Rho-mOREG). This plasmid (Rho-mOREG) is used to express the mouse olfactory receptor for eugenol Rho-mOREG, as shown in FIG. 2. Hereinafter, this olfactory receptor is abbreviated as "Rho-mOREG".

(Step 1: Preparation of the Plasmid (Rho-mOREG))

First, a gene (GenBank Accession Number: AB061228.1) coding for the mOREG was amplified by a PCR method using a mouse genomic DNA as a template. In this PCR method, the primer 7 and the primer 8 were used. The amplified gene was ligated into a plasmid for cloning so as to clone the gene coding for the mOREG.

Then, the gene sequence coding for the Rho tag was added to the 5'-end of the gene coding for the mOREG by a PCR method. Since the gene sequence coding for the Rho tag has sixty bases, the addition of the gene sequence coding for the Rho tag was divided into the following two steps (i.e., the first step and the second step).

In the first step, a PCR reaction was conducted using the above-mentioned plasmid coding for the mOREG, the primer 8, and the primer 9 so as to obtain a gene fragment in which thirty-one bases was added to the 5'-end of the gene coding for mOREG. The primer 9 had the thirty-one bases.

Similarly, in the second step, a PCR reaction was conducted using the gene fragment obtained in the first step, the primer 8, and the primer 10 so as to add the additional 29 bases to the 5'-end. The primer 10 had the additional 29 bases. The primer 10 also had a restriction enzyme site EcoRI.

In this way, the gene sequence (60 bases) coding for the Rho tag (SEQ ID NO: 01) was added to the 5'-end of the mOREG gene so as to obtain the Rho-mOERG gene fragment. This Rho-mOERG gene fragment was ligated into EcoRI/SalI sites of a plasmid for expressing a mammal. As shown in FIG. 11, this plasmid for expressing a mammal had three restriction enzyme sites NheI, EcoRI, and SalI. In this way, the plasmid (Rho-mOREG) was obtained. This plasmid (Rho-mOREG) had not only two restriction enzyme sites EcoRI and SalI, but also a restriction enzyme site NheI.

(Step 2: Expression of the Rho-mOREG to a Cell Membrane)

The expression was conducted similarly to that of the step 2 of the reference example 1 except that the plasmid (Rho-mOREG) was used instead of the plasmid (β1AR). In this way, the Rho-mOREG (SEQ ID NO: 34) was expressed on a cell membrane.

(Step 3: Measurement of the Change Amount of the cAMP with an Agonist)

The cAMP concentration was measured similarly to that of the step 3 of the reference example 1, except that an eugenol aqueous solution having a concentration of 300 μM was used as an agonist instead of the isoproterenol aqueous solution.

Based on the measured cAMP concentration, a concentration increase value was calculated in accordance with the following equation:

(Concentration increase value)=(the cAMP concentration measured when the concentration of the eugenol was 300μM)−(the cAMP concentration measured when the concentration of the eugenol was 0 μM)

The cAMP concentration measured when the concentration of the eugenol was 0 μM was $6.33 \times 10^{-3}$ pmol/μg.

Comparative Example 1-2

Rho-myc-mOREG

Figure 3:
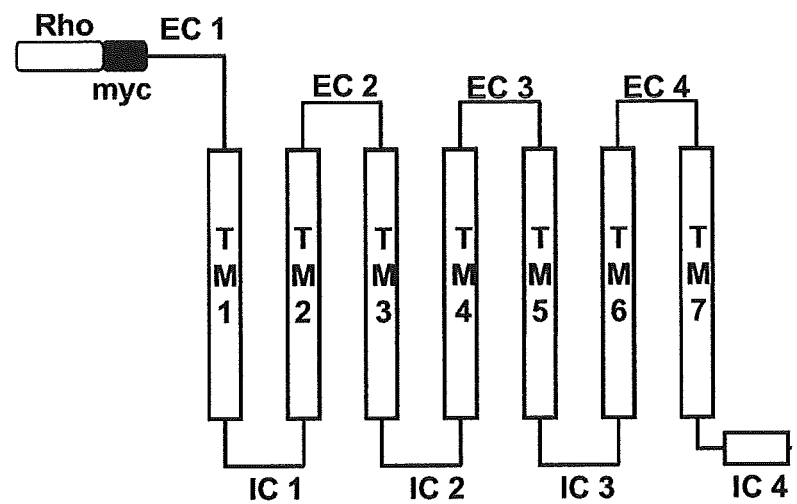
[FIG 3]
Figure 12:
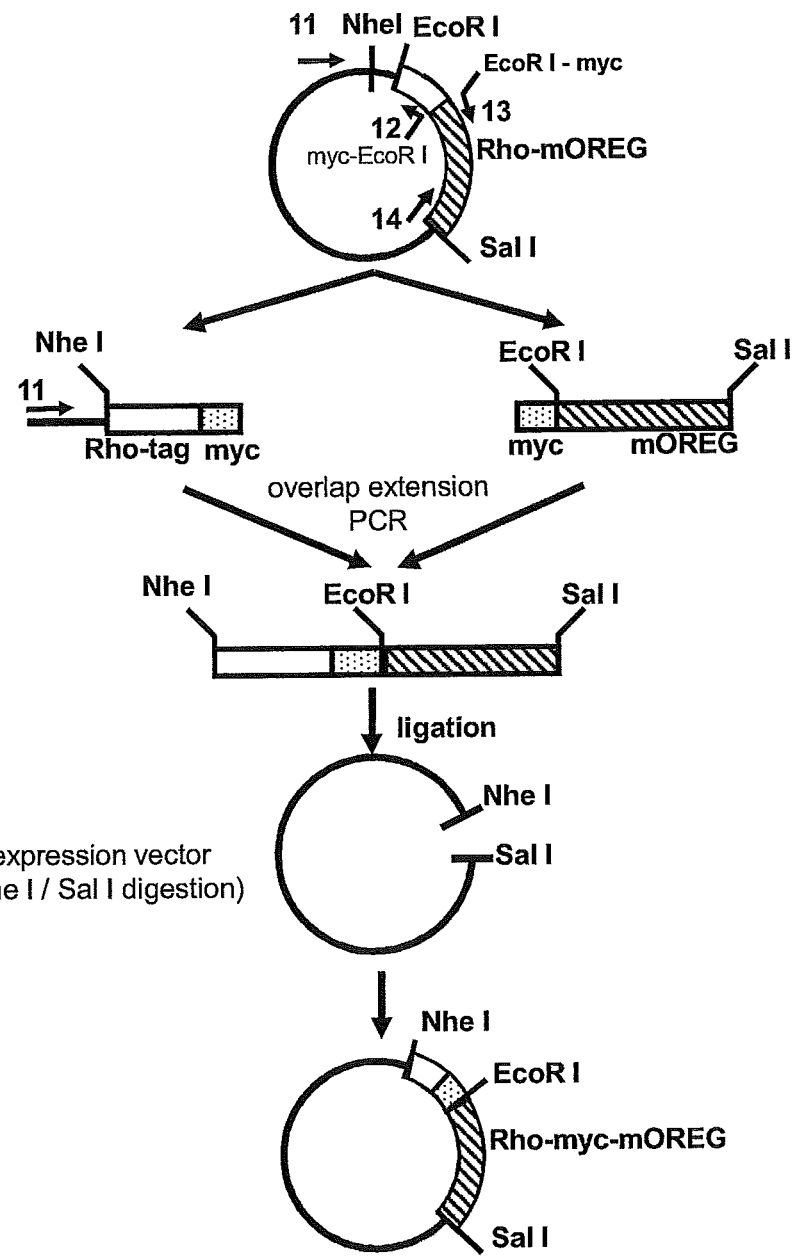
FIG. 12 shows a procedure for preparing a plasmid (Rho-myc-mOREG).

FIG. 12 shows a procedure for preparing a plasmid for expressing the mouse olfactory receptor for eugenol Rho-myc-mOREG, namely, a plasmid (Rho-myc-mOREG). This plasmid (Rho-myc-mOREG) is used to express the mouse olfactory receptor for eugenol Rho-myc-mOREG, as shown in FIG. 3. This olfactory receptor is abbreviated as "Rho-myc-mOREG".

(Step 1: Preparation of the Plasmid (Rho-myc-mOREG)

As shown in FIG. 12, two gene fragments were amplified using a plasmid (Rho-mOREG) obtained according to the comparative example 1-1 and two sets of primers.

The one gene fragment was amplified by a PCR method using the plasmid (Rho-mOREG), the primer 11, and the primer 12. The primer 12 had the antisense strand of the gene sequence coding for the myc epitope tag and had a restriction enzyme site EcoRI. In this way, amplified was the one gene fragment where the antisense strand of the gene sequence coding for the myc epitope tag (SEQ ID NO: 04) was added to the 3'-end of the Rho tag.

The other gene fragment was amplified by a PCR method using the plasmid (Rho-mOREG), the primer 13, and the primer 14. The primer 13 had a part of the myc epitope tag and a restriction enzyme site EcoRI. In this way, amplified was the other gene fragment where the part of the gene sequence coding for the myc epitope tag (SEQ ID NO: 04) was added to the 5'-end of the gene coding for the mOREG.

These two gene fragments thus amplified were mixed. These two gene fragments were connected by an overlap extension PCR method using the primer 11 and the primer 14. The connected gene fragments were ligated into a plasmid for expressing a mammal which had been treated with restriction enzymes NheI and SaI in advance. In this way, the plasmid (Rho-myc-mOREG) was obtained.

(Step 2: Expression of the Rho-myc-mOREG to a Cell Membrane)

The expression was conducted similarly to that of the step 2 of the reference example 1 except that the plasmid (Rho-myc-mOREG) was used instead of the plasmid (β1AR). In this way, the Rho-myc-mOREG (SEQ ID NO: 35) was expressed on a cell membrane.

(Step 3: Measurement of the Change Amount of the cAMP with an Agonist)

The concentration increase value was measured similarly to that of the step 3 of the comparative example 1-1: Rho-mOREG. The calculated concentration increase values are shown in Table 4 and FIG. 16.

Example 1-1

Chimera1

(Step 1: Preparation of the Plasmid (Chimera1))

As shown in FIG. 4, the chimeric olfactory receptor chimera1 consists of the amino acid sequence where the IC4 domain of the Rho-myc-mOREG is substituted with the IC4 domain of the beta-1 adrenergic receptor.

Figure 13:
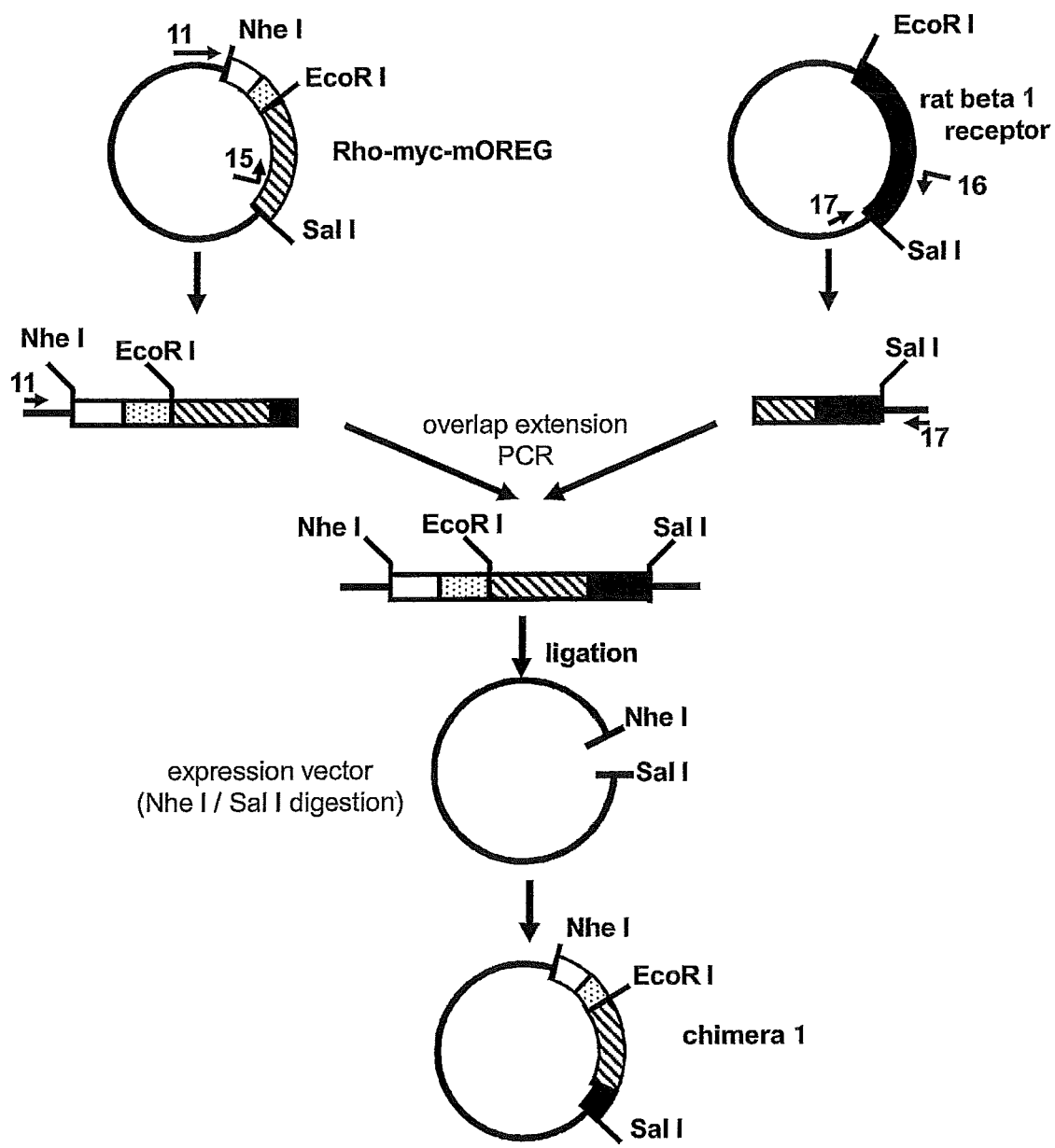
[FIG 13]

FIG. 13 shows a procedure for preparing a plasmid expressing the chimeric olfactory receptor chimera1, namely, a plasmid (chimera1). This plasmid (chimera1) is used to express the chimeric olfactory receptor chimera1, as shown in FIG. 4. This chimeric olfactory receptor is abbreviated as "chimera1".

(Step 1: Preparation of Plasmid (Chimera1))

As shown in FIG. 13, the gene fragment coding for the Rho-myc-mOREG which did not contain the IC4 domain was amplified by a PCR method using the plasmid (Rho-myc-mOREG), the primer 11, and the primer 15. As shown in the upper left of FIG. 13, the gene sequence interposed between the restriction enzyme site SalI and the primer 15 corresponds to the IC4 domain of the mOREG. In the example 1-1, the IC4 domain of the mOREG was not amplified.

On the contrary, the gene fragment coding for the IC4 domain of the beta-1 adrenergic receptor was amplified by a PCR method using the plasmid (β1AR), the primer 16, and the primer 17. As shown in the upper right of FIG. 13, the gene sequence interposed between the restriction enzyme site SalI and the primer 16 corresponds to the IC4 domain of the β1AR. In the example 1-1, the domains of the β1AR other than the IC4 domain of the β1AR were not amplified.

These two gene fragments were connected by an overlap extension PCR method using the primer 11 and the primer 17.

The connected gene fragments were treated with restriction enzymes NheI and SalI. Subsequently, the connected gene fragments were ligated into a plasmid for a mammal which had been treated with restriction enzymes NheI and SalI in advance. In this way, the plasmid (chimera 1) was prepared.

(Step 2: Expression of the Chimera1 to a Cell Membrane)

The expression was conducted similarly to that of the step 2 of the reference example 1 except that the plasmid (chimera1) was used instead of the plasmid (β1AR). In this way, the chimera1 (SEQ ID NO: 36) was expressed on a cell membrane.

(Step 3: Measurement of the Change Amount of the cAMP with an Agonist)

The concentration increase value was measured similarly to that of the step 3 of the comparative example 1-1: Rho-mOREG. The calculated concentration increase value is shown in Table 4 and FIG. 16.

Comparative Example 1-3

Chimera2

Figure 5:
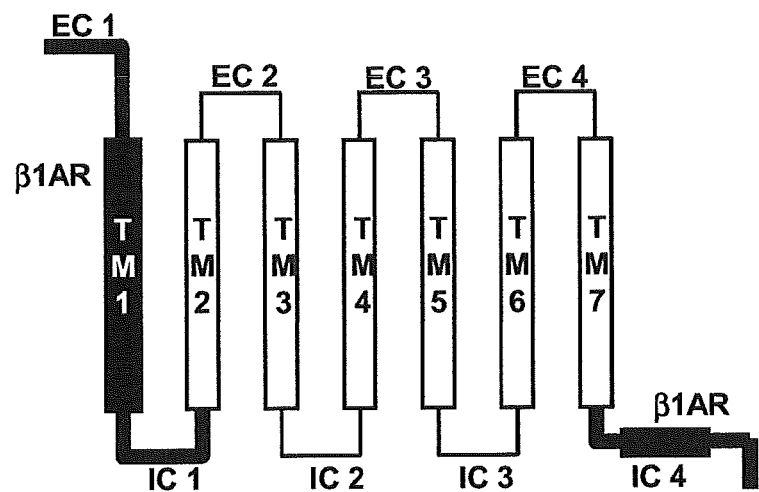
[FIG 5]

As shown in FIG. 5, the chimeric olfactory receptor chimera2 is comprised of the EC1-IC1 domains of the β1AR, the TM2-TM7 domains of the mOREG, and the IC4 domain of the β1AR. In other words, the chimeric olfactory receptor chimera2 consists of the amino acid sequence where the EC1 domain, the TM1 domain, IC1 domain, and the IC4 domain of the mOREG are substituted with those of the beta-1 adrenergic receptor.

Figure 14:
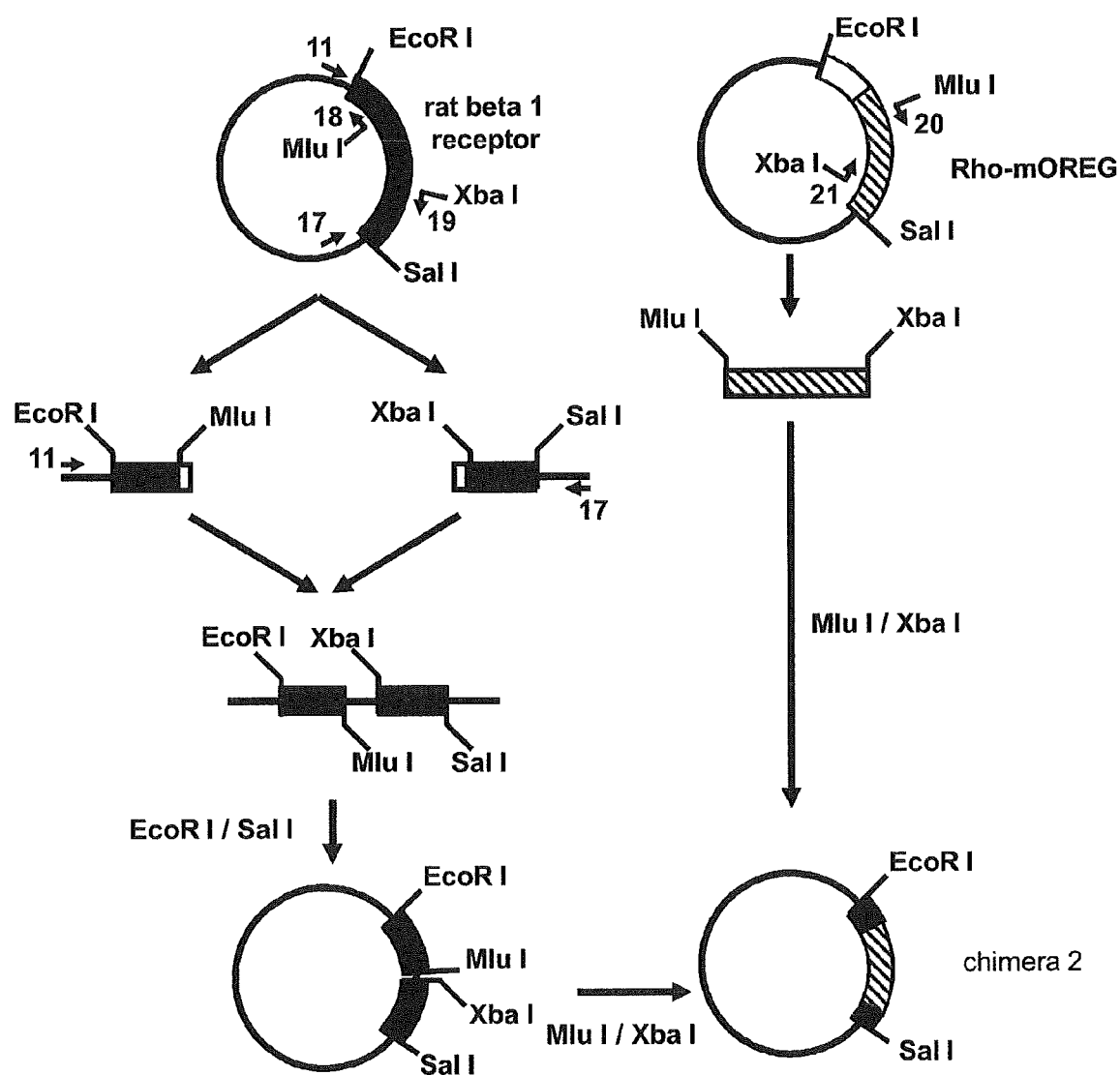
FIG. 14 shows a procedure for preparing a plasmid (chimera2).

FIG. 14 shows a procedure for preparing the plasmid for expressing the chimeric olfactory receptor chimera2, namely, the plasmid (chimera2). This plasmid (chimera2) is used to express the chimeric olfactory receptor chimera2, as shown in FIG. 5. This chimeric olfactory receptor is abbreviated as "chimera2".

(Step 1: Preparation of the Plasmid (Chimera2))

As shown in the left side of FIG. 14, the gene fragment coding for the EC1-IC1 domains of the β1AR was amplified by a PCR method using the plasmid (β1AR), the primer 11, and the primer 18. The primer 18 had a restriction enzyme site MluI.

Similarly, as shown in the left side of FIG. 14, the gene fragment coding for the IC4 domain of the β1AR was amplified by a PCR method using the plasmid (β1AR), the primer 19, and the primer 17. The primer 19 had a restriction enzyme site XbaI.

The gene fragments thus obtained were connected by an overlap extension PCR method using the primer 11 and the primer 17.

The connected gene fragments were treated with restriction enzymes EcoRI and SalI. Subsequently, the connected gene fragments were ligated in to a plasmid for expressing a mammal which had been treated with restriction enzymes EcoRI and SalI in advance, so as to obtain the plasmid shown in the lower left of FIG. 14.

On the contrary, as shown in right side of FIG. 14, the gene fragment coding for the TM2-TM7 domains of the mOREG was amplified by a PCR method using the plasmid (Rho-mOREG), the primer 20 and the primer 21. The primer 20 had a restriction enzyme site MluI. The primer 21 had a restriction enzyme site XbaI.

The obtained gene fragment was treated with restriction enzymes MluI and XbaI. Subsequently, the gene fragment was ligated into the plasmid shown in the lower left of FIG. 14. In this way, the plasmid (chimera2), which is shown in the lower right of FIG. 14, was obtained.

(Step 2: Expression of the Chimera2 to a Cell Membrane)

The expression was conducted similarly to that of the step 2 of the reference example 1 except that the plasmid (chimera2) was used instead of the plasmid (β1AR). In this way, the chimera2 (SEQ ID NO: 37) was expressed on a cell membrane.

(Step 3: Measurement of the Change Amount of the cAMP with an Agonist)

The concentration increase value was measured similarly to that of the step 3 of the comparative example 1-1: Rho-mOREG. The calculated concentration increase value is shown in Table 4 and FIG. 16.

Comparative Example 1-4

Chimera3

Figure 6:
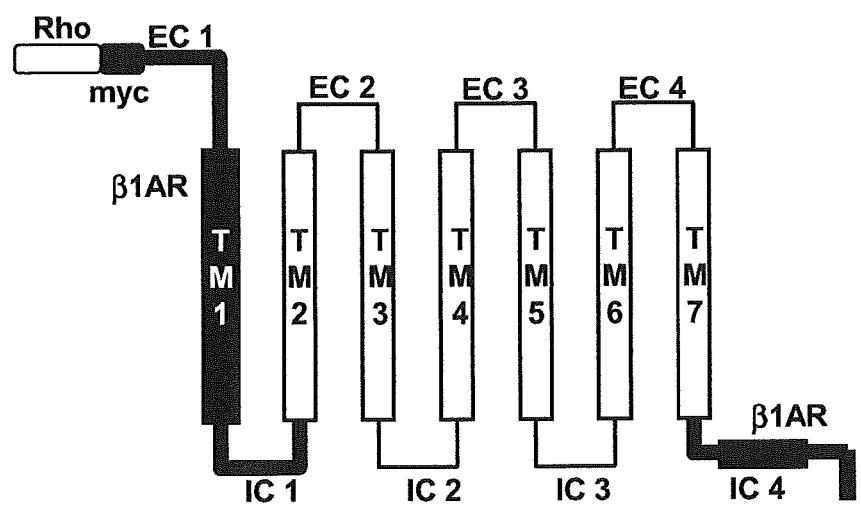
[FIG 6]

As shown in FIG. 6, the chimeric olfactory receptor chimera3 is comprised of the Rho-tag, the myc epitope tag, the EC1-IC1 domains of the β1AR, the TM2-TM7 domains of the mOREG, and the IC4 domain of the β1AR. In other words, the chimera3 consists of the amino acid sequence of the Rho-myc-mOREG where the EC1-IC1 domains and the IC4 domain thereof are substituted with those of the β1AR.

(Step 1: Preparation of the Plasmid (Chimera3))

Figure 21:
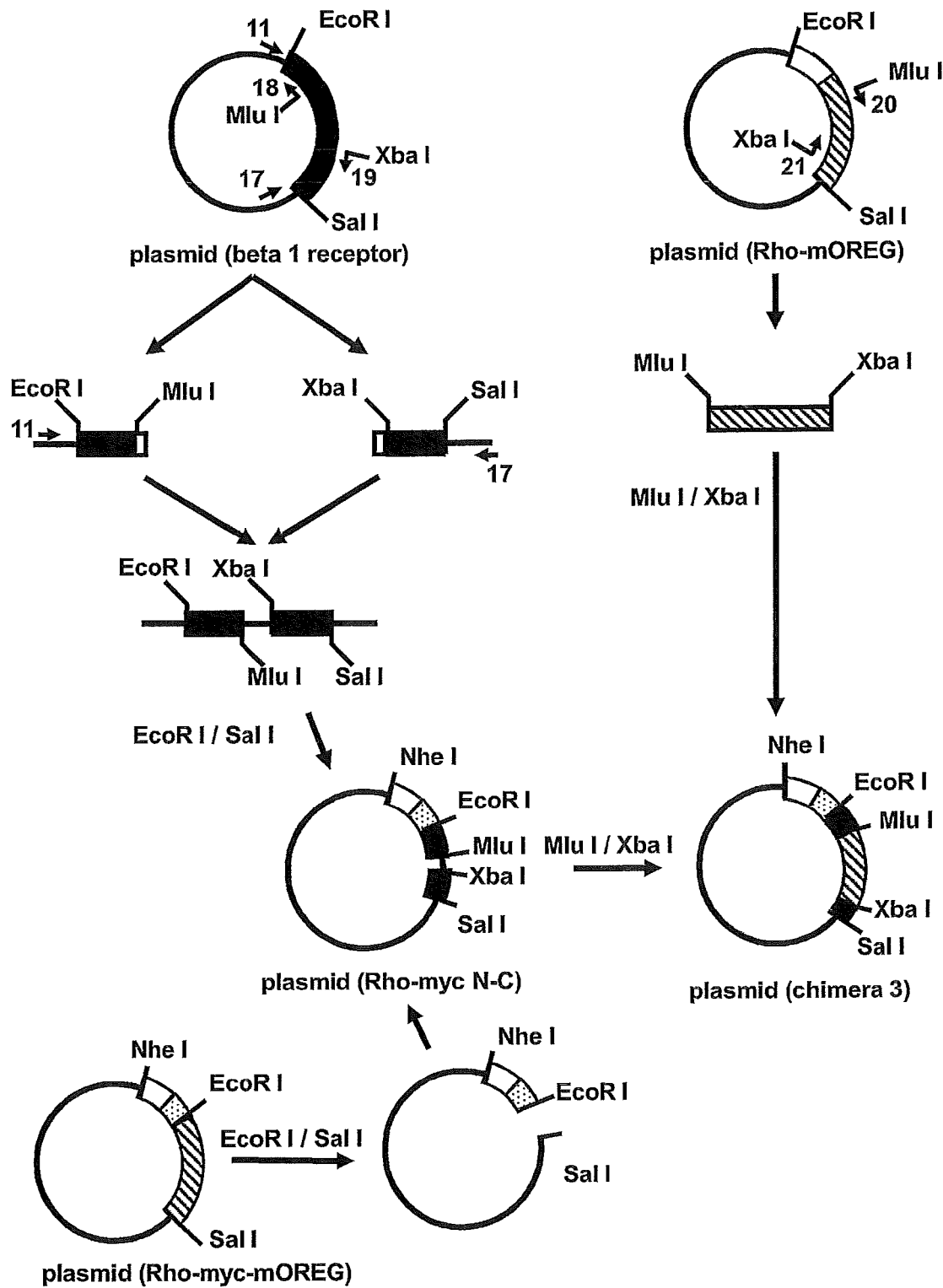
[FIG 21]

As shown in the left side of FIG. 21, the gene fragment coding for the EC1-IC1 domains of the β1AR was amplified using the plasmid (beta-1 adrenergic receptor), the primer 11, and the primer 18. The primer 18 had a restriction enzyme site MluI.

Similarly, as shown in the left side of FIG. 21, the gene fragment coding for the IC4 domain of the β1AR was amplified using the plasmid (beta-1 adrenergic receptor), the primer 17, and the primer 19. The primer 19 had a restriction enzyme site XbaI. The primer 19 had a gene fragment complementary to a part of the gene sequence of the primer 18.

The two gene fragments thus obtained were connected by an overlap extension PCR method using the primer 11 and the primer 17, so as to obtain the connected gene fragment.

Meanwhile, as shown in the lower left of FIG. 21, the plasmid (Rho-myc-mOREG) according to the comparative example 1-2 was treated with restriction enzymes EcoRI and SalI, so as to obtain a plasmid where the gene sequence coding for the mOREG was removed.

The connected gene fragments were ligated into the plasmid to obtain the plasmid (Rho-myc N—C).

As shown in the right side of FIG. 21, the gene fragment coding the TM2-TM7 domains of the mOREG was amplified with the plasmid (Rho-mOREG), the primer 20 and the primer 21. The primer 20 had a restriction enzyme site MluI. The primer 21 had a restriction enzyme site XbaI.

The amplified gene fragment was ligated into the plasmid (Rho-myc N—C) to obtain the plasmid (chimera3).

(Step 2: Expression of the Chimera3 to a Cell Membrane)

The expression was conducted similarly to that of the step 2 of the reference example 1 except that the plasmid (chimera3) was used instead of the plasmid (β1AR). In this way, the chimera3 (SEQ ID NO: 38) was expressed on a cell membrane.

(Step 3: Measurement of the Change Amount of the cAMP with an Agonist)

The concentration increase value was measured similarly to that of the step 3 of the comparative example 1-1: Rho-mOREG. The calculated concentration increase value is shown in Table 4 and FIG. 16.

Comparative Example 1-5

ChimeraTM7

Figure 7:
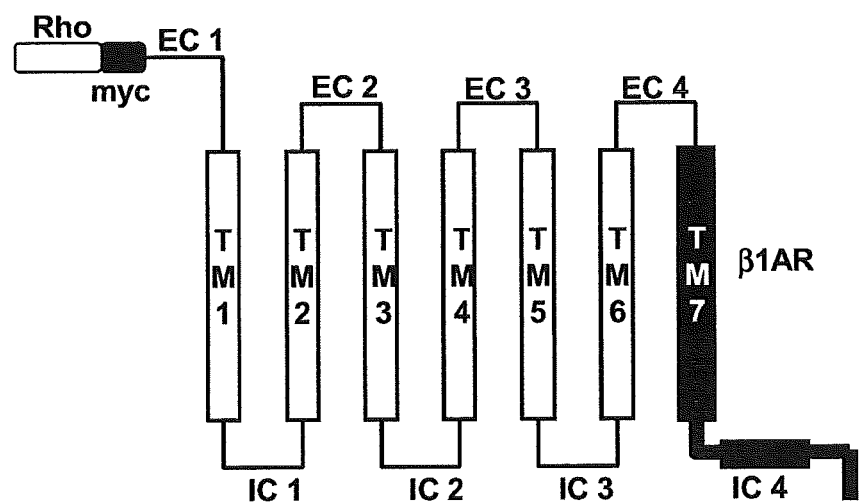
[FIG 7]

As shown in FIG. 7, the chimeric olfactory receptor chimeraTM7 is comprised of the Rho tag, the myc epitope tag, the EC1-EC4 domains of the mOREG, and the TM7-IC4 domains of the β1AR. In other words, the chimeric olfactory receptor chimeraTM7 has the amino acid sequence of the Rho-myc-mOREG where the TM7 domain and the IC4 domain thereof were substituted with those of the beta-1 adrenergic receptor.

(Step 1: Preparation of the Plasmid (ChimeraTM7))

Takara bio Co., Ltd. synthesized the gene fragment of the chimeraTM7 on the basis of the amino acid sequence represented by SEQ ID NO: 39. The synthesized gene fragment of the chimeraTM7 was ligated into EcoRI/SalI sites of a plasmid for expressing in a mammal. In this way, the plasmid (chimeraTM7) was obtained.

(Step 2: Expression of ChimeraTM7 to a Cell Membrane)

The expression was conducted similarly to that of the step 2 of the reference example 1 except that the plasmid (chimeraTM7) was used instead of the plasmid (β1AR). In this way, the chimeraTM7 (SEQ ID NO: 39) was expressed on a cell membrane.

(Step 3: Measurement of the Change Amount of the cAMP with an Agonist)

The concentration increase value was measured similarly to that of the step 3 of the comparative example 1-1: Rho-mOREG. The calculated concentration increase value is shown in Table 4 and FIG. 16.

Comparative Example 1-6

ChimeraIC3

Figure 8:
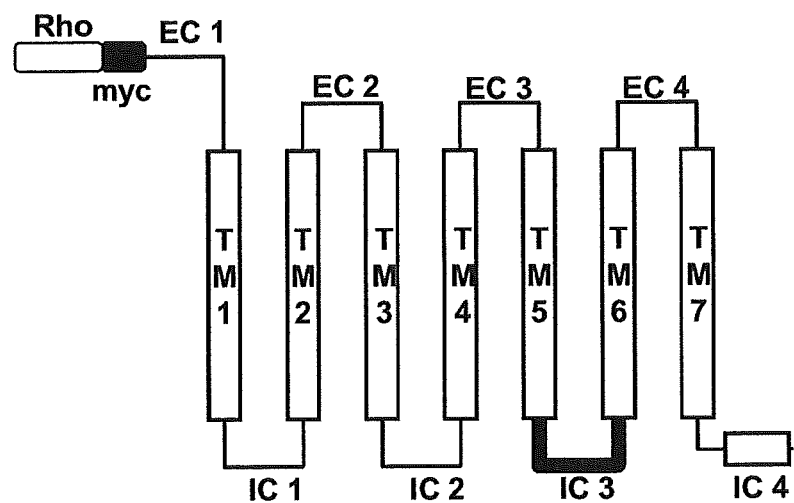
[FIG 8]

As shown in FIG. 8, the chimeric olfactory receptor chimeraIC3 is comprised of the Rho-tag, the myc epitope tag, the EC1-TM5 domains of the mOREG, the IC3 domain of the β1AR, and the TM6-IC4 domains of mOREG. In other words, the chimeric olfactory receptor chimeraIC3 has the amino acid sequence where the IC3 domain of Rho-myc-mOREG was substituted with that of beta-1 adrenergic receptor.

(Step 1: Preparation of ChimeraIC3)

Takara bio Co., Ltd. synthesized the gene fragment of the chimeraIC3 on the basis of the amino acid sequence represented by SEQ ID NO: 40. The synthesized gene fragment of the chimeraIC3 was ligated into EcoRI/SalI sites of a plasmid for expressing a mammal. In this way, the plasmid (chimeraIC3) was obtained.

(Step 2: Expression of ChimeraIC3 in a Cell Membrane)

The expression was conducted similarly to that of the step 2 of the reference example 1 except that the plasmid (chimeraIC3) was used instead of the plasmid (β1AR). In this way, the chimeraIC3 (SEQ ID NO: 40) was expressed on a cell membrane.

(Step 3: Measurement of the Change Amount of the cAMP with an Agonist)

The concentration increase value was measured similarly to that of the step 3 of the comparative example 1-1: Rho-mOREG. The calculated concentration increase value is shown in Table 4 and FIG. 16.

Comparative Example 1-7

ChimeraIC3-IC4)

Figure 9:
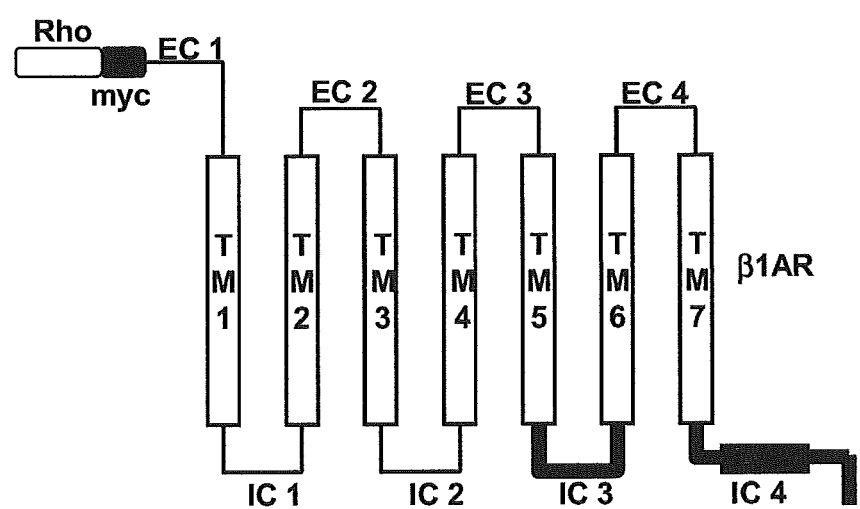
[FIG 9]

As shown in FIG. 9, the chimeric olfactory receptor chimeraIC3-IC4 is comprised of the Rho-tag, the myc epitope tag, the EC1-TM5 domains of the mOREG, the IC3 domain of the β1AR, the TM6-TM7 domains of the mOREG, and the IC4 domain of the β1AR. In other words, the chimeric olfactory receptor chimeraIC3-IC4 has the amino acid sequence where the IC3 and IC4 domains of the Rho-myc-mOREG were substituted with those of the beta-1 adrenergic receptor.

(Step 1: Preparation of the Plasmid (ChimeraIC3-IC4))

Takara bio Co., Ltd. synthesized the gene fragment of the chimeraIC3-IC4 on the basis of the amino acid sequence represented by SEQ ID NO: 41. The synthesized gene fragment of the chimera IC3-IC4 was ligated into EcoRI/SalI sites of a plasmid for expressing in a mammal. In this way, the plasmid (chimeraIC3-IC4) was obtained.

(Step 2: Expression of Chimera IC3-IC4 to a Cell Membrane

The expression was conducted similarly to that of the step 2 of the reference example 1 except that the plasmid (chimeraIC3-IC4) was used instead of the plasmid (β1AR). In this way, the chimeraIC3-IC4 (SEQ ID NO: 41) was expressed on a cell membrane.

(Step 3: Measurement of the Change Amount of the cAMP with an Agonist)

The concentration increase value was measured similarly to that of the step 3 of the comparative example 1-1: Rho-mOREG. The calculated concentration increase value is shown in Table 4 and FIG. 16.

Figure 16:
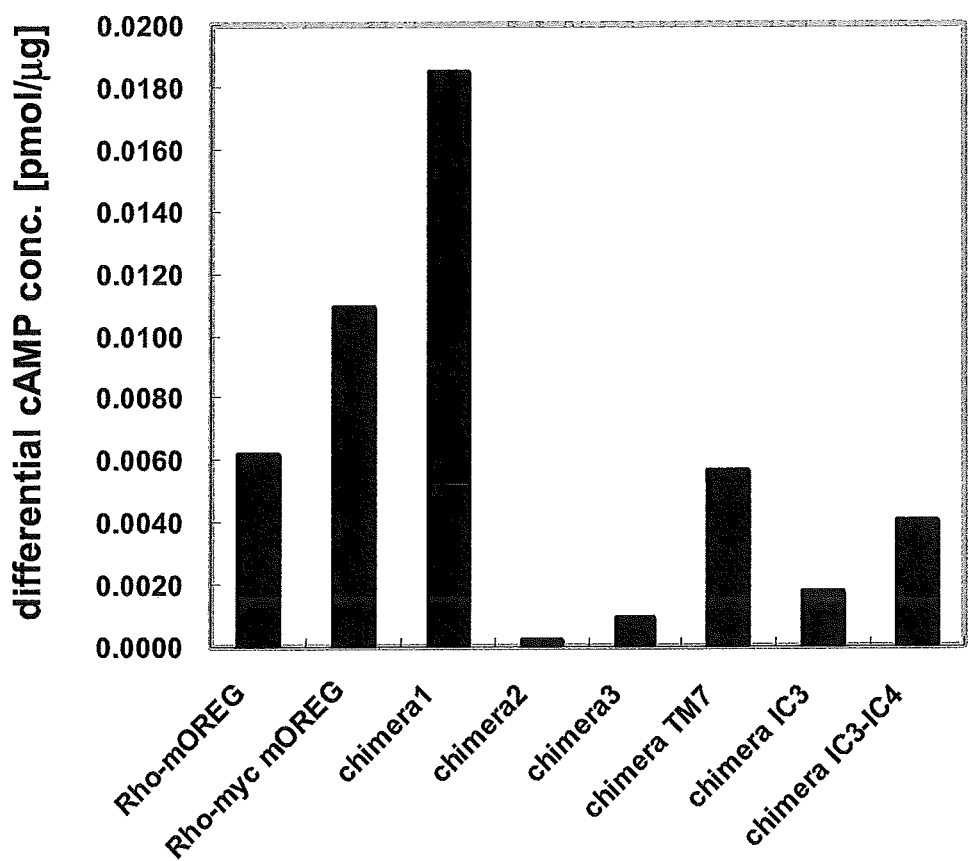
[FIG 16]

Table 4 shows the concentration increase values calculated in the example 1-1 and the comparative examples 1-1 to 1-7. FIG. 16 is a graph made based on Table 4.

TABLE 4

| | Receptor Name | Concentration increase value of the cAMP (unit: pmol/microgram) |
|---|---|---|
| Comparative example 1-1 | Rho-mOREG | 0.0061 |
| Comparative example 1-2 | Rho-myc-mOREG | 0.0109 |
| Example 1-1 | chimera1 | 0.0185 |
| Comparative example 1-3 | chimera2 | 0.0002 |
| Comparative example 1-4 | chimera3 | 0.0009 |
| Comparative example 1-5 | chimeraTM7 | 0.0056 |
| Comparative example 1-6 | chimeraIC3 | 0.0017 |
| Comparative example 1-7 | chimeraIC3-IC4 | 0.0040 |

As shown in Table. 4, the concentration increase value measured using the chimera1 is much greater than the concentration increase values measured using the other olfactory receptors derived from the mOREG.

(Eugenol Concentration-Dependency)

Figure 17:
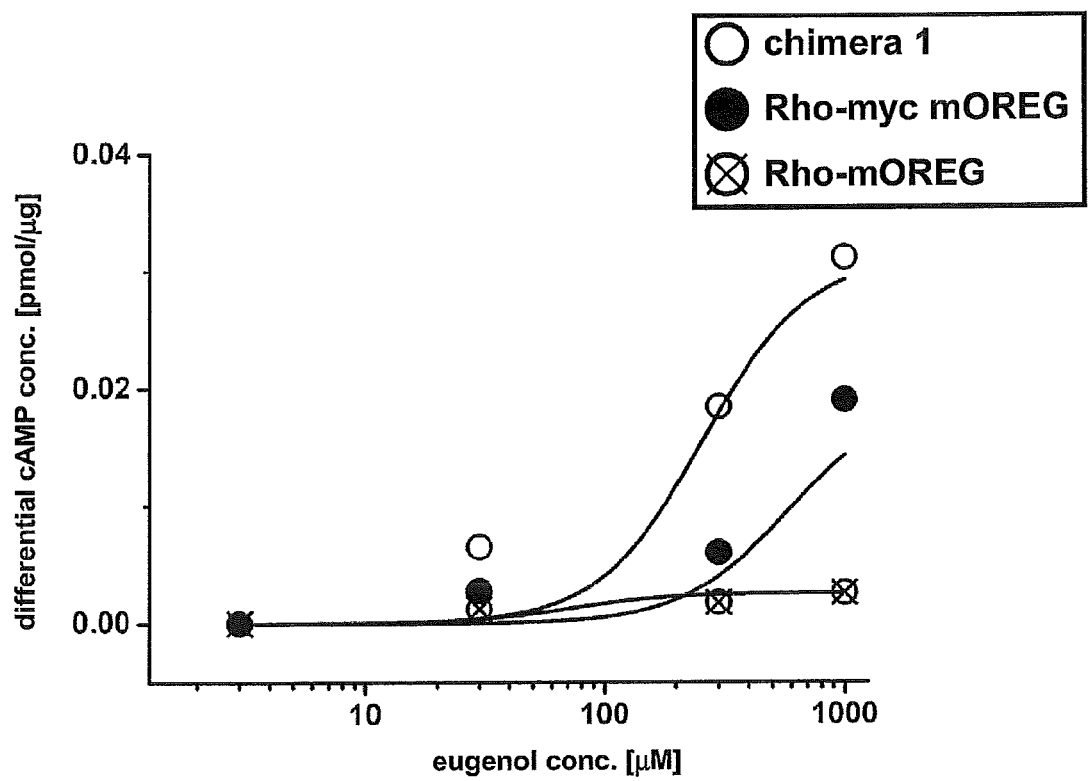
[FIG 17]

Table 5 shows the concentration increase values when eugenol aqueous solutions having a concentration of 30 μM, 300 μM and 1000 μM were used in the comparative example 1-1, the comparative example 1-2 and the example 1-1. FIG. 17 is a graph provided on the basis of Table 5.

TABLE 5

| Eugenol concentration (unit: μM) | Comparative example 1-1 (Rho-mOREG) | Comparative example 1-2 (Rho-myc-mOREG) | Example 1-1 (chimera1) |
|---|---|---|---|
| 30 | 0.0012 | 0.0028 | 0.0065 |
| 300 | 0.0018 | 0.0060 | 0.018 |
| 1000 | 0.0026 | 0.0190 | 0.031 |

As is clear from Table 5, regardless of the concentration of eugenol, which was used as an agonist, the concentration increase value of the cAMP measured using the chimera1 is greater than the concentration increase values of the cAMP measured using the other olfactory receptors.

A skilled person in the art could choose agonistic concentration depending on an agonist appropriately.

Experiment 2

In the experiment 2, transgenic proteins of mouse olfactory receptors for 2-pentanone (Olfr168) were produced.

The experiment 2 includes one example (Example 2-1) and one comparative example (Comparative example 2-1).

Comparative Example 2-1

Rho-myc-Olfr168

Figure 18:
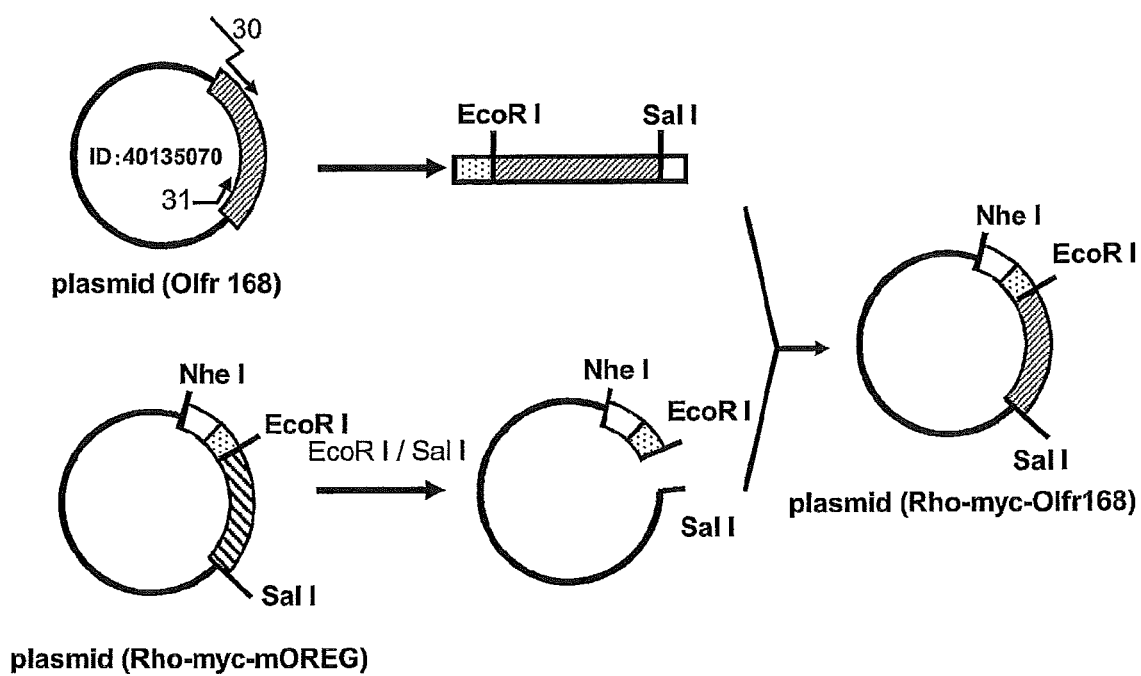
[FIG 18]

FIG. 18 shows a procedure for preparing a plasmid for expressing the mouse olfactory receptor for 2-pentanone Rho-myc-Olfr168, namely, a plasmid (Rho-myc-Olfr168). This plasmid (Rho-myc-Olfr168) is used for expressing the mouse olfactory receptor for 2-pentanone Rho-myc-Olfr168, as shown in FIG. 3. Hereinafter, this olfactory receptor is abbreviated as "Rho-myc-Olfr168". As shown in FIG. 3, the olfactory receptor Rho-myc-Olfr168 is composed of the Rho-tag, the myc epitope tag, and the EC1-IC4 domains of the Olfr168. The olfactory receptor Rho-myc-Olfr168 consists of the amino acid sequence represented by SEQ ID NO: 49.

(Step 1: Preparation of the Plasmid (Rho-myc-Olfr168))

As shown in FIG. 18, a plasmid having a gene (GenBank Accession Number: BC127969.1) coding for the Olfr168 was purchased from Mammalian Gene Collection as ID: 40135070. The gene coding for the Olfr168 was amplified by a PCR method using the above-mentioned plasmid, the primer 30 (SEQ ID NO: 46), and the primer 31 (SEQ ID NO: 47). The primer 30 and the primer 31 had a restriction enzyme site EcoRI and SalI, respectively. In this way, the gene fragment represented by SEQ ID NO: 48 was obtained.

Meanwhile, the plasmid (Rho-myc-mOREG) according to the comparative example 1-2 was treated with restriction enzymes EcoRI and SalI so as to obtain a plasmid where the gene sequence coding for the mOREG was removed. The above-mentioned gene fragment was ligated into this plasmid so as to obtain the plasmid (Rho-myc-Olfr168). The plasmid (Rho-myc-Olfr168) contained the gene sequence represented by SEQ ID NO: 57.

(Step 2: Expression of Rho-myc-Olfr168 to a Cell Membrane)

The expression was conducted similarly to that of the step 2 of the reference example 1 except that the plasmid (Rho-myc-Olfr168) was used instead of the plasmid (β1AR). In this way, the Rho-myc-Olfr168 (SEQ ID NO: 49) was expressed on a cell membrane.

(Step 3: Measurement of the Change Amount of the cAMP with an Agonist)

The concentrations of the cAMP were measured similarly to the step 3 of the comparative example 1-1 except that 2-pentanone aqueous solutions having concentrations of 30 μM, 100 μM, 300 μM, 1000 μM, and 3000 μM were used as agonists instead of the eugenol aqueous solutions. The result was shown in Table 6.

Example 2-1

ChimeraOlfr168)

As shown in FIG. 4, the chimeric olfactory receptor chimeraOlfr168 is comprised of the Rho-tag, the myc epitope tag, the EC1-TM7 domains of the Olfr168, and the IC4 domain of the β1AR. In other words, the chimeric olfactory receptor chimeraOlfr168 consists of the amino acid sequence of the Rho-myc-Olfr168 where the IC4 domain thereof was substituted with that of the beta-1 adrenergic receptor.

(Step 1: Preparation of the Plasmid (ChimeraOlfr168))

Takara bio Co., Ltd. synthesized the gene fragment (SEQ ID NO: 67) coding for the chimeraOlfr168 on the basis of the amino acid sequence represented by SEQ ID NO: 50. This synthesized gene fragment of the chimeraOlfr168 was ligated into EcoRI/SalI sites of a plasmid for expressing a mammal. In this way, the plasmid (chimeraOlfr168) was obtained.

(Step 2: Expression of ChimeraOlfr168 to a Cell Membrane)

The expression was conducted similarly to that of the step 2 of the reference example 1 except that the plasmid (chimeraOlfr168) was used instead of the plasmid (β1AR). In this way, the chimeraOlfr168 (SEQ ID NO: 51) was expressed on a cell membrane.

(Step 3: Measurement of the Change Amount of the cAMP with an Agonist)

The concentrations of the cAMP were measured similarly to the step 3 of the comparative example 2-1.

Table 6 shows the concentrations of the cAMP measured in the example 2-1 and the comparative example 2-1.

TABLE 6

| Concentration of the 2-pentanone (unit: μM) | Rho-myc-Olfr168 | chimeraOlfr168 |
|---|---|---|
| 0 | 0.0215 | 0.0187 |
| 30 | 0.0170 | 0.0220 |
| 100 | 0.0170 | 0.0270 |
| 300 | 0.0280 | 0.0520 |
| 1000 | 0.0400 | 0.0775 |
| 3000 | 0.0444 | 0.0916 |

As is clear from Table 6, the concentration of the cAMP measured using the chimeraOlfr168 is much greater than the concentration of the cAMP measured using Rho-myc-Olfr168.

Experiment 3

In the experiment 3, transgenic proteins of mouse olfactory receptors for cyclohexanone (Olfr15) were produced.

The experiment 3 includes one example (Example 3-1) and one comparative example (Comparative example 3-1).

Comparative Example 3-1

Rho-myc-Olfr15

Figure 19:
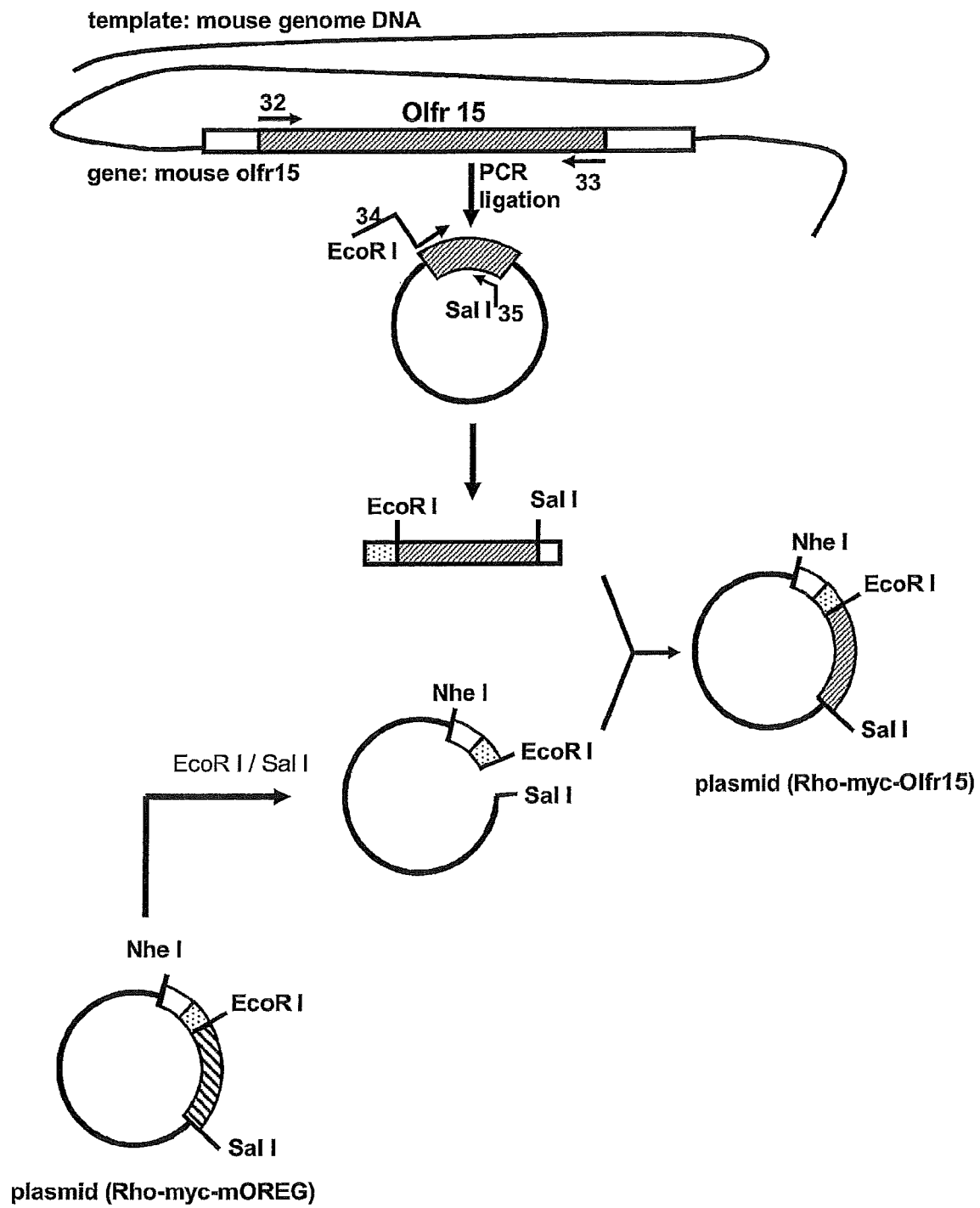
[FIG 19]

FIG. 19 shows a procedure for preparing a plasmid for expressing the mouse olfactory receptor for cyclohexanone Rho-myc-Olfr15, namely, a plasmid (Rho-myc-Olfr15). This plasmid (Rho-myc-Olfr15) is used for expressing the mouse olfactory receptor for cyclohexanone Rho-myc-Olfr15, as shown in FIG. 2. Hereinafter, this olfactory receptor is abbreviated as "Rho-myc-Olfr15". As shown in FIG. 2, the olfactory receptor Rho-myc-Olfr15 is composed of the Rho-tag, the myc epitope tag, and the EC1-IC4 domains of the Olfr15. The olfactory receptor Rho-myc-Olfr15 consists of the amino acid sequence represented by SEQ ID NO: 58.

(Step 1: Preparation of the Plasmid (Rho-myc-Olfr15))

First, the gene (GenBank Accession Number: BC146531) coding for the Olfr15 was amplified by a PCR method using a mouse genomic DNA as a template. In this PCR method, the primer 32 (SEQ ID NO: 52), and the primer 33 (SEQ ID NO: 53) were used. Thus, the gene fragment represented by SEQ ID NO: 56 was obtained.

This gene fragment was ligated into a plasmid for cloning so as to obtain a plasmid.

The gene fragment was amplified by a PCR method using this plasmid, the primer 34 (SEQ ID NO: 54), and the primer 35 (SEQ ID NO: 55). The primer 34 (SEQ ID NO: 54), and the primer 35 (SEQ ID NO: 55) had a restriction enzyme site EcoRI and SalI, respectively.

Meanwhile, the plasmid (Rho-myc-mOREG) according to the comparative example 1-2 was treated with restriction enzymes EcoRI and SalI so as to obtain a plasmid where the gene sequence coding for the mOREG was removed. The above-mentioned gene fragment was ligated into this plasmid so as to obtain a plasmid (Rho-myc-Olfr15). The plasmid (Rho-myc-Olfr15) contained the gene sequence represented by SEQ ID NO: 70.

(Step 2: Expression of Rho-myc-Olfr15 to a Cell Membrane)

The expression was conducted similarly to that of the step 2 of the reference example 1 except that the plasmid (Rho-myc-Olfr15) was used instead of the plasmid (β1AR). In this way, the Rho-myc-Olfr15 (SEQ ID NO: 58) was expressed on a cell membrane.

(Step 3: Measurement of the Change Amount of the cAMP with an Agonist)

Instead of the eugenol aqueous solutions, the concentrations of the cAMP were measured similarly to the step 3 of the comparative example 1-1 except that cyclohexanone aqueous solutions having concentrations of 30 μM, 100 μM, 300 μM, 1000 μM, and 3000 μM were used as agonists. The result was shown in Table 7.

Example 3-1

ChimeraOlfr15

As shown in FIG. 4, the chimeric olfactory receptor chimeraOlfr15 is comprised of the Rho-tag, the myc epitope tag, the EC1-TM7 domains of the Olfr15, and the IC4 domain of the β1AR. In other words, the chimeric olfactory receptor chimeraOlfr15 consists of the amino acid sequence where the IC4 domain of the Rho-myc-Olfr15 was substituted with that of the beta-1 adrenergic receptor.

(Step 1: Preparation of the Plasmid (ChimeraOlfr15))

Takara bio Co., Ltd. synthesized the gene fragment (SEQ ID NO: 68) coding for the chimeraOlfr15 on the basis of the gene sequence represented by SEQ ID NO: 59. This synthesized gene fragment of the chimeraOlfr15 was ligated into EcoRI/SalI sites of a plasmid for expressing in a mammal. In this way, the plasmid (chimeraOlfr15) was obtained.

(Step 2: Expression of ChimeraOlfr15 to a Cell Membrane)

The expression was conducted similarly to that of the step 2 of the reference example 1 except that the plasmid (chimeraOlfr15) was used instead of the plasmid (β1AR). In this way, the chimeraOlfr15 (SEQ ID NO: 60) was expressed on a cell membrane.

(Step 3: Measurement of the Change Amount of the cAMP with an Agonist)

The concentrations of the cAMP were measured similarly to the step 3 of the comparative example 3-1.

Table 7 shows the concentrations of the cAMP measured in the example 3-1 and the comparative example 3-1.

TABLE 7

| Concentration of cyclohexanone (Unit: μM) | Rho-myc-Olfr15 | chimeraOlfr15 |
|---|---|---|
| 0 | 0.0173 | 0.0282 |
| 30 | 0.0180 | 0.0280 |
| 100 | 0.0210 | 0.0250 |
| 1000 | 0.0280 | 0.0290 |
| 3000 | 0.0444 | 0.0916 |

As is clear from Table 7, the concentration of the cAMP measured using the chimeraOlfr15 is much greater than the concentration of the cAMP measured using the Rho-myc-olfr15.

Experiment 4

In the experiment 4, transgenic proteins of mouse olfactory receptors for vanillic acid Olfr609 were produced.

The experiment 4 includes one example (Example 4-1) and one comparative example (Comparative example 4-1).

Comparative Example 4-1

Rho-myc-Olfr609

Figure 20:
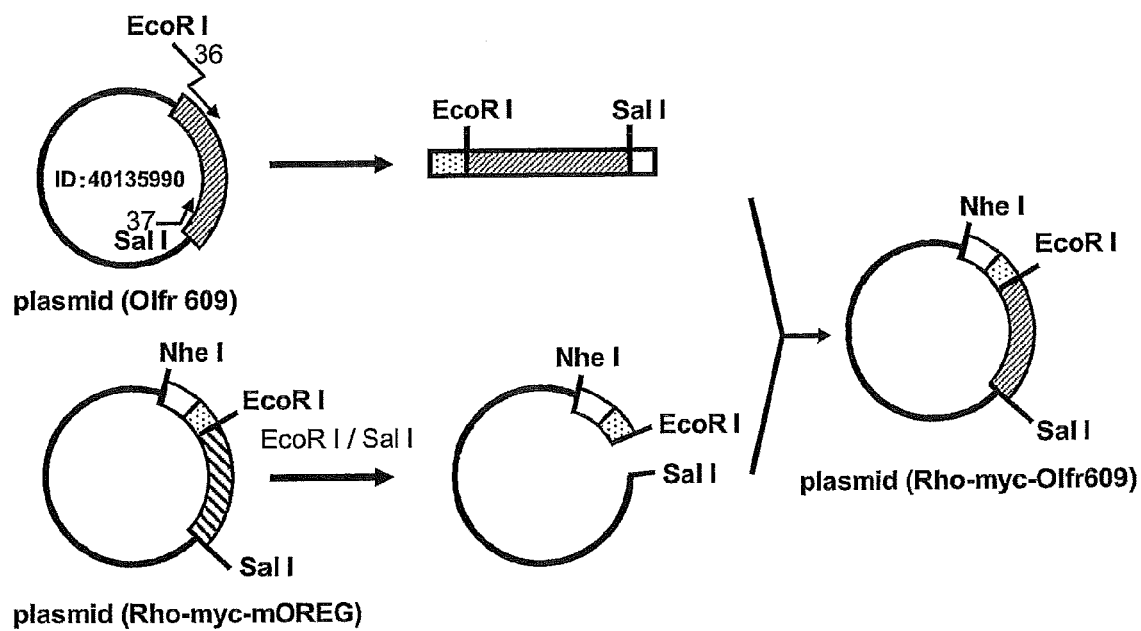
[FIG 20]

FIG. 20 shows a procedure for preparing a plasmid for expressing the mouse olfactory receptor for vanillic acid Rho-myc-Olfr609, namely, a plasmid (Rho-myc-Olfr609). This plasmid (Rho-myc-Olfr609) is used for expressing the mouse olfactory receptor for vanillic acid Rho-myc-Olfr609, as shown in FIG. 2. Hereinafter, this olfactory receptor is abbreviated as "Rho-myc-Olfr609". As shown in FIG. 2, the olfactory receptor Rho-myc-Olfr609 is composed of the Rho-tag, the myc epitope tag, and the EC1-IC4 domains of the Olfr609. The olfactory receptor Rho-myc-Olfr609 consists of the amino acid sequence represented by SEQ ID NO: 64.

(Step 1: Preparation of the Plasmid (Rho-myc-Olfr609))

First, a plasmid having a gene coding for the mouse olfactory receptor for vanillic acid Olfr609 was purchased from Mammalian Gene Collection as ID: 40135990. The gene coding for the Olfr609 was amplified by a PCR method using the above-mentioned plasmid, the primer 36 (SEQ ID NO: 61), and the primer 37 (SEQ ID NO: 62). The primer 36 and the primer 37 had a restriction enzyme site EcoRI and SalI, respectively. In this way, the gene fragment represented by SEQ ID NO: 63 was obtained.

Meanwhile, the plasmid (Rho-myc-mOREG) according to the comparative example 1-2 was treated with restriction enzymes EcoRI and SalI so as to obtain a plasmid where the gene sequence coding for the mOREG was removed. The above-mentioned gene fragment was ligated into this plasmid so as to obtain a plasmid (Rho-myc-Olfr609). The plasmid (Rho-myc-Olfr609) contained the amino acid sequence represented by SEQ ID NO: 71.

(Step 2: Expression of Rho-myc-Olfr609 to a Cell Membrane)

The expression was conducted similarly to that of the step 2 of the reference example 1 except that the plasmid (Rho-myc-Olfr609) was used instead of the plasmid (β1AR). In this way, the Rho-myc-Olfr609 (SEQ ID NO: 64) was expressed on a cell membrane.

(Step 3: Measurement of the Change Amount of the cAMP with an Agonist)

Instead of the eugenol aqueous solutions, the concentrations of the cAMP were measured similarly to the step 3 of the comparative example 1-1 except that vanillic acid aqueous solutions having concentrations of 0.30 μM, 1 μM, 3 μM, 10 μM, and 30 μM were used as agonists. The result was shown in Table 8.

Example 4-1

ChimeraOlfr609

As shown in FIG. 3, the chimeric olfactory receptor chimeraOlfr609 is comprised of the Rho-tag, the myc epitope tag, the EC1-TM7 domains of the Olfr609, and the IC4 domain of the β1AR. In other words, the chimeric olfactory receptor chimeraOlfr609 consists of the amino acid sequence where the IC4 domain of the Rho-myc-Olfr609 was substituted with that of the beta-1 adrenergic receptor.

(Step 1: Preparation of the Plasmid (ChimeraOlfr609))

Takara bio Co., Ltd. synthesized the gene fragment (SEQ ID NO: 66) coding for the chimeraOlfr609 on the basis of the gene sequence represented by SEQ ID NO: 65. This synthesized gene fragment of the chimeraOlfr609 was ligated into EcoRI/SalI sites of a plasmid for expressing a mammal. In this way, the plasmid (chimeraOlfr609) was obtained.

(Step 2: Expression of ChimeraOlfr609 to a Cell Membrane)

The expression was conducted similarly to that of the step 2 of the reference example 1 except that the plasmid (chimeraOlfr609) was used instead of the plasmid (β1AR). In this way, the chimeraOlfr609 (SEQ ID NO: 69) was expressed on a cell membrane.

(Step 3: Measurement of the Change Amount of the cAMP with an Agonist)

The concentrations of the cAMP were measured similarly to the step 3 of the comparative example 4-1.

Table 8 shows the concentrations of the cAMP measured in the example 4-1 and the comparative example 4-1.

TABLE 8

| Concentration of vanillic acid (Unit: μM) | Rho-myc-Olfr609 | chimeraOlfr609 |
|---|---|---|
| 0 | 0.014 | 0.075 |
| 0.3 | 0.070 | 0.166 |
| 1 | 0.076 | 0.160 |
| 3 | 0.127 | 0.192 |
| 10 | 0.067 | 0.162 |
| 30 | 0.071 | 0.187 |

As is clear from Table 8, the concentration of the cAMP measured using the chimeraOlfr609 is much greater than the concentration of the cAMP measured using the Rho-myc-Olfr609.

While the invention has been described in detail, the foregoing description is in all aspects illustrative and not restrictive. It will be understood that numerous other modifications and variations can be devised without departing from the scope of the present invention. It should be understood that the scope of the present invention is definitely interpreted only on the basis of the scope of the claims. Furthermore, it should be understood that a person ordinarily skilled in the art can carry out an equivalent scope of invention based on the descriptions of the present invention and the common technological knowledge, by referring to the descriptions of the specific preferred embodiments of the present invention. It will be understood as a matter of course that throughout the present specification, unless otherwise particularly stated, a singular expression encompasses the concept of plurality as well. Therefore, it will be understood as a matter of course that, unless otherwise particularly stated, a singular article or adjective (e.g., "a", "an", "the" or the like in English) encompasses the concept of plurality as well. Furthermore, it will be understood as a matter of course that, unless otherwise particularly stated, the terms used in the present specification are used in the meaning as conventionally used in the related art. Therefore, unless defined otherwise, all the jargon and technical terms used in the present specification have the same meanings as generally understood by those skilled in the art to which the present invention is pertained. In the case of contradiction, the present specification (including the definitions) dominates.

INDUSTRIAL APPLICABILITY

The present invention provides a chimeric olfactory receptor capable of increasing the product amount of the cAMP. The chemical substance such as an odor molecule is high-sensitively detected or quantified using the chimeric olfactory receptor according to the present invention.

[Brief Description for Sequence Listing]

SEQ ID NO:1 N-terminal Fragment of Bovine Rhodopsin derived from bovine optical nerve
SEQ ID NO:2 Mouse-derived olfactory receptor for eugenol (olfactory bulb)
SEQ ID NO:3 β1 adrenergic receptor (β1AR; derived from Bovine heart)
SEQ ID NO:4 Tag for labelling with antibody
SEQ ID NO:5 Primer for preparing plasmid expressing β1 adrenergic receptor
SEQ ID NO:6 Primer for preparing plasmid expressing β1 adrenergic receptor
SEQ ID NO:7 Primer for preparing plasmid expressing β1 adrenergic receptor
SEQ ID NO:8 Primer for preparing plasmid expressing β1 adrenergic receptor
SEQ ID NO:9 Primer for preparing plasmid expressing β1 adrenergic receptor
SEQ ID NO:10 Primer for preparing plasmid expressing β1 adrenergic receptor
SEQ ID NO:11 Primer for preparing plasmid expressing Rho-mOREG
SEQ ID NO:12 Primer for preparing plasmid expressing Rho-mOREG
SEQ ID NO:13 Primer for preparing plasmid expressing Rho-mOREG
SEQ ID NO:14 Primer for preparing plasmid expressing Rho-mOREG
SEQ ID NO:15 Primer for preparing plasmid expressing Rho-myc-mOREG
SEQ ID NO:16 Primer for preparing plasmid expressing Rho-myc-mOREG
SEQ ID NO:17 Primer for preparing plasmid expressing Rho-myc-mOREG
SEQ ID NO:18 Primer for preparing plasmid expressing Rho-myc-mOREG
SEQ ID NO:19 Primer for preparing plasmid expressing chimera 1
SEQ ID NO:20 Primer for preparing plasmid expressing chimera 1
SEQ ID NO:21 Primer for preparing plasmid expressing chimeras 1 and 2
SEQ ID NO:22 Primer for preparing plasmid expressing chimera 2
SEQ ID NO:23 Primer for preparing plasmid expressing chimera 2
SEQ ID NO:24 Primer for preparing plasmid expressing chimera 2
SEQ ID NO:25 Primer for preparing plasmid expressing chimera 2
SEQ ID NO:26 Primer for preparing plasmid expressing Gαolf
SEQ ID NO:27 Primer for preparing plasmid expressing Gαolf
SEQ ID NO:28 Primer for preparing plasmid expressing Gαolf
SEQ ID NO:29 Primer for preparing plasmid expressing Gαolf
SEQ ID NO:30 Primer for preparing plasmid expressing RTP1S
SEQ ID NO:31 Primer for preparing plasmid expressing RTP1S
SEQ ID NO:32 Primer for preparing plasmid expressing RTP1S
SEQ ID NO:33 Primer for preparing plasmid expressing RTP1S
SEQ ID NO:34 Rho-mOREG
SEQ ID NO:35 Rho-myc-mOREG
SEQ ID NO:36 Chimera 1
SEQ ID NO:37 Chimera 2
SEQ ID NO:38 Chimera 3
SEQ ID NO:39 Chimera TM7
SEQ ID NO:40 Chimera IC3
SEQ ID NO:41 Chimera IC3-IC4
SEQ ID NO:42 Mouse-derived protein RTP1S
SEQ ID NO:43 Mouse-derived olfactory receptor Olfr168
SEQ ID NO:44 Mouse olfactory receptor for cyclohexanone
SEQ ID NO:45 Mouse olfactory receptor for vanillic acid
SEQ ID NO:46 Primer for preparing plasmid expressing Rho-myc-Olfr168
SEQ ID NO:47 Primer for preparing plasmid expressing Rho-myc-Olfr168
SEQ ID NO:48 Mouse-derived gene fragment
SEQ ID NO:49 Rho-myc-olfr168
SEQ ID NO:50 Fragments for preparing ChimeraOlfr168
SEQ ID NO:51 ChimeraOlfr168
SEQ ID NO:52 Primer for preparing plasmid expressing Rho-myc-Olfr15
SEQ ID NO:53 Primer for preparing plasmid expressing Rho-myc-Olfr15
SEQ ID NO:54 Primer for preparing plasmid expressing Rho-myc-Olfr15
SEQ ID NO:55 Primer for preparing plasmid expressing Rho-myc-Olfr15
SEQ ID NO:56 Mouse-derived gene fragment
SEQ ID NO:57 Fragment coding for Rho-myc-Olfr168
SEQ ID NO:58 Rho-myc-Olfr15
SEQ ID NO:59 Fragments for preparing ChimeraOlfr15
SEQ ID NO:60 ChimeraOlfr15
SEQ ID NO:61 Primer for preparing plasmid expressing Rho-myc-Olfr609
SEQ ID NO:62 Primer for preparing plasmid expressing Rho-myc-Olfr609
SEQ ID NO:63 Mouse-derived gene fragment
SEQ ID NO:64 Rho-myc-olfr609
SEQ ID NO:65 Fragments for preparing ChimeraOlfr609
SEQ ID NO:66 Fragment coding for Chimera Olfr609
SEQ ID NO:67 Fragment coding for Chimera Olfr168
SEQ ID NO:68 Fragment coding for Chimera Olfr15
SEQ ID NO:69 Chimera Olfr609
SEQ ID NO:70 Fragment coding for Rho-myc-Olfr15
SEQ ID NO:71 Fragment coding for Rho-myc-Olfr609

What is claimed is:

1. A method for producing cAMP using a chimeric olfactory receptor, the method comprising steps of:
   (a) preparing a reaction system comprising a first layer, a lipid bilayer membrane, and a second layer; wherein
   the lipid bilayer membrane is interposed between the first layer and the second layer,
   the lipid bilayer membrane comprises the chimeric olfactory receptor and adenylate cyclase;
   the chimeric olfactory receptor penetrates the lipid bilayer membrane;
   the adenylate cyclase penetrates the lipid bilayer membrane;
   the second layer contains ATP and a G protein;
   the G protein is placed in the vicinity of one end of the chimeric olfactory receptor;
   the chimeric olfactory receptor is derived from a mouse olfactory receptor consisting of an amino acid sequence of (N-terminal)—an EC1 domain—a TM1 domain—an IC1 domain—a TM2 domain—an EC2 domain—a TM3 domain—an IC2 domain—a TM4 domain—an EC3 domain—a TM5 domain—an IC3 domain—a TM6 domain—an EC4 domain—a TM7 domain—an IC4 domain—(C-terminal);
   the N-terminal of the chimeric olfactory receptor is modified with an amino acid sequence of Rho tag (SEQ ID NO:01)—myc epitope tag (SEQ ID NO:04); and
   the IC4 is substituted with an IC4 domain of a beta-1 adrenergic receptor; and
   (b) supplying a chemical substance which stimulates the chimeric olfactory receptor to the first layer so as to produce the cAMP from the ATP.

2. The method according to claim 1, wherein
   the mouse olfactory receptor is a mouse olfactory receptor for eugenol;
   the chemical substance is eugenol.

3. The method according to claim 1, wherein
   the mouse olfactory receptor is a mouse olfactory receptor Olfr168;
   the chemical substance is 2-pentanone.

4. The method according to claim 1, wherein
   the mouse olfactory receptor is a mouse olfactory receptor Olfr15;
   the chemical substance is cyclohexanone.

5. The method according to claim 1, wherein
   the mouse olfactory receptor is a mouse olfactory receptor Olfr609;
   the chemical substance is vanillic acid.

6. The method according to claim 2, wherein
   the chimeric olfactory receptor consists of the amino acid sequence represented by SEQ ID NO: 36.

7. The method according to claim 3, wherein
   the chimeric olfactory receptor consists of the amino acid sequence represented by SEQ ID NO: 51.

8. The method according to claim 4, wherein
   the chimeric olfactory receptor consists of the amino acid sequence represented by SEQ ID NO: 60.

9. The method according to claim 5, wherein
   the chimeric olfactory receptor consists of the amino acid sequence represented by SEQ ID NO: 69.

10. The method according to claim 1, wherein
    the G protein comprises Gαolf, Gβ and, Gγ;
    in the step (b), the G protein is divided into the Gαolf and a complex;
    the complex consists of the Gβ and the Gγ; and
    the Gαolf activates the adenylate cyclase.

11. The method according to claim 1, wherein
    the lipid bilayer membrane further comprises an ion channel;
    the ion channel penetrates the lipid bilayer membrane; and
    the cAMP produced in the step (b) activates the ion channel.

12. The method according to claim 11, wherein
    the ion channel is a calcium ion channel.

13. A method for determining whether or not a sample solution contains a molecule which stimulates a chimeric olfactory receptor; the method comprising:
    (a) preparing a reaction system comprising a first layer, a lipid bilayer membrane, and a second layer; wherein
    the lipid bilayer membrane is interposed between the first layer and the second layer,
    at least one layer of the first layer and the second layer contains ions;

the lipid bilayer membrane comprises the chimeric olfactory receptor, an ion channel, and adenylate cyclase;
the chimeric olfactory receptor penetrates the lipid bilayer membrane;
the adenylate cyclase penetrates the lipid bilayer membrane;
the ion channel penetrates the lipid bilayer membrane;
the second layer contains ATP and a G protein;
the G protein is placed in the vicinity of one end of the chimeric olfactory receptor;
the chimeric olfactory receptor is derived from a mouse olfactory receptor consisting of an amino acid sequence of (N-terminal)—an EC1 domain—a TM1 domain—an IC1 domain—a TM2 domain—an EC2 domain—a TM3 domain—an IC2 domain—a TM4 domain—an EC3 domain—a TM5 domain—an IC3 domain—a TM6 domain—an EC4 domain—a TM7 domain—an IC4 domain—(C-terminal);
the N-terminal of the chimeric olfactory receptor is modified with an amino acid sequence of Rho tag (SEQ ID NO:01)-myc epitope tag (SEQ ID NO:04); and
the IC4 is substituted with an IC4 domain of a beta-1 adrenergic receptor; and
(b) supplying the sample solution to the first layer and measuring the concentration of the ions contained in the at least one layer of the first layer and the second layer; and
(c) determining, if the measured concentration of the ions is varied, that the sample solution contains the molecule which stimulates the chimeric olfactory receptor.

14. The method according to claim 13, wherein
the mouse olfactory receptor is a mouse olfactory receptor for eugenol;
the molecule which stimulates a chimeric olfactory receptor is eugenol.

15. The method according to claim 13, wherein
the mouse olfactory receptor is a mouse olfactory receptor Olfr168;
the molecule which stimulates a chimeric olfactory receptor is 2-pentanone.

16. The method according to claim 13, wherein
the mouse olfactory receptor is a mouse olfactory receptor Olfr15;
the molecule which stimulates a chimeric olfactory receptor is cyclohexanone.

17. The method according to claim 13, wherein
the mouse olfactory receptor is a mouse olfactory receptor Olfr609;
the molecule which stimulates a chimeric olfactory receptor is vanillic acid.

18. The method according to claim 14, wherein
the chimeric olfactory receptor consists of the amino acid sequence represented by SEQ ID NO: 36.

19. The method according to claim 15, wherein
the chimeric olfactory receptor consists of the amino acid sequence represented by SEQ ID NO: 51.

20. The method according to claim 16, wherein
the chimeric olfactory receptor consists of the amino acid sequence represented by SEQ ID NO: 60.

21. The method according to claim 17, wherein
the chimeric olfactory receptor consists of the amino acid sequence represented by SEQ ID NO: 69.

22. The method according to claim 13, wherein
the G protein comprises Gαolf, Gβ and, Gγ;
in the step (b), the G protein is divided into the Gαolf and a complex;
the complex consists of the Gβ and the Gγ; and
the Gαolf activates the adenylate cyclase.

23. The method according to claim 13, wherein
cAMP produced in the step (b) activates the ion channel.

24. The method according to claim 13, wherein
the ion channel is a calcium ion channel.

25. A method for quantifying a chemical substance which is contained in a sample solution and which stimulates a chimeric olfactory receptor; the method comprising:
(a) preparing a reaction system comprising a first layer, a lipid bilayer membrane, and a second layer; wherein
the lipid bilayer membrane is interposed between the first layer and the second layer,
at least one layer of the first layer and the second layer contains ions;
the lipid bilayer membrane comprises the chimeric olfactory receptor, an ion channel, and adenylate cyclase;
the chimeric olfactory receptor penetrates the lipid bilayer membrane;
the adenylate cyclase penetrates the lipid bilayer membrane;
the ion channel penetrates the lipid bilayer membrane;
the second layer contains ATP and a G protein;
the G protein is placed in the vicinity of one end of the chimeric olfactory receptor;
the chimeric olfactory receptor is derived from a mouse olfactory receptor consisting of an amino acid sequence of (N-terminal)—an EC1 domain—a TM1 domain—an IC1 domain—a TM2 domain—an EC2 domain—a TM3 domain—an IC2 domain—a TM4 domain—an EC3 domain—a TM5 domain—an IC3 domain—a TM6 domain—an EC4 domain—a TM7 domain—an IC4 domain—(C-terminal);
the N-terminal of the chimeric olfactory receptor is modified with an amino acid sequence of Rho tag (SEQ ID NO:01)—myc epitope tag (SEQ ID NO:04); and
the IC4 is substituted with an IC4 domain of a beta-1 adrenergic receptor; and
(b) supplying the sample solution to the first layer and measuring the concentration of the ions contained in the at least one layer of the first layer and the second layer; and
(c) quantifying the chemical substance which is contained in the sample solution on the basis of the amount of the change of the measured concentration of the ion.

26. The method according to claim 25, wherein
the mouse olfactory receptor is a mouse olfactory receptor for eugenol;
the chemical substance is eugenol.

27. The method according to claim 25, wherein
the mouse olfactory receptor is a mouse olfactory receptor Olfr168;
the chemical substance is 2-pentanone.

28. The method according to claim 25, wherein
the mouse olfactory receptor is a mouse olfactory receptor Olfr15;
the chemical substance is cyclohexanone.

29. The method according to claim 25, wherein
the mouse olfactory receptor is a mouse olfactory receptor Olfr609;
the chemical substance is vanillic acid.

30. The method according to claim 26, wherein
the chimeric olfactory receptor consists of the amino acid sequence represented by SEQ ID NO: 36.

31. The method according to claim 27, wherein
the chimeric olfactory receptor consists of the amino acid sequence represented by SEQ ID NO: 51.

32. The method according to claim 28, wherein
the chimeric olfactory receptor consists of the amino acid sequence represented by SEQ ID NO: 60.

33. The method according to claim 29, wherein
the chimeric olfactory receptor consists of the amino acid sequence represented by SEQ ID NO: 69.

34. The method according to claim 25, wherein
the G protein comprises Gαolf, Gβ and, Gγ;
in the step (b), the G protein is divided into the Gαolf and a complex;
the complex consists of the Gβ and the Gγ; and
the Gαolf activates the adenylate cyclase.

35. The method according to claim 25, wherein
cAMP produced in the step (b) activates the ion channel.

36. The method according to claim 25, wherein
the ion channel is a calcium ion channel.

37. A chimeric olfactory receptor represented by SEQ ID NO: 36.

38. A chimeric olfactory receptor represented by SEQ ID NO: 51.

39. A chimeric olfactory receptor represented by SEQ ID NO: 60.

40. A chimeric olfactory receptor represented by SEQ ID NO: 69.

41. A lipid bilayer membrane which is comprised as part of a reaction system used for detecting or quantifying a chemical substance contained in a sample solution, comprising:
a chimeric olfactory receptor;
an ion channel;
and adenylate cyclase; wherein
the chimeric olfactory receptor penetrates the lipid bilayer membrane;
the adenylate cyclase penetrates the lipid bilayer membrane;
the ion channel penetrates the lipid bilayer membrane;
the G protein is placed in the vicinity of one end of the chimeric olfactory receptor;
the chimeric olfactory receptor is derived from a mouse olfactory receptor consisting of an amino acid sequence of (N-terminal)—an EC1 domain—a TM1 domain—an IC1 domain—a TM2 domain—an EC2 domain—a TM3 domain—an IC2 domain—a TM4 domain—an EC3 domain—a TM5 domain—an IC3 domain—a TM6 domain—an EC4 domain—a TM7 domain—an IC4 domain—(C-terminal);
the N-terminal of the chimeric olfactory receptor is modified with an amino acid sequence of Rho tag (SEQ ID NO:01)—myc epitope tag (SEQ ID NO:04); and
the IC4 is substituted with an IC4 domain of a beta-1 adrenergic receptor.

42. The lipid bilayer membrane according to claim 41, wherein
The chimeric olfactory receptor consists of the amino acid sequence represented by SEQ ID NO: 36.

43. The lipid bilayer membrane according to claim 41, wherein
The chimeric olfactory receptor consists of the amino acid sequence represented by SEQ ID NO: 51.

44. The lipid bilayer membrane according to claim 41, wherein
The chimeric olfactory receptor consists of the amino acid sequence represented by SEQ ID NO: 60.

45. The lipid bilayer membrane according to claim 41, wherein
The chimeric olfactory receptor consists of the amino acid sequence represented by SEQ ID NO: 69.

46. A reaction system used for detecting or quantifying a chemical substance contained in a sample solution, comprising:
a first layer;
a lipid bilayer membrane;
and a second layer; wherein
the lipid bilayer membrane is interposed between the first layer and the second layer,
at least one layer of the first layer and the second layer contains ions;
the lipid bilayer membrane comprises the chimeric olfactory receptor, an ion channel, and adenylate cyclase;
the chimeric olfactory receptor penetrates the lipid bilayer membrane;
the adenylate cyclase penetrates the lipid bilayer membrane;
the ion channel penetrates the lipid bilayer membrane;
the second layer contains ATP and a G protein;
the G protein is placed in the vicinity of one end of the chimeric olfactory receptor;
the chimeric olfactory receptor is derived from a mouse olfactory receptor consisting of an amino acid sequence of (N-terminal)—an EC1 domain—a TM1 domain—an IC1 domain—a TM2 domain—an EC2 domain—a TM3 domain—an IC2 domain—a TM4 domain—an EC3 domain—a TM5 domain—an IC3 domain—a TM6 domain—an EC4 domain—a TM7 domain—an IC4 domain—(C-terminal);
the N-terminal of the chimeric olfactory receptor is modified with an amino acid sequence of Rho tag (SEQ ID NO:01)—myc epitope tag (SEQ ID NO:04); and
the IC4 is substituted with an IC4 domain of a beta-1 adrenergic receptor.

47. The reaction system according to claim 46, wherein
The chimeric olfactory receptor consists of the amino acid sequence represented by SEQ ID NO: 36.

48. The reaction system according to claim 46, wherein
The chimeric olfactory receptor consists of the amino acid sequence represented by SEQ ID NO: 51.

49. The reaction system according to claim 46, wherein
The chimeric olfactory receptor consists of the amino acid sequence represented by SEQ ID NO: 60.

50. The reaction system according to claim 46, wherein
The chimeric olfactory receptor consists of the amino acid sequence represented by SEQ ID NO: 69.

* * * * *